United States Patent
Sasai et al.

(10) Patent No.: US 10,227,563 B2
(45) Date of Patent: Mar. 12, 2019

(54) METHOD FOR CULTURE OF STEM CELL

(75) Inventors: Yoshiki Sasai, Kobe (JP); Takafumi Wataya, Kobe (JP); Mototsugu Eiraku, Kobe (JP)

(73) Assignee: RIKEN, Wako (JP)

( * ) Notice: Subject to any disclaimer, the term of this patent is extended or adjusted under 35 U.S.C. 154(b) by 133 days.

(21) Appl. No.: 12/996,503

(22) PCT Filed: Jun. 5, 2009

(86) PCT No.: PCT/JP2009/060396
§ 371 (c)(1),
(2), (4) Date: Dec. 6, 2010

(87) PCT Pub. No.: WO2009/148170
PCT Pub. Date: Dec. 10, 2009

(65) Prior Publication Data
US 2011/0091869 A1  Apr. 21, 2011

(30) Foreign Application Priority Data

Jun. 6, 2008 (JP) ................. 2008-149880
Oct. 31, 2008 (JP) ................. 2008-282299

(51) Int. Cl.
*C12N 5/0797* (2010.01)

(52) U.S. Cl.
CPC ........ *C12N 5/0623* (2013.01); *C12N 2501/33* (2013.01); *C12N 2501/415* (2013.01); *C12N 2501/42* (2013.01); *C12N 2501/70* (2013.01); *C12N 2506/02* (2013.01)

(58) Field of Classification Search
CPC .............. C12N 5/0623; C12N 2501/33; C12N 2501/415; C12N 2501/42; C12N 2501/70; C12N 2506/02
See application file for complete search history.

(56) References Cited

U.S. PATENT DOCUMENTS

| | | | |
|---|---|---|---|
| 2003/0068819 A1* | 4/2003 | Zhang et al. ................. | 435/368 |
| 2005/0095702 A1 | 5/2005 | Alam et al. | |
| 2006/0211109 A1 | 9/2006 | Totey et al. | |
| 2006/0252148 A1 | 11/2006 | Kurosawa et al. | |
| 2008/0044901 A1 | 2/2008 | Sasai et al. | |
| 2010/0105137 A1 | 4/2010 | Takahashi et al. | |
| 2011/0027333 A1 | 2/2011 | Idelson et al. | |
| 2013/0040330 A1 | 2/2013 | Sasai et al. | |

FOREIGN PATENT DOCUMENTS

| | | |
|---|---|---|
| EP | 1 068 295 A1 | 1/2001 |
| EP | 1 783 205 A1 | 5/2007 |
| EP | 2 128 244 A1 | 12/2009 |
| JP | 2002-517982 A | 6/2002 |
| JP | 2003-055402 A | 2/2003 |
| JP | 2004-229523 A | 8/2004 |
| JP | 2004-254622 A | 9/2004 |
| JP | 2004-305014 A | 11/2004 |
| JP | 2005-261365 A | 9/2005 |
| JP | 2006-055069 A | 3/2006 |
| JP | 2006-521807 A | 9/2006 |
| JP | 2007-520207 A | 7/2007 |
| JP | 2008-099662 A | 5/2008 |
| WO | WO 1999/053021 A1 | 10/1999 |
| WO | WO 2005/001019 A1 | 1/2005 |
| WO | WO 2005/123902 A1 | 12/2005 |
| WO | WO 2005123902 A1 * | 12/2005 |
| WO | WO 2008/035110 A1 | 3/2008 |
| WO | WO 2008/087917 A1 | 7/2008 |
| WO | WO 2008/129554 A1 | 10/2008 |

OTHER PUBLICATIONS

Crawford et al., Developmental Dynamics, 236: 886-892, 2007.*
Ng et al., Nature Protocols, 3(5): 768-776, Apr. 2008.*
Ezekiel et al., Electronic J. of Biotechnology, 10(20): 328-335, Apr. 15, 2007.*
Riken Press Release, "ES saibo kara Shishokabu Neuron Bunka Yudo to Hormon Sansei ni Seiko—Naibunpitsu ya Sesshoku Shogai no Kenkyu ni Koken suru Atarashii Tool" (Aug. 5, 2008).
Japanese Patent Office, International Search Report in International Patent Application No. PCT/JP2009/060396 (dated Aug. 4, 2009).
International Bureau of WIPO, International Preliminary Report on Patentability in International Patent Application No. PCT/JP2009/060396 (dated Jan. 11, 2011).
Muguruma et al., *Experimental Medicine*, 26(5): 733-739 (Mar. 20, 2008).
Ikeda et al., *Proc. Natl. Acad. Sci. USA.*, 102(32): 11331-11336 (Aug. 9, 2005).
Su et al., *Developmental Biology*, 290: 287-296 (2006).
Eiraku et al., *Cell Stem Cell*, 3(5); 519-532 (Nov. 6, 2008).
Nelson et al., *Developmental Biology*, 304(2): 479-498 (2007).
Watanabe et al., *Nature Biotechnology*, 25(6): 681-686 (May 27, 2007).
Watanabe et al., *Nature Neuroscience*, 8(3): 288-296 (Feb. 6, 2005).
Wataya et al., *Proc. Natl. Acad. Sci. USA.*, 105(33): 11796-11801 (Aug. 19, 2008).
Osakada et al., *Nature Biotechnology*, 26(2): 215-224 (Feb. 1, 2008).
Schulz et al., *Stem Cells*, 22(7): 1218-1238 (Jan. 1, 2004).
European Patent Office, Supplementary European Search Report in European Application No. 09 75 8437 (dated Jun. 11, 2012).

(Continued)

*Primary Examiner* — Thaian N Ton
(74) *Attorney, Agent, or Firm* — Leydig, Voit & Mayer, Ltd.

(57) ABSTRACT

The present invention enables efficient suspension culture of stem cells in a serum-free medium by comprising a step for quickly forming homogenous aggregates of stem cells, and provides a method of selectively inducing the differentiation of nerves from a stem cell, a method of forming a cerebral cortical nerve network in vitro, and a method of producing a steric structure of a brain tissue in vitro, as well as a method of producing hypothalamic neuron progenitor cells, comprising culturing pluripotent stem cells as suspended aggregates in a serum-free medium that substantially does not contain a Nodal signal promoter, a Wnt signal promoter, an FGF signal promoter, a BMP signal promoter, retinoic acid and an insulin, and isolating hypothalamic neuron progenitor cells from the culture.

26 Claims, 19 Drawing Sheets

(56) References Cited

OTHER PUBLICATIONS

Hirami et al., *Neuroscience Letters*, 458: 126-131 (2009).
Ikeda et al., *Jikken-igaku*, 24: 188-194 (2006).
Japanese Patent Office, International Search Report in International Patent Application No. PCT/JP2010/070163 (dated Feb. 15, 2011).
Japanese Patent Office, Written Opinion of the International Searching Authority in International Patent Application No. PCT/JP2010/070163 (dated Feb. 15, 2011).
Kurosawa et al., "Novel Culture Technique for Formation of Mouse ES Cell Embryoid Body," *Department of Engineering, University of Yamanashi, Research Report*, 52: 23-29 (2003).
Eiraku et al., *Nature*, 472: 51-56 (2011).
Lamba et al., *Proc. Natl. Acad. Sci. USA*, 103: 12769-12774 (2006).
Zhong et al., *Journal of Clinical Rehabilitative Tissue Engineering Research*, 12(51): 10117-101120 (2008).
Farnsworth et al., "Directed Neural Differentiation of Induced Pluripotent Stem Cells from Nonhuman Primates," *Exp. Biol. Med.* (Maywood), 238(3): 276-284 (Mar. 1, 2013).
Mariani et al., "Modeling Human Cortical Development In Vitro Using Induced Pluripotent Stem Cells," *Proc. Natl. Acad. Sci. USA*, 109(31): 12770-12775 (Jul. 31, 2012).
Ng et al., "Forced Aggregation of Defined Numbers of Human Embryonic Stem Cells into Embryoid Bodies Fosters Robust, Reproducible Hematopoietic Differentiation," *Blood*, 106(5): 1601-1603 (Sep. 1, 2005).
Fujiwara et al., *Journal of Biological Chemistry*, 282(40): 29701-29711 (Oct. 5, 2007).
Carpenedo et al., *Stem Cells*, 25: 2224-2234 (2007).
Krencik et al., *Frontiers in Cellular Neuroscience*, 7: Article 25 (Mar. 14, 2013).
Kurosawa, *Journal of Bioscience and Bioengineering*, 103(5): 389-398 (2007).
Lee et al., *Tissue Engineering: Part C*, 15(00): 1-11 (Aug. 3, 2009).
Moeller et al., *Biomaterials*, 29(6): 752-763 (2008).
Petros et al., *Frontiers in Molecular Neuroscience*, 4: Article 30 (Oct. 12, 2011).
Watanabe et al., "Directed differentiation of telencephalic precursors from embryonic stem cells," *Nature Neuroscience*, 8(3): 288-296 with supplementary figures 1-8 and descriptions therefor (Mar. 2005).
Yang et al., "In Vitro Isolation and Expansion of Human Retinal Progenitor Cells," 177: 326-331 (2002).
Eiraku et al., "Mouse embryonic stem cell culture for generation of three-dimensional retinal and cortical tissues," *Nature Protocols*, 7(1): 69-79 (2012).
Kuwahara et al., "Generation of a ciliary margin-like stem cell niche from self-organizing human retinal tissue," *Nature Communications*, 6: 6286 (2015).
Nakano et al., "Self-Formation of Optic Cups and Storable Stratified Neural Retina from Human ESCs," *Cell Stem Cell*, 10(6): 771-785 and including supplemental information (2012).
Sakaguchi et al., "Generation of functional hippocampal neurons from self-organizing human embryonic stem cell-derived dorsomedial telencephalic tissue," *Nature Communications*, 6: 8896 (2015).
Gonzalez-Cordero et al., "Photoreceptor precursors derived from three-dimensional embryonic stem cell cultures integrate and mature within adult degenerate retina," *Nat. Biotechnol.*, 31(8): 741-747 (2013).
Kadoshima et al., "Self-organization of axial polarity, inside-out layer pattern, and species-specific progenitor dynamics in human ES cell-derived neocortex," *Proc. Natl. Acad. Sci. USA*, 110(50): 20284-20289 (2013).
Muguruma et al., "Ontogeny-recapitulating generation and tissue integration of ES cell-derived Purkinje cells," *Nat. Neurosci.*, 13(10): 1171-1180 and Online Methods (2010).
Muguruma et al., "Self-Organization of Polarized Cerebellar Tissue in 3D Culture of Human Pluripotent Stem Cells," *Cell Rep.*, 10(4): 537-550 (2015).
Nicholas et al., "Functional maturation of hPSC-derived-forebrain interneurons requires an extended timeline and mimics human neural development," *Cell Stem Cell*, 12(5): 573-586 (2013).
Ozone et al., "Functional anterior pituitary generated in self-organizing culture of human embryonic stem cells," *Nat. Commun.*, 7: 10351 (2016).
Suga et al., "Self-formation of functional adenohypophysis in three-dimensional culture," *Nature*, 480(7375): 57-62 and Methods (2011).
Troy et al. "Commitment of Embryonic Stem Cells to an Epidermal Cell Fate and Differentiation in Vitro," *Dev Dyn.*, 232(2): 293-300 (2005).

\* cited by examiner

METHOD FOR CULTURE OF STEM CELL

TECHNICAL FIELD

The present invention relates to a method of culturing stem cells. Specifically, the present invention relates to a method of inducing differentiation of stem cells comprising combining quick re-aggregation and three-dimensional suspension culture in performing stem cell aggregate culture, and to a cell culture obtained by the method, and the like.

BACKGROUND ART

To date, some culturing methods for inducing differentiation of nerves from a pluripotent stem cell such as an ES cell have been known, including those reported by the present inventors (Non-Patent Documents 1-3, Patent Documents 1 and 2); there are high expectations for ES cell-derived nerve cells (e.g., dopamine nerve cells and the like) as a source of graft cells for cell transplantation therapy in regenerative medicine for intractable neurologic diseases. To this end, disease-related nerve cells that are present in the brain must be produced accurately; however, because an extremely large number of kinds of nerve cells are present in the brain, there are still many types of nerve cells and brain tissues for which efficient in vitro differentiation has been unsuccessful.

The cerebrum, particularly cerebral cortex, is the center of higher brain functions; a disorder thereof causes serious motor, mental, and cognitive disorders. For example, Alzheimer's disease, cerebral infarction, epilepsy, motor neuron disease (ALS) and the like can be mentioned. For the treatment of cerebral disorders, etiologic research, drug discovery research, cell transplantation therapy research and the like have been conducted so far, but it is extremely difficult to obtain human cerebral tissue for the sake of these researches. Although it has recently become possible to induce differentiation of an embryonic stem cell into cortical progenitor cells (see Non-Patent Document 4), it has been difficult to control the selective induction of differentiation from those progenitor cells to particular cerebral cortical neurons.

The present inventors showed that dispersion suspension culture using a serum-free medium (the SFEB method) is effective as a method of inducing differentiation of a pluripotent stem cell such as animal or human ES cell into nerves (see Non-Patent Documents 3 and 4 and Patent Document 1). This method enables efficient induction of differentiation into nerve cells and sensory cells of the forebrain, particularly of the cerebrum and the neural retina. The present inventors also succeeded in inducing differentiation into brainstem tissues such as the cerebellum by adding growth factors such as Wnt to the medium.

However, an analytical study with mouse embryonic stem cells revealed that when the SFEB method was applied, about 30% of the cells differentiated into cerebral nerve cells, but the remaining majority occurred as a mixture of other kinds of nerve cells. Additionally, cerebral cortex cells accounted for only about 40% of the differentiation-induced cerebral nerve cells; the induction efficiency was not so high. Furthermore, the majority of the cerebral tissues induced by a conventional method such as the SFEB method failed to have a clear morphology of cortical tissue, mostly forming disarrayed cell masses. Additionally, the conventional SFEB method does not enable efficient induction of differentiation of the tissue of the rostral diencephalon, which develops on the most rostral side of the central nervous system, particularly of the hypothalamus, from an ES cell.

PRIOR ART DOCUMENTS

Patent Documents

Patent Document 1: Pamphlet for WO2005/123902
Patent Document 2: JP-A-2008-99662

Non-Patent Documents

Non-Patent Document 1: Watanabe, K., Ueno, M., Kamiya, D., Nishiyama, A., Matsumura, M., Wataya, T., Takahashi, J. B., Nishikawa, S., Nishikawa, Muguruma, K. and Sasai, Y. (2007) A ROCK inhibitor permits survival of dissociated human embryonic stem cells. Nature Biotechnology 25, 681-686

Non-Patent Document 2: Su, H.-L., Muguruma, K., Kengaku, M., Matsuo-Takasaki, M., Watanabe, K., and Sasai, Y. (2006) Generation of Cerebellar Neuron Precursors from Embryonic Stem Cells. Developmental Biology 290, 287-296

Non-Patent Document 3: Ikeda, H., Watanabe, K., Mizuseki, K., Haraguchi, T., Miyoshi, H., Kamiya, D., Honda, Y., Sasai, N., Yoshimura, N., Takahashi, M. and Sasai, Y. (2005) Generation of Rx+/Pax6+ neural retinal precursors from embryonic stem cells. Proc. Natl. Acad. Sci. USA 102, 11331-11336

Non-Patent Document 4: Watanabe, K., Kamiya, D., Nishiyama, A., Katayama, T., Nozaki, S., Kawasaki, H., Mizuseki, K., Watanabe, Y., and Sasai, Y. (2005) Directed differentiation of telencephalic precursors from embryonic stem cells. Nature Neurosci. 8, 288-296

SUMMARY OF THE INVENTION

Problems to be Solved by the Invention

It is an object of the present invention to develop a highly practical method that enables the induction of differentiation of a pluripotent stem cell such as an ES cell, particularly the induction of differentiation into cerebral cortical tissue, or the selective induction of differentiation into neurons of the diencephalon, particularly of the hypothalamus.

Means of Solving the Problems

The present inventors extensively investigated differentiation induction conditions for embryonic stem cells in the absence of serum, based on the hypothesis that formation of an epithelium-like structure is essential to the induction of differentiation into cerebral cortical cells because nerve tissue has an epithelial structure called nerve epithelium when it is in the stage of progenitor cells, and also because its formation is essential to the efficient differentiation and histogenesis of cerebral cortex, as an explanation for the low efficiency of induction of differentiation of cerebral nerve cells, particularly cerebral cortical cells, by the SFEB method. As a result, the present inventors found that nerve cells, particularly cerebral cortical cells, can be differentiation-induced from an ES cell with high efficiency by forming homogenous aggregates of stem cells in a serum-free medium.

Furthermore, in the present invention, the present inventors clarified the reason why it had been difficult to induce the differentiation of the rostral part, including the hypothalamus, of diencephalon tissue from an ES cell was that inhibitory substances were contained in the serum-free medium, and succeeded in efficiently inducing the differentiation of hypothalamic nerve cells by developing a culture method to avoid the difficulty. Serum-free media are generally often supplemented with several growth factors (Wnt, TGFβ, BMP, retinoic acid, FGF, lipid-rich albumin and the like) as serum substitutes. However, it was found that all of these growth factors acted as inhibitors on the differentiation of the rostral part, including the hypothalamus, of diencephalon tissue. Moreover, the present inventors demonstrated that insulin, which is most frequently added to serum-free media, also strongly inhibits the differentiation of the rostral part, including the hypothalamus, of diencephalon tissue, and that this inhibition is caused by the activation of an intracellular enzyme (phosphorylase) called Akt, which is a downstream signal of insulin.

By inducing the differentiation of a mouse ES cell using an insulin-free chemically synthesized medium on the basis of these findings to differentiate hypothalamic progenitor cells, and maturing them, it has become possible to differentiate hypothalamic endocrine neurons such as vasopressin-producing cells. Furthermore, in differentiation culture of human ES cells, the survival is poor with an insulin-deprived medium, but it has become possible to induce the differentiation of hypothalamic nerve tissue by using an Akt inhibitor in combination with an insulin-containing chemically synthesized medium.

The present inventors conducted further investigations based on these findings, and have developed the present invention.

Accordingly, the present invention provides the following:

[1] A method of inducing differentiation of a stem cell, comprising a step for forming homogenous aggregates of stem cells in a serum-free medium.
[2] The method described in [1] above, further comprising a step for suspension-culturing the homogenous aggregates of stem cells in a serum-free medium.
[3] The method described in [1] or [2] above, wherein the stem cell is a pluripotent stem cell.
[4] The method described in [3] above, wherein the stem cell is an embryonic stem cell.
[5] The method described in any one of [2] to [4] above, wherein the suspension culture is performed for 60 hours to 350 hours.
[6] The method described in any one of [1] to [5] above, further comprising a step for cultivation in the presence of a Nodal signal inhibitor and/or a Wnt signal inhibitor.
[7] The method described in [6] above, wherein the Nodal signal inhibitor is Lefty-1.
[8] The method described in [6] above, wherein the Wnt signal inhibitor is Dkk1.
[9] The method described in any one of [1] to [8], further comprising a step for cultivation in the presence of a Nodal signal inhibitor.
[10] The method described in [9] above, wherein the Notch signal inhibitor is DAPT.
[11] The method described in any one of [1] to [8] above, further comprising a step for cultivation in the presence of a secreted pattern formation factor.
[12] The method described in any one of [1] to [11] above, which is a method of inducing differentiation into nervous system cells.
[13] The method described in any one of [1] to [8] above, which is a method of inducing differentiation into cerebral progenitor cells.
[14] The method described in any one of [1] to [8], which is a method of inducing differentiation into cerebral cortex progenitor cells.
[15] The method described in any one of [1] to [11] above, which is a method of inducing differentiation into cerebral cortical nerve cells.
[16] The method described in any one of [1] to [11] above, which is a method of selectively inducing differentiation into layer-specific neurons.
[17] The method described in any one of [1] to [7] above, which is a method of inducing differentiation into Cajal-Retzius cells.
[18] The method described in any one of [1] to [5] and [8] to [11] above, which is a method of inducing differentiation into caudal cerebral cortical nerve cells.
[19] The method described in [18] above, wherein the cultivation is performed in the presence of an Fgf signal inhibitor.
[20] The method described in [19] above, wherein the Fgf signal inhibitor is an Fgf receptor inhibitor.
[21] The method described in any one of [1] to [5] and [8] to [11] above, which is a method of inducing differentiation into rostral cerebral cortical nerve cells.
[22] The method described in [21] above, wherein the rostral cerebral cortical nerve cells are olfactory bulb neurons.
[23] The method described in [21] or [22] above, wherein the cultivation is performed in the presence of an Fgf signal promoter.
[24] The method described in [23] above, wherein the Fgf signal promoter is Fgf or an agonist thereof.
[25] The method described in any one of [1] to [5] and [8] to [11] above, which is a method of inducing differentiation into hippocampal nerve cells.
[26] The method described in [23] above, wherein the cultivation is performed in the presence of Wnt or in the presence of BMP, or in the presence of both.
[27] The method described in any one of [1] to [5] and [8] to [11] above, which is a method of inducing differentiation into cerebral basal nuclear nerve cells.
[28] The method described in [27] above, wherein the cultivation is performed in the presence of an Shh signal promoter.
[29] The method described in [28] above, wherein the Shh signal promoter is Shh.
[30] A method of producing hypothalamic neuron progenitor cells, comprising culturing pluripotent stem cells as suspended aggregates in a serum-free medium that substantially does not contain a Nodal signal promoter, a Wnt signal promoter, an FGF signal promoter, a BMP signal promoter, retinoic acid and an insulin, and isolating hypothalamic neuron progenitor cells from the culture.
[31] The method described in [2] above, wherein the serum-free medium does not substantially contain a Nodal signal promoter, a Wnt signal promoter, an FGF signal promoter, a BMP signal promoter, retinoic acid and insulin.
[32] The method described in [30] or [31] above, wherein the serum-free medium contains selenitic acid or a salt thereof.
[33] The method described in [30] or [31] above, wherein the serum-free medium contains an Shh signal promoter.
[34] The method described in [30] or [31] above, wherein the serum-free medium substantially does not contain an Shh signal promoter.
[35] The method described in [33] above, wherein the progenitor cells that can be obtained are ventral hypothalamic neuron progenitor cells.

[36] The method described in [33] above, wherein the progenitor cells that can be obtained have the potential for differentiating into medial ventral nuclear neurons, type A12 dopamine neurons, arcuate nuclear neurons or orexin-positive neurons.
[37] The method described in [34] above, wherein the progenitor cells that can be obtained are dorsal hypothalamic neuron progenitor cells.
[38] The method described in [34] above, wherein the progenitor cells that can be obtained have the potential for differentiating into vasopressin-producing endocrine cells.
[39] The method described in [30] or [31] above, wherein the cultivation is performed for at least 7 days.
[40] A method of producing hypothalamic neuron progenitor cells, comprising culturing pluripotent stem cells as suspended aggregates in a serum-free medium that contains at least one inhibitor selected from the group consisting of PI3K inhibitors and Akt inhibitors and insulins, and that substantially does not contain a Nodal signal promoter, a Wnt signal promoter, an FGF signal promoter, a BMP signal promoter and retinoic acid, and isolating hypothalamic neuron progenitor cells from the culture.
[41] The method described in [2] above, wherein the serum-free medium contains at least one inhibitor selected from the group consisting of PI3K inhibitors and Akt inhibitors and an insulin, and does not substantially contain a Nodal signal promoter, a Wnt signal promoter, an FGF signal promoter, a BMP signal promoter and retinoic acid.
[42] The method described in [40] or [41] above, wherein the serum-free medium further contains a ROCK inhibitor.
[43] The method described in [40] or [41] above, wherein the pluripotent stem cells are primate pluripotent stem cells.
[44] A cell culture obtained by the method described in any one of [1] to [43] above.
[45] A method of producing a steric structure of a brain tissue in vitro, comprising a step for forming homogenous aggregate masses of stem cells in a serum-free medium.
[46] The method described in [45] above, wherein the brain tissue is a cerebral cortical tissue.
[47] The method described in [46] above, wherein the cerebral cortical tissue is accompanied by laminer for Illation.
[48] The method described in [45] above, wherein the serum-free medium contains an extracellular matrix component.
[49] A culture product obtained by the method described in any one of [45] to [48] above.
[50] A method of forming a cerebral cortical nerve network in vitro, comprising a step for forming homogenous aggregate masses of stem cells in a serum-free medium.
[51] The method described in [50] above, wherein the cerebral cortical nerve network is accompanied by synchronized spontaneous firing.
[52] A culture product obtained by the method described in [50] or [51] above.
[53] A screening method for a test substance, comprising using the cell culture described in [44] above, the culture product described in [49] above or the culture product described in [52] above.

Effect of the Invention

According to the present invention, it is possible to efficiently induce the differentiation of a stem cell into cerebral cortex progenitor cells. A method of the present invention also enables efficient induction of the differentiation of nervous system cells, particularly cerebral cortical cells, that has been difficult to achieve by the conventional method of differentiation induction. Therefore, a method of the present invention is particularly useful from the viewpoint of applying cytotherapy for diseases due to an abnormality of cerebral tissue.

According to a method of the present invention, it is possible to selectively induce the differentiation of layer-specific neurons. It is also possible to efficiently induce the differentiation of not only cerebral cortical cells, but also other forebrain nerve cells such as hippocampal nerve cells and cerebral basal nuclear nerve cells.

Using a method of the present invention, it is possible to efficiently produce neurons of the diencephalon, particularly of the hypothalamis, and progenitor cells thereof, from a pluripotent stem cell such as an ES cell. The hypothalamus is the responsible site for medically important diseases, including endocrine abnormalities such as central diabetes insipidus, eating disorders (apastia/bulimia), sleep disorders and the like; production of these tissues from a pluripotent stem cell such as an ES cell in vitro would be helpful not only in regenerative medicine, but also in drug discovery and safety studies for endocrine abnormalities, eating disorders, sleep disorders and the like.

According to a method of the present invention, it is possible to form a cerebral cortical nerve network in vitro, so that applying the method of the present invention is useful in that drug discovery and toxicity studies of synapse function promoters, epilepsy remedies and the like can be performed effectively.

Furthermore, the present invention also makes it possible to produce a steric structure of a cerebral cortical tissue having a laminar structure in vitro. Therefore, a method of the present invention is also highly useful in providing "tissue materials" for use in regenerative medicine, and in drug discovery and toxicity studies of the above-described pharmaceuticals and the like.

The present invention is also useful in that stem cells can be differentiation-induced without using an animal-derived cell as an inductor, so that the risk in the transplantation of cells obtained by stem cell culture can be reduced to the risk levels in allotransplantation.

BRIEF DESCRIPTION OF THE DRAWINGS

FIGS. 1A-O show that aggregates of ES cells obtained by the SFEBq method differentiate into homogenous nerve cells having an epithelium-like structure. FIG. 1A is a schematic diagram of a culture method that induces differentiation into homozygous nerve cells having an epithelium-like structure (SFEBq method). FIGS. 1B-O are images confirming the presence of an epithelium-like structure with polarity in the aggregates by the expression of N-cadherin, CD-133, laminin and the like (B to G), electron microscopic observation of the morphology of tight junction (H, parenthesized) and adherence junction (I, parenthesized), the formation of a rosette (J, K, dotted line indicates a rosette) and the expression of polarity markers (L to O, dotted line indicates a rosette, asterisk indicates a lumen).

FIGS. 2A-F show that aggregates of ES cells obtained by the SFEBq method differentiate into cerebrum-specific neurons via cerebral cortex progenitor cells. FIGS. 2A and 2C-F demonstrate the expression of the glutamatergic neuron (abundantly present in cerebral cortex) marker VGluT1 (A), the expression of Telencephalin (C), the expression of CamKII and Ctip2 (D), the expression of GluR1 and Ctip2 (E), and the expression of Bf1, Ctip2, Map2, Brn2 and Tbr1 (F). FIG. 2B is a graph demonstrating the percentage of cells (y-axis) which were positive for the cerebral cortex-specific marker Emx1 and positive for the glutamatergic neuron marker VGluT1 (x-axis).

FIGS. 3-1(A)-(H) and (3-1(J) show that aggregates of ES cells obtained by the SFEBq method form a nerve network of cerebral neurons. FIG. 3-1(A) s a schematic diagram of a culture method. FIGS. 3-1(B) and 3-1(C) show the results of $Ca^{++}$ imaging performed at room temperature using an artificial cerebrospinal fluid, wherein cells exhibited repeatedly observable $Ca^{++}$ elevations synchronized or not synchronized with surrounding cells. FIGS. 3-1(D) through 3-1F illustrate that $Ca^{++}$ elevations were enhanced by administration of glutamine (D) and inhibited by the addition of tetrodotoxin, which causes a blockade of nerve action potentials (E to F). In FIGS. 3-1(G) and 3-1(H), repeated activities of $Ca^{++}$ elevations synchronized at a high transmission speed (1 mm/second or more) over a long distance of 1 mm ($Ca^{++}$ oscillation) were observed. In FIGS. 3-1(H), codes A to E indicate individual cells.

FIG. 3-2(I) contains an image and a raster plot showing that aggregates of ES cells obtained by the SFEBq method form a nerve network of cerebral neurons. $Ca^{++}$ imaging was performed at room temperature using an artificial cerebrospinal fluid. Numerical figures indicate individual cells.

FIG. 4A is a schematic diagram of a culture method. FIGS. 4B and 4C are images demonstrating that a large number of Venus-positive nerve cells invaded cerebral cortical tissue from the Venus-positive cell mass. FIG. 4D is an image demonstrating that neurons that are morphologically similar to cerebral pyramidal cells differentiated from the dispersed and transplanted Venus-positive cells in the in vivo transplantation to the vicinity of the motor area of the cerebral cortex of the neonatal mouse. FIG. 4E (codes O to U; Cx indicates cortex) are images demonstrating that from the cells that were transplanted in the form of the cell mass, axonal projections to a broad range of brain tissues were noted; in particular, axonal projections from cerebral cortical neurons were prevalent; in the thalamus, striatum, cerebral peduncle, and pontine nucleus, many Venus-positive projections were confirmed.

FIGS. 5A-C demonstrate the time frame for cells expression in culture. Cells that expressed Reelin, which is specific for the Cajal-Retzius cells of the 1st cerebral layer, emerged from day 7 of SFEBq culture (A). Tbr1/Bf1-positive cells specific for the 6th cerebral layer were also noted from day 7 (A). Citp2-positive cells specific for the 5th cerebral layer significantly emerged from days 9-10 (B), and Brn2-positive neurons specific for the 2nd-3rd cerebral layers were significantly observed on days 11-12 (C). This order (A) agrees with the order of development of these cerebral layer-specific neurons in the developmental process. Their correlation was also confirmed by the birth-date analytical method based on the BrdU pulse label; it was confirmed that the cells departed from the cell cycle in the order of the 1st layer, 6th layer, 5th layer, and 2nd-3rd layers (D to G). FIG. 5H demonstrates the percentages of $BrdU^+$ cells expressing specific marker genes.

FIG. 6A is a schematic diagram of a culture method that induces differentiation into particular layer-specific cerebral cortical neurons via cerebral cortex progenitor cells. FIG. 6B demonstrates the percentage of $Reelin^+$ cells after the DAPT treatment. FIG. 6C demonstrates the percentage of $Ctip2^+$ cells after the DAFT treatment.

FIGS. 7-1(A)-(E) and (G)-(U) show that aggregates of ES cells obtained by the SFEBq method differentiate into site-specific cerebral cortical neurons via cerebral cortex progenitor cells. FIG. 7-1(A) is a schematic diagram of a culture method that induces differentiation into site-specific cerebral cortical neurons via cerebral cortex progenitor cells. FIG. 7-1(B) demonstrates the percentage of $Coup-TF1^+$ cells after addition of FGF8/FGFR3-Fc. FIGS. 7-1(C) and 7-1(G) demonstrate the Coup-TF1 (C) and Bf1::Venus (G) expression in control cells. FIGS. 7-1(D) and 7-1(H) demonstrate the Coup-TF1 (D) and Bf1::Venus (H) expression in cells FGF8-treated cells. FIGS. 7-1(E) and 7-1(I) demonstrate the Coup-TF1 (E) and Bf1::Venus (I) expression in FGFR3-Fc-treated cells. FIGS. 7-1 (J-N) demonstrate that following 12 days of culture, significant differentiation of neurons of the olfactory bulb, which is one of the rostral cerebral tissues, was observed only in the Fgf 8 addition group (the arrowheads in M and N indicate cells that expressed TBx21.). FIGS. 7-1(O-R) demonstrate that induction of the expression of Otx2 and Lmx1a, which are site-specific markers of the hem area (perihippocampal tissue) present in the most caudal and dorsal part of the cerebrum, was observed in 2-30% of the cells in the Wnt3a addition group. FIGS. 7-1 (O) and 7-1(S) demonstrate that differentiation of choroidal tissue present in the most dorsal part of the cerebrum (TTR-positive), in addition to the expression of Otx2 and Lmx1a, was noted in the the BMP4 addition group. FIGS. 7-1(T) and 7-1(U) demonstrate that the expression of Otx2 and Lmx1a was noted in more than 50% of the cells, and the expression of TTR was noted in 20% of the cells in the Wnt3a+BMP4 addition group.

FIG. 7-2(V) is a drawing showing that aggregates of ES cells obtained by the SFEBq method differentiate into site-specific cerebral cortical neurons via cerebral cortex progenitor cells. By combining the SFEBq method and a Wnt signal and a BMP signal, induction of differentiation into the most caudal and dorsal tissue of the cerebrum is also possible from an ES cell.

FIG. 9A is a schematic diagram of a culture method that induces differentiation into cerebral cortical neurons. Figs. B-D demonstrate that in more than 90% of the aggregate masses, Bf1/Emx1-positive cerebral cortex type nerve epithelium was present as a continuous tissue, and the nerve epithelium tissue had a polarity wherein the inside thereof was the apical side. Figs. E-J demonstrate that, as with mouse ES cell-derived cerebral tissue, production of layer-specific cerebral neurons was noted, and, in addition, a similar laminar arrangement was noted in the neuron clusters in the cell aggregate mass. Outside of the Tbr1-, Ctip2-positive layers, there were Reelin-positive cells corresponding to the 1st cerebral layer (E to J).

FIGS. 11A-B show that aggregates of human ES cells obtained by the SFEBq method differentiate into anterior or posterior cerebral cortical neurons. FIG. 11A shows that, in the control without the addition of Fgf 8, 80% of the Bf1-positive cells were of the CoupTf1-positive posterior type.

BEST MODE FOR CARRYING OUT THE INVENTION

Figure 1:
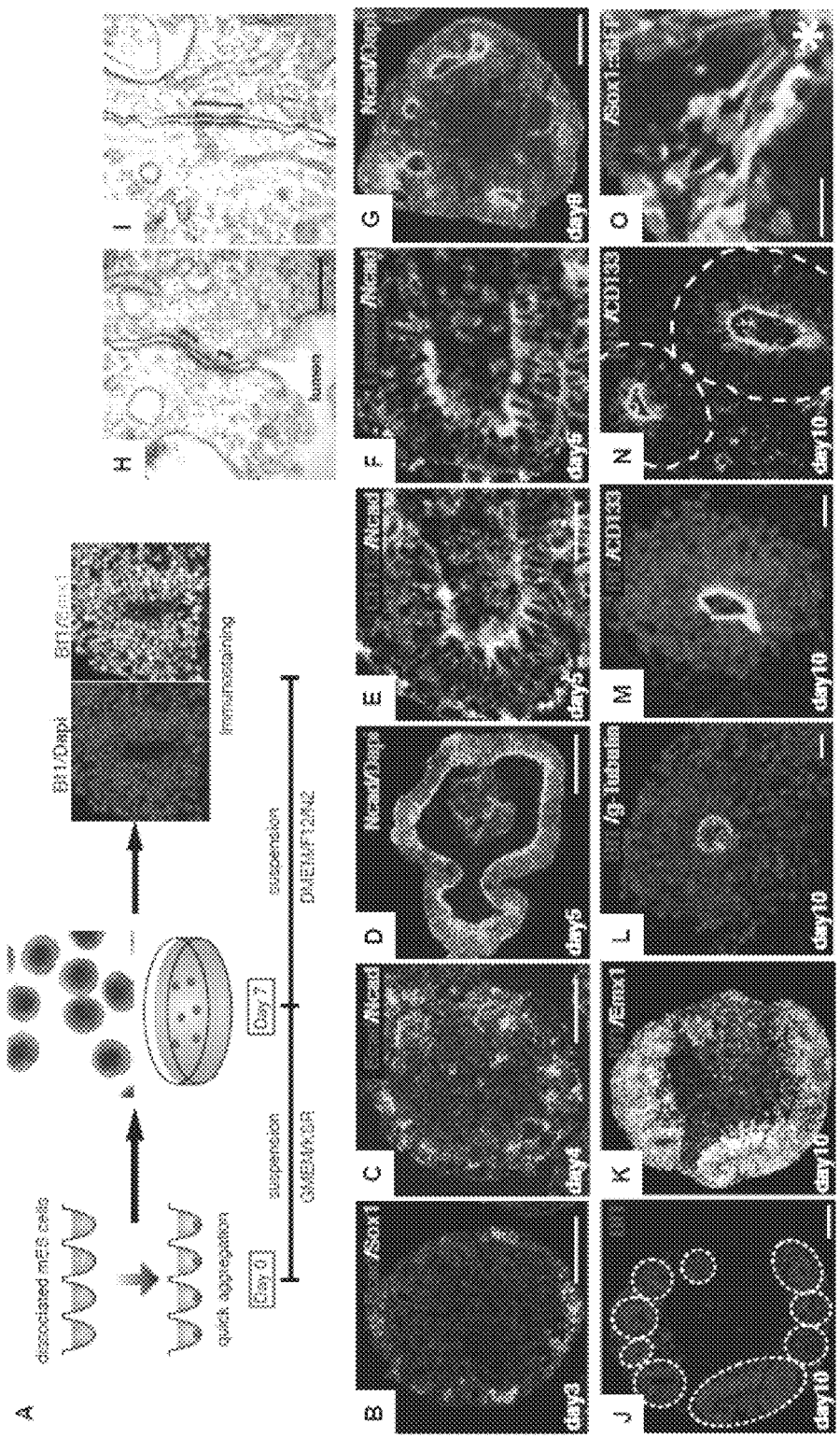

The present invention provides a method of differentiation culture of a stem cell, comprising a step for forming homogenous aggregate masses of stem cells in a serum-free medium. The present invention also provides a method of producing hypothalamic neuron progenitor cells, comprising culturing pluripotent stem cells as suspended aggregates in a serum-free medium that substantially does not contain growth factors such as Nodal signal promoters, Wnt signal promoters, FGF signal promoters, BMP signal promoters, and retinoic acid, and insulins, and isolating hypothalamic neuron progenitor cells from the culture.

The present invention is hereinafter described in detail.
(1) Stem Cells

"A stem cell" refers to a cell capable of retaining a constant potential for differentiation even after undergoing cell division. Examples of stem cells include embryonic stem cells (ES cells) with pluripotency derived from a fertilized egg or a clone embryo, somatic stem cells and pluripotent stem cells that are present in tissues in a living organism, hepatic stem cells, dermal stem cells, and reproductive stem cells that serve as the bases for respective tissues, pluripotent stem cells derived from a reproductive stem cell, pluripotent stem cells derived from a somatic cell that are obtained by nuclear reprogramming, and the like.

In particular, "a pluripotent stem cell" refers to a stem cell that permits cultivation in vitro, and having the potential for differentiating into all cells, but the placenta, constituting the body (tissues derived from the three primary germ layers of the embryo (ectoderm, mesoderm, endoderm)) (pluripotency); embryonic stem cells are also included therein. "A pluripotent stem cell" is obtained from a fertilized egg, a clone embryo, a reproductive stem cell, or a stem cell in tissue. Also included are cells having differentiation pluripotency similar to that of embryonic stem cells, conferred artificially by transferring several different genes to a somatic cell (also referred to as induced pluripotent stem cells). Pluripotent stem cells can be prepared by a method known per se. Available methods include, for example, methods described in Cell 131(5), pp. 861-872, Cell 126(4), pp. 663-676 and elsewhere.

As stem cells, for example, cells derived from a warm-blooded animal, preferably from a mammal, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees.

Examples of stem cells that are specifically used in a method of the present invention include embryonic stem cells of a mammal or the like established by culturing a pre-implantation early embryo (hereinafter, abbreviated as "embryonic stem cells I"), embryonic stem cells established by culturing an early embryo prepared by nuclear-transplanting the nucleus of a somatic cell (hereinafter, abbreviated as "embryonic stem cells II"), induced pluripotent stem cells (iPS cells) established by transferring several different transcriptional factors to a somatic cell, and pluripotent stem cells prepared by modifying a gene on a chromosome of embryonic stem cells I, embryonic stem cells II or iPS cells using a gene engineering technique (hereinafter, abbreviated as "modified pluripotent stem cells").

More specifically, embryonic stem cells I include embryonic stem cells established from an inner cell mass that constitutes an early embryo, EG cells established from a primordial germ cell, cells isolated from a cell population possessing the pluripotency of pre-implantation early embryos (for example, primordial ectoderm), cells obtained by culturing these cells, and the like.

Embryonic stem cells I can be prepared by culturing a pre-implantation early embryo according to a method described in the literature (Manipulating the Mouse Embryo A Laboratory Manual, Second Edition, Cold Spring Harbor Laboratory Press (1994)).

Embryonic stem cells II can be prepared using, for example, methods reported by Wilmut et al. (Nature, 385, 810 (1997)), Cibelli et al. (Science, 280, 1256 (1998)), Akira Iritani et al. (Protein, Nucleic Acid and Enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)) and others, for example, as described below.

By extracting the nucleus of a mammalian cell and then reprogramming the nucleus (an operation to return the nucleus to a state to resume development), initiating development using a method involving injection into an enucleated unfertilized egg of a mammal, and culturing the egg that has started development, an egg that has the nucleus of another somatic cell, and has begun normal development, is obtained.

A plurality of methods of reprogramming the nucleus of a somatic cell are known. For example, the nucleus can be reprogrammed by changing the medium used to culture the nucleus donor cell from a medium containing 5 to 30%, preferably 10%, of fetal calf serum (for example, M2 medium) to an oligotrophic medium containing 0 to 1%, preferably 0.5%, of fetal calf serum, and culturing the cell for 3 to 10 days, preferably 5 days, to induce the cell cycle into a resting phase state (G0 stage or G1 stage).

The nucleus can also be reprogrammed by injecting the nucleus of the nucleus donor cell into an enucleated unfertilized egg of a mammal of the same species, and culturing the cell for several hours, preferably for about 1 to 6 hours.

The reprogrammed nucleus is able to begin development in the enucleated unfertilized egg. A plurality of methods of allowing the reprogrammed nucleus to begin development in the enucleated unfertilized egg are known. By transplanting a nucleus reprogrammed by inducing the cell cycle to a resting phase state (phase G0 or phase G1) into an enucleated unfertilized egg of a mammal of the same species by the electrofusion method and the like, the egg can be activated and allowed to begin development.

A nucleus reprogrammed by injecting the nucleus into an enucleated unfertilized egg of a mammal of the same species is transplanted back to an enucleated unfertilized egg of a mammal of the same species by a method using a micromanipulator or the like, and stimulated with an egg activator (for example, strontium and the like), and thereafter treated with an inhibitor of cell division (for example, cytochalasin B and the like) to suppress the release of the second polar body, whereby development can be initiated. This method is suitable when the mammal is, for example, a mouse or the like.

Provided that an egg once began to develop is obtained, embryonic stem cells can be acquired using publicly known methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

An iPS cell can be produced by transferring Oct3/4, Sox2 and Klf4 (c-Myc or n-Myc further added as required) to a somatic cell (for example, fibroblast, dermal cell and the like) (Cell, 126: p. 663-676, 2006; Nature, 448: p. 313-317, 2007; Nat Biotechnol, 26: p. 101-106, 2008; Cell 131:861-872, 2007).

Modified pluripotent stem cells can be prepared by using, for example, homologous recombination technology. Examples of the gene on the chromosome to be modified in preparing modified pluripotent stem cells, histocompatibility antigen genes, genes related to diseases based on disorders of nervous system cells, and the like. A modification of the target gene on the chromosome can be performed using methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

Specifically, for example, a genomic gene of a target gene to be modified (for example, histocompatibility antigen genes, disease-related genes and the like) is isolated, and a target vector for homologous recombination of the target gene is prepared using the genomic gene isolated. By transferring the target vector prepared to an embryonic stem cell, and selecting cells undergoing homologous recombination between the target gene and the target vector, stem cells having a modified gene on the chromosome can be prepared.

Methods of isolating a genomic gene of a target gene include publicly known methods described in Molecular Cloning, A Laboratory Manual, Second Edition, Cold Spring Harbor Laboratory Press (1989), Current Protocols in Molecular Biology, John Wiley & Sons (1987-1997) and elsewhere. A genomic gene of a target gene can also be isolated by using a genomic DNA library screening system (produced by Genome Systems), Universal GenomeWalker™ Kits (produced by CLONTECH) and the like.

Preparation of a target vector for homologous recombination of a target gene and efficient sorting of a homologous recombinant can be achieved by a method described in Gene Targeting, A Practical Approach, IRL Press at Oxford University Press (1993); Biomanual Series 8 Gene Targeting, Preparation of Mutant Mice Using ES Cells, Yodosha (1995) and elsewhere. The target vector used may be any one of the replacement type and the insertion type; useful methods of sorting include positive selection, promoter selection, negative selection, poly A selection and the like.

Available methods of selecting a desired homologous recombinant from among the sorted cell lines include Southern hybridization, PCR and the like, for genomic DNA.

Stem cells are available from specified organizations, and commercial products may be purchased. For example, the human embryonic stem cells KhES-1, KhES-2 and KhES-3 are available from the Institute for Frontier Medical Sciences, Kyoto University. Examples of mouse embryonic stem cells include EB5 cells and the like.

Stem cells can be cultured for maintenance by a method known per se. For example, stem cells can be maintained by cultivation without feeder cells with the addition of fetal calf serum (FCS), Knockout™ Serum Replacement (KSR), and LIF.

(2) Nervous System Cells that can be Differentiation-Induced by a Method of the Present Invention By a method of the present invention, it is possible to obtain differentiated cells from a stem cell, preferably from a pluripotent stem cell such as an embryonic stem cell. Although the cells differentiation-induced from a stem cell by a method of the present invention are not particularly limited, and may be any of endodermal cells, mesodermal cells, and ectodermal cells, the cells are preferably ectodermal cells, more preferably nervous system cells. The identity of the cells obtained by a method of the present invention can be confirmed by a method known per se, for example, by the expression of a cell marker.

Examples of markers of nervous system cells include, but are not limited to, NCAM, TuJ1, tyrosine hydroxylase (TH), serotonin, nestin, MAP2, MAP2ab, NeuN, GABA, glutamates, ChAT, Sox1, Bf1, Emx1, VGluT1, Pax, Nkx, Gsh, Telencephalin, GluR1, CamKII, Ctip2, Tbr1, Reelin, Brn2 and the like. Hereinafter, to exemplify ectodermal cells that can be differentiation-induced by a method of the present invention, nervous system cells are described in detail.

Examples of nervous system cells obtained by a method of the present invention include nerve stem cells, nerve cells, cells of the neural tube, cells of the neural crest and the like.

(2-1) Nerve Stem Cells

A nerve stem cell refers to a cell having both the potential for differentiation into nerve cells, astrocytes and oligodendrocytes and the potential for autoreproduction. It also has a function to supply nerve cells, astrocytes and oligodendrocytes in the brain.

Available methods of confirming the identity of cells as nerve stem cells include a method wherein the cells are actually transplanted to a brain and the differentiating potential thereof is confirmed, a method wherein the nerve stem cells are differentiation-induced to nerve cells, astrocytes, or oligodendrocytes in vitro and the identity is confirmed, and the like (Mol. Cell. Neuroscience, 8, 389(1997); Science, 283, 534(1999)). Nerve stem cells having these functions are stainable with an anti-nestin antibody that recognizes the cytoskeletal protein nestin, which is a marker whose expression has been confirmed in nerve progenitor cells (Science, 276, 66(1997)). Therefore, it is also possible to confirm the identity of the nerve stem cells by staining with an anti-nestin antibody.

(2-2) Nerve Cells

A nerve cell (neuron) refers to a cell that has functions to receive a stimulus from other nerve cells or stimulus receptor cells and transmit the stimulation to other nerve cells, muscle or glandular cells. Nerve cells can be classified on the basis of differences in the neurotransmitter produced by the nerve cells, for example, on the basis of differences in the secreted neurotransmitter and the like. Examples of nerve cells classified by these neurotransmitters include dopamine-secreting nerve cells, acetylcholine-secreting nerve cells, serotonin-secreting nerve cells, noradrenaline-secreting nerve cells, adrenaline-secreting nerve cells, glutamate-secreting nerve cells and the like. Dopamine-secreting nerve cells, noradrenaline-secreting nerve cells and adrenaline-secreting nerve cells are collectively referred to as catecholamine-secreting nerve cells.

Alternatively, the nerve cells, particularly cerebral nerve cells, obtained by a method of the present invention can be characterized by cell markers. The nerve cells that can be obtained by the method of the present invention are positive for Sox1 at a high frequency, for example, at a frequency of about 80% or more, preferably about 80 to 90%. Also, the nerve cells that can be obtained by the method of the present invention are more preferably positive for the cerebral nerve cell marker described below.

From another viewpoint, nerve cells can be classified according to differences in the site where the nerve cells are present. As examples of these nerve cells classified according to the site where they exist, forebrain nerve cells, midbrain nerve cells, cerebellar nerve cells, metencephalic nerve cells, spinal nerve cells and the like can be mentioned. A method of the present invention makes it possible to differentiation-induce these optionally chosen nerve cells, and particularly enables the efficient differentiation induction into forebrain nerve cells, preferably cerebral nerve cells, more preferably cerebral cortical nerve cells (cerebral dorsal cells). A method of the present invention also makes it possible to differentiation-induce preferably Cajal-Retzius cells, hippocampal nerve cells efficiently. Described in detail below are forebrain nerve cells.

(2-2-1) Forebrain Nerve Cells

According to a method of the present invention, as nerve cells, forebrain nerve cells, preferably cerebral nerve cells can be differentiation-induced more efficiently. A forebrain nerve cell refers to a nerve cell present in forebrain tissue (that is, the tissue comprising the cerebrum and the diencephalon) or a precursor cell destined to differentiate into a nerve cell present in forebrain tissue (e.g., cerebral progenitor cells).

Forebrain nerve cells can be classified into cerebral (endbrain) nerve cells and diencephalon nerve cells (for example, thalamic cells, hypothalamic cells and the like). Cerebral nerve cells can be further classified into dorsal cells (for example, cerebral cortical cells, Cajal-Retzius cells, hippocampal nerve cells and the like) and ventral cells (for example, cerebral basal nuclear cells and the like).

Whether or not the cell obtained by a method of the present invention is a forebrain nerve cell can be determined by a method known per se, for example, the expression of a forebrain nerve cell marker. Forebrain nerve cell markers include Otx1 (forebrain), Bf1 (cerebrum), Emx1 (cerebral dorsal), Gsh2 and Nkx2.1 (cerebral ventral) and the like.

According to one aspect of the present invention, a method of the present invention enables the efficient induction of differentiation of dorsal cerebral nerve cells out of cerebral nerve cells, and conversely enables the suppression of differentiation into ventral cerebral nerve cells. A dorsal cerebral nerve cell refers to a nerve cell present in dorsal cerebral tissue, or a precursor cell destined to differentiate into a nerve cell present in dorsal cerebral tissue (e.g., cerebral cortex progenitor cells). Dorsal cerebral tissues include, for example, cerebral cortex.

Whether or not the cells obtained by a method of the present invention are dorsal cerebral nerve cells can be determined by a method known per se, for example, the expression of a dorsal cerebral nerve marker. Dorsal cerebral nerve cells markers include, for example, cerebral cortical nerve cell marker (for example, Pax6, Emx1, Tbr1).

In another aspect of the present invention, a method of the present invention enables the efficient induction of differentiation of ventral cerebral nerve cells out of cerebral nerve cells, and conversely enables the suppression of differentiation into dorsal cerebral nerve cells. A ventral cerebral nerve cell refers to a nerve cell present in ventral cerebral tissue, or a precursor cell destined to differentiate into a nerve cell present in ventral cerebral tissue (e.g., cerebral basal nuclear progenitor cells). Ventral cerebral tissues include, for example, cerebral basal nuclei.

Whether or not the cells obtained by a method of the present invention are ventral cerebral nerve cells can be determined by a method known per se, for example, the expression of a ventral cerebral nerve cell marker. Ventral cerebral nerve cells markers include, for example, cerebral basal nuclear nerve cell markers (for example, Gsh2, Mash1, Nkx2.1, Noz1).

Alternatively, from another viewpoint, the forebrain nerve cell (particularly, cerebral nerve cells) obtained by a method of the present invention can be characterized by cell markers. The forebrain nerve cells obtained by the method of the present invention are positive for Bf1 (hereinafter described as "Bf1$^+$") at a high frequency, for example, at a frequency of about 50% or more, preferably about 70% or more, more preferably about 80% or more. By the conventional SDIA method, Bf1$^+$ cells could only been differentiation-induced from an embryonic stem cell at a frequency of about 1%, and even by the SFEB method, Bf1$^+$ cells could only been differentiation-induced from an embryonic stem cell at a frequency of about 10%, but a method of the present invention has made it possible to obtain Bf1$^+$ cells at a high frequency.

Of the Bf1$^+$ cells obtained by a method of the present invention, for example, about 20% or more, preferably about 20 to 80%, more preferably about 20 to 50%, can be positive for Gsh. Also, of the Bf1$^+$ cells obtained by the method of the present invention, for example, about 5% or more, preferably about 5 to 50%, more preferably about 5 to 20%, can be positive for Nkx2.1. Furthermore, of the Bf1$^+$ cells obtained by the method of the present invention, for example, about 10% or more, preferably about 10 to 90%, more preferably about 10 to 50%, can be positive for Pax.

Also, of the Bf1$^+$ cells obtained by the method of the present invention, for example, about 50% or more, preferably about 70% or more, more preferably about 80% or more, can be positive for Emx1. Furthermore, of the Bf1$^+$ cells obtained by the method of the present invention, for example, about 50% or more, preferably about 70% or more, more preferably about 80% or more, can be positive for VGluT1. Also, in some cells of the Bf1$^+$ cells obtained by the method of the present invention, the expression of Telencephalin, GluR1, CamKII, Ctip2, or Tbr1 can also be observed.

(3) Step for Forming Homogenous Aggregates of Stem Cells in Serum-Free Medium

The present invention provides a method of inducing the differentiation of a stem cell, comprising a step for forming homogenous aggregates of stem cells in a serum-free medium.

"Forming homogenous aggregates of stem cells" refers to forming qualitatively homogenous aggregates of stem cells by allowing "a given number of dispersed stem cells to aggregate quickly" in allowing stem cells to assemble and form aggregates of stem cells and culturing the aggregates (aggregate culture). The same refers particularly to promoting the epithelization of cells deriving from stem cells by allowing "the cells to aggregate quickly". Hence, as used herein, the term "to allow the cells to aggregate quickly" refers to forming with high reproducibility an epithelium-like structure in the cells produced by allowing stem cells to aggregate homogenously.

Any method may be employed to form homogenous aggregates of stem cells, as far as homogenous aggregates of stem cells are formed by allowing "the cells to aggregate quickly", and an epithelium-like structure of the cells produced from the stem cells is formed with high reproducibility; such methods include, for example, a method wherein cells are enclosed in small spaces using a plate with small wells (96-well plate), micropores or the like, a method wherein cells are aggregated by centrifugation for a short time using small centrifugal tubes, and the like.

Any culture vessel can be used to form aggregates, as far as it allows homogenous aggregates of stem cells to be formed by allowing "the cells to aggregate quickly"; those skilled in the art are able to determine the choice as appropriate. Such culture vessels include, for example, flasks, tissue culture flasks, dishes, Petri dishes, tissue culture dishes, multi-dishes, microplates, micro-well plates, micropores, multi-plates, multi-well plates, chamber slides, Petri dishes, tubes, trays, culturing bags, and roller bottles. From the viewpoint of forming homogenous aggregates, it is preferable that these culture vessels be non-cell-adhesive. Useful non-cell-adhesive culture vessels include culture vessels whose surfaces have not undergone an artificial treatment (e.g., coating treatment with an extracellular matrix and the like) for improving the cell adhesiveness.

A medium used to form aggregates can be prepared using a medium in use for animal cell culture as a basal medium. Any basal medium available for culturing animal cells can be used; examples include, but are not limited to, BME medium, BGJb medium, CMRL 1066 medium, Glasgow MEM medium, Improved MEM Zinc Option medium, IMDM medium, Medium 199 medium, Eagle's MEM medium, αMEM medium, DMEM medium, Ham's medium, RPMI 1640 medium, Fischer's medium, a mixed medium thereof and the like.

A serum-free medium used to form aggregates means a medium that does not contain an unadjusted or unpurified serum. Any such serum-free medium can be used in the present invention. However, to avoid the painstakingness in preparing the serum-free medium, a serum-free medium (GMEM or dMEM, 0.1 mM 2-mercaptoethanol, 0.1 mM non-essential amino acids Mix, 1 mM sodium pyruvate) supplemented with an appropriate amount (e.g., 1-20%) of commercially available KSR can be used.

The serum-free medium may contain a serum substitute. The serum substitute can be, for example, one containing as appropriate albumin, transferrin, fatty acids, collagen precursor, trace elements, 2-mercaptoethanol or 3'-thiolglycerol, or equivalents thereof and the like. This serum substitute can be prepared by, for example, a method described in WO98/30679. Also, to carry out a method of the present invention more conveniently, a commercially available serum substitute can be utilized. Examples of such commercially available serum substitutes include Chemically-defined Lipid Concentrated (produced by Gibco Company) and Glutamax (produced by Gibco Company).

The serum-free medium used for the suspension culture can also contain fatty acids or lipids, amino acids (for example, non-essential amino acids), vitamins, growth factors, cytokines, antioxidants, 2-mercaptoethanol, pyruvic acid, buffering agents, inorganic salts and the like.

The concentration of stem cells at the time of aggregate formation can be set as appropriate to allow aggregates of stem cells to be formed more homogenously and efficiently by those skilled in the art. The concentration of stem cells at the time of aggregate formation is not particularly limited as long as homogenous aggregates of stem cells can be formed; in case of using a 96-well microwell plate, for example, suspensions prepared to obtain a cell density of about $1 \times 10^3$ to about $5 \times 10^3$ cells, preferably about $2 \times 10^3$ to about $4 \times 10^3$ cells, per well, are added to the plate, and the plate is kept to stand to allow aggregates to be formed.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Although the time to the formation of aggregates can be determined as appropriate according to the stem cell used, as far as cells are allowed to aggregate quickly, it is desirable that the formation be performed as soon as possible to ensure the formation of homogenous aggregates. Conventionally, this formation of aggregates is performed over about 2 days (see, for example, Watanabe, K. et al., Nature Neurosci. 8, 288-296, Schuldiner M, Benvenisty N. Factors controlling human embryonic stem cell differentiation. Methods Enzymol. 2003; 365:446-461); in the present invention, by contrast, this time is shortened to enable efficient differentiation induction of desired nerve cells and the like. In case of mouse embryonic stem cells, for example, it is desirable that aggregates be formed preferably within 12 hours, more preferably within 6 hours. Meanwhile, in case of human embryonic stem cells, it is desirable that aggregates be formed preferably within 24 hours, more preferably within 12 hours. If this time is exceeded, homogenous aggregates of stem cells cannot be formed, which in turn can cause a remarkable reduction in differentiation efficiency in the subsequent step. This time to aggregate formation can be adjusted as appropriate by choosing a tool for cell aggregation, centrifugal conditions and the like by those skilled in the art.

Those skilled in the art are able to make a judgment concerning the "homogenous" formation of aggregates of stem cells and the formation of an epithelium-like structure in each cell type that forms aggregates, on the basis of the size of the aggregate masses and the number of cells therein, macroscopic morphology, microscopic morphology as analyzed by histological staining and uniformity thereof, the expression of differentiation and non-differentiation markers and uniformity thereof, the control of the expression of differentiation markers and synchronicity thereof, inter-aggregate reproducibility of differentiation efficiency, and the like.

Specifically, homogenous aggregates of stem cells can be formed by, for example, a method wherein embryonic stem cells are cultured for maintenance, followed by dispersion treatment, and suspended in an appropriate medium (for example, Glasgow MEM medium supplemented with 10% KSR, 0.1 mM non-essential amino acid solution, 2 mM glutamine, 1 mM pyruvic acid and 0.1 mM 2-mercaptoethanol; may contain appropriate amounts of factors described below, added as required, and the like), and the cells are suspended in 150 µL of the above-described medium at $3\times10^3$ cells per well using a non-cell-adhesive U-based 96-well culture plate to form aggregates rapidly.

(4) Step for Suspension-Culturing the Homogenous Aggregates of Stem Cells in a Serum-Free Medium This is a step wherein the homogenous aggregates of stem cells formed in (3) are suspension-cultured to induce the differentiation of stem cells.

"To suspension-culture the homogenous aggregates of stem cells" or "to culture the homogenous aggregates of stem cells as suspended aggregates (also referred to as aggregate masses)" refers to culturing the population of stem cells assembled to form homogenous aggregates, obtained in (3), in a culture medium under conditions that are non-adhesive to the cell culture vessel (herein, the above-described step (3) and step (4) are sometimes described as "the SFEBq method" together). When stem cells are suspension-cultured, the culture is preferably performed in the absence of feeder cells to facilitate the formation of suspended aggregates, and/or to achieve efficient induction of differentiation (for example, induction of differentiation into ectodermal cells such as nervous system cells).

A medium used in the suspension culture of the aggregates obtained in (3) above can be prepared with a medium for use for animal cell culture as a basal medium. Any basal medium available for culturing animal cells can be used; examples include, but are not limited to, BME medium, BGJb medium, CMRL 1066 medium, Glasgow MEM medium, Improved MEM Zinc Option medium, IMDM medium, Medium 199 medium, Eagle's MEM medium, αMEM medium, DMEM medium, Ham medium, RPMI 1640 medium, Fischer's medium, and a mixed medium thereof and the like. Unless otherwise specified, the medium used in the step described in (3) may be used as it is for the suspension culture.

When the above-mentioned aggregates are suspension-cultured, a serum-free medium is used as the medium. Here, a serum-free medium means a medium that does not contain unadjusted or unpurified serum; a medium containing a purified blood-derived component or animal tissue-derived component (for example, growth factor) is to be construed as a serum-free medium.

The serum-free medium used in the suspension culture can be, for example, one containing a serum substitute. The serum substitute can, for example, be one containing as appropriate an albumin (for example, lipid-rich albumin), transferrin, fatty acids, insulin, collagen precursor, trace elements, 2-mercaptoethanol or 3'-thiolglycerol, or their equivalents and the like. Such a serum substitute can be prepared by, for example, a method described in WO98/30679. To facilitate easier implementation of a method of the present invention, commercially available serum substitutes can be utilized. Examples of such commercially available serum substitutes include Knockout Serum Replacement (KSR), Chemically-defined Lipid Concentrated (produced by Gibco Company) and Glutamax (produced by Gibco Company).

In addition, the serum-free medium used in a method of the present invention can contain fatty acids or lipids, amino acids (for example, non-essential amino acids), vitamins, growth factors, cytokines, anti-oxidants, 2-mercaptoethanol, pyruvic acid, buffering agents, inorganic salts and the like. For example, 2-mercaptoethanol can be used without particular limitations, as far as it is used at a concentration suitable for embryonic stem cell culture, and it can be used at concentrations of, for example, about 0.05 to 1.0 mM, preferably about 0.1 to 0.5 mM, more preferably about 0.2 mM.

The serum-free medium used for the suspension culture is not particularly limited, as far as it is as described above. However, to avoid the painstakingness in preparing the serum-free medium, a serum-free medium (GMEM or dMEM, 0.1 mM 2-mercaptoethanol, 0.1 mM non-essential amino acids Mix, 1 mM sodium pyruvate) supplemented with an appropriate amount (e.g., 1-20%) of commercially available KSR can be used.

The culture vessel used for the suspension culture is not particularly limited, as far as it allows suspension culture of cells; examples include flasks, tissue culture flasks, dishes, Petri dishes, tissue culture dishes, multi-dishes, microplates, micro-well plates, multi-plates, multi-well plates, chamber slides, Petri dishes, tubes, trays, culturing bags, and roller bottles.

When aggregates are suspension-cultured, the culture vessel is preferably non-cell-adhesive. As the non-cell-adhesive culture vessel, a culture vessel whose surface has not been artificially treated for the purpose of increasing the adhesiveness to cells (e.g., coating treatment with an extracellular matrix and the like) can be used.

Other culturing conditions such as culturing temperature, $CO_2$ concentration and the like at the time of aggregate suspension culture can be set as appropriate. The culturing temperature is not particularly limited, and is, for example, about 30 to 40° C., preferably about 37° C. The $CO_2$ concentration is, for example, about 1 to 10%, preferably about 5%. The culturing time in this step is not particularly limited, and is normally 48 hours or more.

After the suspension culture, the aggregates may be kept as they are or dispersion-treated (for example, trypsin/EDTA treatment), and the cells may be further cultured under adhesive conditions (hereinafter, described as "adhesion culture" if required). If adhesion culture is performed, it is preferable that a cell-adhesive culture vessel, for example, a culture vessel coated with an extracellular matrix and the like (e.g., poly-D-lysine, laminin, fibronectin) be used. Culturing conditions such as culturing temperature and $CO_2$ concentration in the adhesion culture can easily be determined by those skilled in the art.

In the suspension culture and adhesion culture, a known differentiation inducer can be used in combination. For example, when nervous system cells are to be differentiation-induced from an embryonic stem cell, a known inducer of differentiation into nervous system cells can be used in combination. Examples of such differentiation inducers include NGF (Biochem. Biophys. Res. Commun., 199, 552(1994)), retinoic acid (Dev. Biol., 168, 342(1995); J. Neurosci., 16, 1056(1996)), BMP inhibitory factor [Nature, 376, 333-336(1995)], IGF (Genes & Development, 15, 3023-8(2003)), and the like.

According to the above-described suspension culture method and combination method of suspension culture and adhesion culture, differentiated cells such as ectodermal cells can be obtained from an embryonic stem cell by setting culture period and the like as appropriate. However, by further combining the methodologies described below as appropriate, nervous systems cells can be differentiation-induced more efficiently.

(5) Differentiation Induction of Nervous System Cells

In differentiation induction of forebrain nerve cells as nervous system cells, for example, more suitable methodologies of the present invention to be combined to perform suspension culture of the homogenous aggregates of stem cells obtained in (3) (hereinafter, sometimes described as "the aggregates of the present invention") are described in detail below. Hence, in the SFEBq method of the present invention, by combining the methodologies shown below, it is possible to obtain forebrain nerve cells selectively.

(5-1) Differentiation Induction of Forebrain Nerve Cells

Forebrain nerve cells can be differentiation-induced from a stem cell by the above-described suspension culture of the present invention, or, as required, by the above-described combination of suspension culture and adhesion culture. Preferably, from the viewpoint of improving/stabilizing etc., the differentiation efficiency for forebrain nerve cells and the like, the methodologies described below can be used in combination.

(5-1-1) Pattern Formation Factors

Suspension culture of aggregates of the present invention can be performed in the presence of a pattern formation factor. A pattern formation factor is a substance that acts on stem cells or progenitor cells to control the diverse destinations of differentiation; as such, pattern formation factors include secreted pattern formation factors. The secreted pattern formation factor is not particularly limited, as far as it is an active substance that activates or suppresses intracellular signals involved in differentiation control; examples include FGF, BMP, Wnt, Nodal, Notch, Shh and the like.

For differentiation induction into forebrain nerve cells with a secreted pattern formation factor, for example, the methodologies shown below are applicable.

(A) Inhibition of Nodal Signal and Inhibition of Wnt Signal

One methodology is suspension culture of the aggregates of the present invention in the presence of a Nodal signal inhibitor and/or a Wnt signal inhibitor. This methodology is useful in, for example, improving/stabilizing the efficiency of differentiation into forebrain nerve cells (particularly cerebral nerve cells). By using a Nodal signal inhibitor and a Wnt signal inhibitor in combination, a more remarkable effect is expectable.

The Nodal signal inhibitor is not particularly limited, as far as it is capable of suppressing the signal transduction mediated by Nodal. Nodal signal inhibitors include, for example, Lefty-A, Lefty-B, Lefty-1, Lefty-2, soluble Nodal receptors, Nodal antibodies, and Nodal receptor inhibitors; in particular, Lefty-A or Lefty-1 is preferable.

The concentration of the Nodal signal inhibitor used for suspension culture of the aggregates of the present invention can be a concentration that allows the differentiation of the aggregates of the present invention into nerves to be promoted, or that allows the above-described utility to be achieved. This concentration can be, for example, about 0.1 to 100 μg/ml, preferably about 0.5 to 50 μg/ml, more preferably about 1.0 to 10 μg/ml, most preferably about 5 μg/ml, for Lefty.

Although the Nodal signal inhibitor may be added to the medium already at the start of culturing the stem cell, it may also be added to the medium after several days of cultivation (for example, at a time within 10 days of cultivation). Preferably, Nodal signal inhibitor is added to the medium at a time within 5 days of cultivation.

The Wnt signal inhibitor is not particularly limited, as far as it is capable of suppressing the signal transduction mediated by Wnt. Wnt signal inhibitors include, for example, Dkk1, Cerberus protein, Wnt receptor inhibitors, soluble Wnt receptors, Wnt antibodies, casein kinase inhibitors, and dominant negative Wnt protein; in particular, Dkk1 or Cerberus protein is preferable.

The concentration of the Wnt signal inhibitor used for suspension culture of the aggregates of the present invention can be a concentration that allows the differentiation of the aggregates of the present invention into nerves to be promoted, or that allows the above-described utility to be achieved. This concentration can be, for example, about 0.05 to 20 μg/ml, preferably about 0.1 to 10 μg/ml, more preferably about 0.5 to 5.0 μg/ml, most preferably about 1 μg/ml, for Dkk1.

Although the Wnt signal inhibitor may be added to the medium already at the start of culturing the stem cell, it may also be added to the medium after several days of cultivation (for example, at a time within 10 days of cultivation). Preferably, the Wnt signal inhibitor is added to the medium at a time within 5 days of cultivation. Of course, suspension culture of the aggregates of the present invention can also be performed in the absence of a Nodal signal inhibitor and/or a Wnt signal inhibitor. It is also possible to switch these culturing conditions in the midst of suspension culture.

In another methodology, suspension culture of the aggregates of the present invention in a serum-free medium that substantially does not contain a Nodal signal promoter and/or a Wnt signal promoter, or in a serum-free medium wherein the Nodal signal promoter and/or the Wnt signal promoter has been substantially inactivated. This methodology is useful in, for example, promoting differentiation into forebrain nerve cells (particularly cerebral nerve cells).

A serum-free medium that substantially does not contain a Nodal signal promoter and/or a Wnt signal promoter refers to a serum-free medium that does not contain a Nodal signal promoter and/or a Wnt signal promoter at all, or a serum-free medium that contains a Nodal signal promoter and/or a Wnt signal promoter in an amount that does not adversely influence the formation of the aggregates of the present invention, and/or the cultivation (for example, cultivation for the purpose of differentiation induction) of the aggregates.

A serum-free medium that substantially does not contain a Nodal signal promoter and/or a Wnt signal promoter can be prepared by, for example, non-addition of a Nodal signal promoter and/or a Wnt signal promoter as a component of the medium, or a treatment to remove the Nodal signal promoter and/or the Wnt signal promoter from the medium containing the Nodal signal promoter and/or the Wnt signal promoter.

A serum-free medium wherein the Nodal signal promoter and/or the Wnt signal promoter has been substantially inactivated refers to a serum-free medium wherein by adding a Nodal signal inhibitor and/or a Wnt signal inhibitor to a serum-free medium containing a Nodal signal promoter and/or a Wnt signal promoter, the activity of the Nodal signal promoter and/or the Wnt signal promoter has been lost to an extent that does not adversely influence the formation of the aggregates of the present invention, and/or the cultivation of the aggregates.

The Nodal signal promoter is not particularly limited, as far as it is capable of enhancing the signal transduction mediated by Nodal. Nodal signal promoters include, for example, Nodal, proteins belonging to the TGFβ family (for example, activin), Smad protein, and active Nodal receptors.

The Wnt signal promoter is not particularly limited, as far as it is capable of enhancing the signal transduction mediated by Wnt. Wnt signal promoters include, for example, proteins belonging to the Wnt family (for example, Wnt1 to 16), GSK3 inhibitors, Wnt receptors, and the $Li^+$ ion.

(B) Inhibition of Notch Signal

One methodology is suspension culture of the aggregates of the present invention in the presence of a Notch signal inhibitor. This methodology is useful in, for example, improving/stabilizing the efficiency of differentiation into forebrain nerve cells (particularly cerebral nerve cells).

The Notch signal inhibitor is not particularly limited, as far as it is capable of suppressing the signal transduction mediated by Notch. Notch signal inhibitors include, for example, DAPT, DBZ, MDL28170 and the like; in particular, DAPT is preferable.

The concentration of the Notch signal inhibitor used for suspension culture of the aggregates of the present invention can be a concentration that allows the differentiation of the aggregates of the present invention into nerves to be promoted, or that allows the above-described utility to be achieved. This concentration can be, for example, about 0.1 to 1000 µM, preferably about 0.5 to 500 µM, more preferably about 1 to 100 µM, most preferably about 10 µM, for DAPT.

Although the Notch signal inhibitor may be added to the medium already at the start of culturing the stem cell, it may also be added to the medium after several days of cultivation (for example, at a time within 10 days of cultivation). Preferably, the Notch signal inhibitor is added to the medium at a time within 5 days of cultivation. Meanwhile, as stated below, it is also possible to selectively differentiation-induce particular layer-specific neurons by adding a Notch signal inhibitor to the medium at an optionally chosen time.

Still another methodology is suspension culture of the aggregates of the present invention in a serum-free medium that substantially does not contain a Notch signal promoter, or a serum-free medium wherein the Notch signal promoter has been substantially inactivated. This methodology is useful in, for example, promoting differentiation into forebrain nerve cells (particularly cerebral nerve cells).

A serum-free medium that substantially does not contain a Notch signal promoter refers to a serum-free medium that does not contain a Notch signal promoter at all, or a serum-free medium containing a Notch signal promoter in an amount that does not adversely influence the formation of the aggregates of the present invention, and/or the cultivation (for example, cultivation for the purpose of differentiation induction) of the aggregates. A serum-free medium that substantially does not contain a Notch signal promoter can be prepared by, for example, non-addition of a Notch signal promoter as a component of the medium, or a treatment to remove the Notch signal promoter from the medium containing the Notch signal promoter.

(C) Promotion or Inhibition of Fgf Signal

Still another methodology is suspension culture of the aggregates of the present invention in the presence of an Fgf signal promoter. This methodology is useful in, for example, promoting differentiation into ventral cerebral nerve cells or ventral cerebral cortical nerve cells, and in suppressing differentiation into dorsal cerebral nerve cells or dorsal cerebral cortical nerve cells. This methodology is also useful in promoting differentiation into rostral cerebral nerve cells or rostral cerebral cortical nerve cells, and in suppressing differentiation into caudal cerebral nerve cells and caudal cerebral cortical nerve cell.

The Fgf signal promoter is not particularly limited, as far as it is capable of enhancing the signal transduction mediated by Fgf. Preferable Fgf signal promoters include FGFs (e.g., Fgf 8, Fgf 2 and the like), Fgf agonists and Fgf receptor agonist peptides. The Fgf agonist is not particularly limited, as far as it is an Fgf agonist known per se. The Fgf receptor agonist peptide is not particularly limited, as far as it is an Fgf receptor agonist peptide known per se.

The concentration of the Fgf signal promoter used for suspension culture of the aggregates of the present invention can be a concentration that allows the above-described utility to be achieved. This concentration can be, for example, about 0.1 to 1000 ng/ml, preferably about 0.5 to 500 ng/nl, more preferably about 1 to 100 ng/ml, most preferably about 10 to 100 ng/ml, for Ffg8.

Although the Fgf signal inhibitor may be added to the medium already at the start of culturing the stem cell, it may also be added to the medium after 2 days of suspension culture, preferably after 4 days of suspension culture, and the like. Of course, suspension culture of embryonic stem cell can also be performed in the absence of an Fgf signal promoter. It is also possible to switch these culturing conditions in the midst of suspension culture.

Still another methodology is suspension culture of the aggregates of the present invention in the presence of an Fgf signal inhibitor. This methodology is useful in, for example, promoting differentiation into dorsal cerebral nerve cells or dorsal cerebral cortical nerve cells, and in suppressing differentiation into ventral cerebral nerve cells or ventral cerebral cortical nerve cells. This methodology is also useful in promoting differentiation into caudal cerebral nerve cells or caudal cerebral cortical nerve cells, and in suppressing differentiation into rostral cerebral nerve cells or rostral cerebral cortical nerve cells.

The Fgf signal inhibitor is not particularly limited, as far as it is capable of enhancing the signal transduction mediated by Fgf. Fgf signal inhibitors include, for example, antibodies against Fgf signal promoters, dominant negative mutants of Fgf signal promoters, soluble Fgf receptors, and Fgf receptor inhibitors; in particular, Fgf antibodies, Fgf dominant negative mutants, and Fgf receptor inhibitors are preferable.

The concentration of the Fgf signal inhibitor used for suspension culture can be a concentration that allows the above-described utility to be achieved. This concentration can be, for example, about 1 to 1000 ng/ml, preferably about 5 to 500 ng/ml, more preferably about 10 to 100 ng/ml, most preferably about 20 to 100 ng/ml, for a soluble Fgf receptor.

Although the Fgf signal inhibitor may be added to the medium already at the start of culturing the aggregates of the present invention, it may also be added to the medium after 2 days of suspension culture, preferably after 4 days of suspension culture, and the like. Of course, suspension culture of the aggregates of the present invention can also be performed in the absence of an Fgf signal inhibitor. It is also possible to switch these culturing conditions in the midst of suspension culture.

(D) Promotion of BMP Signal and Promotion of Wnt Signal

One methodology is suspension culture of the aggregates of the present invention in the presence of a BMP signal promoter or a Wnt signal promoter, or both. This methodology is useful in, for example, promoting differentiation into forebrain nerve cells (particularly cerebral nerve cells), preferably dorsal cerebral nerve cells or caudal cerebral nerve cells, more preferably hippocampal nerve cells. This methodology is also useful in suppressing differentiation into rostral cerebral nerve cells. This methodology does not always suppress differentiation into ventral cerebral nerve cells.

The BMP signal promoter is not particularly limited, as far as it is capable of enhancing the signal transduction mediated by BMP. BMP signal promoters include, for example, proteins belonging to the BMP family (for example, BMP2, BMP4, BMP7, GDF), BMP receptors, and Smad protein. BMP4 is preferable.

The concentration of the BMP signal promoter used for suspension culture can be a concentration that allows the above-described utility to be achieved. This concentration can be, for example, about 0.05 to 500 ng/ml, preferably about 0.1 to 100 ng/ml, more preferably about 0.1 to 5 ng/ml, most preferably about 0.2 to 2 ng/ml, for BMP4.

The BMP signal inhibitor may be added to the medium already at the start of culturing the aggregates of the present invention, it may also be added to the medium after 2 days of suspension culture, preferably after 4 days of suspension culture. Of course, suspension culture of the aggregates of the present invention can also be performed in the absence of a BMP signal promoter. It is also possible to switch these culturing conditions in the midst of suspension culture.

The Wnt signal promoter is not particularly limited, as far as it is capable of enhancing the signal transduction mediated by Wnt. Wnt signal promoters include, for example, proteins belonging to the Wnt family (for example, Wnt3a), GSK3 inhibitors, Wnt receptors, the $Li^+$ ion and the like; in particular, Wnt3a is preferable.

The concentration of the Wnt signal promoter used after suspension culture of the aggregates of the present invention is not limited, as far as it is a concentration that allows the above-described utility to be achieved; this concentration can be, for example, about 0.1 to 500 ng/ml, preferably about 1.0 to 100 ng/ml, more preferably about 5.0 to 50 ng/ml, most preferably about 50 ng/ml, for Wnt3a.

The Wnt signal promoter may be added to the medium already at the start of culturing the aggregates of the present invention, it may also be added to the medium several days just after the start of adhesion culture (for example, after 4 days following the start of suspension culture, or a time within 10 days of suspension culture). Preferably, the Wnt signal promoter is added to the medium at a time within 5 days of suspension culture.

(E) Promotion of Shh Signal

Still another methodology is suspension culture of the aggregates of the present invention in the presence of an Shh signal promoter. This methodology is useful in promoting differentiation into cerebral nerve cells, preferably into cerebral basal nuclear nerve cells, and is also useful in promoting differentiation into cerebral basal nuclear ventral nerve cells, and also useful in promoting differentiation into cerebral basal nuclear dorsal nerve cells.

As described in detail below, by changing the concentration of the Shh signal promoter added to the medium, stem cells can be selectively differentiation-induced into dorsal and ventral cerebral basal nuclear nerve cells, respectively.

The Shh signal promoter is not particularly limited, as far as it is capable of enhancing the signal transduction mediated by Shh. Shh signal promoters include, for example, proteins belonging to the Hedgehog family (for example, Shh), Shh receptors and Shh receptor agonists; in particular, Shh is preferable.

The concentration of the Shh signal promoter used for suspension culture can be a concentration that allows the above-described utility to be achieved. This concentration can be, for example, about 1.0 to 1000 nM, preferably about 1.0 to 500 nM, more preferably about 2 to 500 nM, most preferably about 3 to 300 nM, for Shh.

Here, when differentiation induction into cerebral basal nuclear dorsal nerve cells is performed in cultivation by the SFEBq method, it is desirable that the cells be cultured at an Shh signal promoter concentration of, for example, about 0.5 to 20 nM, preferably about 2 to 10 nM. Meanwhile, when differentiation induction into cerebral basal nuclear ventral nerve cells is performed by applying the SFEBq method, it is desirable that the cells be cultured at an Shh signal promoter concentration of, for example, about 10 to 300 nM, preferably about 20 to 100 nM.

Although the Shh signal promoter may be added to the medium already at the start of culturing the embryonic stem cell, it can also be added to the medium, for example, after 2 days of suspension culture, preferably after 4 days of suspension culture. Of course, suspension culture of embryonic stem cells can also be performed in the absence of an Shh signal promoter. It is also possible to switch these culturing conditions in the midst of suspension culture.

Still another methodology is suspension culture of embryonic stem cells in the presence of an Shh signal inhibitor. Expected by the addition of the Shh signal promoter are promotion of the differentiation of embryonic stem cells into ventral forebrain nerve cells, suppression of the differentiation of embryonic stem cells into dorsal forebrain nerve cells, and the like. Therefore, using an Shh signal inhibitor is expected to have effects such as suppression of the differentiation of ventral forebrain nerve cells and promotion of the differentiation of dorsal forebrain nerve cells.

The Shh signal inhibitor is not particularly limited, as far as it is capable of enhancing the signal transduction mediated by Shh. Shh signal inhibitors include, for example, antibodies against Shh signal promoters, dominant negative mutants of Shh signal promoters, soluble Shh receptors, and Shh receptor antagonists; in particular, Shh antibodies and Shh dominant negative mutants are preferable.

Of course, suspension culture of embryonic stem cells can also be performed in the absence of an Shh signal inhibitor. It is also possible to switch these culturing conditions in the midst of suspension culture.

(5-1-2) Adhesion Culture

Another methodology is performing adhesion culture after the SFEBq method. The aggregate masses as they are, or after being subjected to a dispersion treatment (for example, trypsin/EDTA treatment), cells can be subjected to adhesion culture. In the adhesion culture, it is preferable to use a cell-adhesive culture vessel, for example, one coated with an extracellular matrix or the like (for example, poly-D-lysine, laminin, fibronectin). Adhesion culture can be performed for, for example, 1 day or more, preferably 1 to 14 days, more preferably 2 to 5 days.

The homogenous aggregates of stem cells obtained by the SFEBq method of the present invention enable good differentiation induction, as with suspension culture, even on the above-described coated culture vessel.

(5-1-3) Summary

The various methodologies described above can be combined as appropriate to efficiently obtain forebrain nerve cells, or particular forebrain nerve cells (for example, cerebral nerve cells, ventral cerebral nerve cells, dorsal cerebral nerve cells, rostral cerebral nerve cells, caudal cerebral nerve cells, cerebral basal nuclear dorsal nerve cells, cerebral basal nuclear ventral nerve cells and the like).

By combining methodologies having the same effect, better effects are expectable.

(6) Selective Induction of Differentiation into Cerebral Cortical Layer-Specific Neurons As stated above, cerebral cortical nerve cells can be differentiation-induced from a stem cell by the above-described suspension culture of the aggregates of the present invention (SFEBq method), but from the viewpoint of selectively inducing differentiation into cerebral cortical layer-specific neurons, it is preferable that the methodologies described below be used in combination. Here, "cerebral cortex" is a layer of grey matter of nerve cells spreading over the surface of the cerebellum, the nerve cells being orderly arranged in a regular 6-layer structure. As mentioned herein, "cerebral cortical layer-specific neurons" refer to specific cerebral cortical nerve cells that constitute each of the six layers.

(6-1) Temporal Control of Suspension Culture

One methodology is a method wherein suspension culture of the aggregates of the present invention is performed for 60 hours to 350 hours. According to this methodology, for example, via common nerve differentiation, stem cells can be differentiated into cells specific for the layers of cerebral cortex.

Hence, according to the SFEBq method of the present invention, after differentiation induction to cerebral progenitor cells, and within the above-described time zone, the individual layer-specific neurons are induced in the same order as the order of development of cerebral cortical layer-specific neurons in the developmental process (see Shen et al, Nature Neurosci., 9, 743-751(2006)).

Specifically, first, cerebrum 1st layer-specific Reelin-positive cells (Cajal-Retzius cells) are induced, and then 6th layer-specific Tbr1-positive cells are induced. Furthermore, 5th layer-specific Crip2-positive cells are induced, and then 2nd-3rd layer-specific Brn2-positive cells are induced.

(6-2) Control with Notch Signal

Another methodology is selectively inducing differentiation into particular layer-specific neurons by adding a Notch signal inhibitor to the medium at an optionally chosen time in the SFEBq method of the present invention. According to this methodology, stem cells can be differentiated into cells specific for the layers of cerebral cortex.

The choice of Notch signal inhibitor and the concentration in the suspension culture are as described in the foregoing (B) in (5-1-1).

By adding a Notch signal inhibitor to the medium at an appropriate time, cerebral cortical layer-specific neurons can be differentiation-induced. For example, when the SFEBq method was applied to mouse ES cells, cells undergoing a DAPT treatment after being cultured for 9 days (about 216 hours) are induced to differentiate into 1st cerebral layer-specific Reelin-positive cells (Cajal-Retzius cells). Meanwhile, cells undergoing a DAPT treatment after being cultured for 12 days (about 288 hours) are induced to differentiate into 5th layer-specific Crip2-positive cells.

(7) Selective Induction of Differentiation into Hypothalamic Neurons

The present invention also provides a method of inducing the differentiation of progenitor cells of the diencephalon, particularly of hypothalamic neurons, or hypothalamic neurons further differentiated and matured therefrom, from a stem cell. In this case, it is desirable that the serum-free medium applied to the above-described SFEBq method substantially does not contain growth factors such as Nodal signal promoters, Wnt signal promoters, FGF signal promoters, BMP signal promoters, and retinoic acid, and insulins. With the provision that these growth factors and the insulins are substantially not contained, a medium used to culture an optionally chosen animal cell can be prepared as a basal medium.

The serum-free medium used for suspension culture preferably contains selenitic acid or a salt thereof for promoting the selective differentiation into hypothalamic neuron progenitor cells. The salt of selenitic acid is preferably sodium selenite. The concentration of selenitic acid or a salt thereof is normally about 1 to 100 µg/ml, preferably about 10 to 50 µg/ml.

Although the selenitic acid or a salt thereof may be added to the medium already at the start of culturing the pluripotent stem cell, it can be added to the medium, for example, after 2 days following the start of suspension culture.

The serum-free medium used for suspension culture may contain an Shh signal promoter for promoting the selective differentiation into hypothalamic neuron progenitor cells. The Shh signal promoter is not particularly limited, as far as it is capable of enhancing the signal transduction mediated by Shh. Shh signal promoters include, for example, proteins belonging to the Hedgehog family (for example, Shh, Shh-N), Shh receptors, Shh receptor agonists (e.g., Purmorphamine (2-(1-Naphthoxy)-6-(4-morpholinoanilino)-9-cyclohexylpurine)); in particular, Shh, Shh-N, and Purmorphamine are preferable.

The concentration of the Shh signal promoter used for suspension culture can be a concentration that allows selective differentiation into hypothalamic neuron progenitor cells to be achieved. This concentration, for example, can be about 0.5 to 500 nM, preferably about 3 to 300 nM, for Shh-N, and about 0.02 to 20 nM, preferably about 0.1 to 5 nM, for Purmorphamine.

Although the Shh signal promoter may be added to the medium already at the start of culturing the pluripotent stem cell, it can be added to the medium for example, after 2 days following the start of suspension culture, preferably after 4 days following the start of suspension culture.

The medium used for suspension culture (herein referred to as "differentiation medium") is a serum-free medium that substantially does not contain growth factors such as Nodal signal promoters, Wnt signal promoters, FGF signal promoters, BMP signal promoters and retinoic acid, and insulin.

The "serum-free medium that substantially does not contain growth factors and insulin" refers to a serum-free medium that does not at all contain growth factor and insulin, or a serum-free medium that contains growth factor and/or insulin in an amount that does not adversely influence the selective differentiation of hypothalamic neuron into progenitor cells. Such a serum-free medium can be prepared by, for example, non-addition of growth factors and insulins as medium components, or by a treatment to remove factors from the medium containing the factors which are Nodal signal promoters, Wnt signal promoters, FGF signal promoters, BMP signal promoters, retinoic acid and insulins.

Alternatively, the serum-free medium that substantially does not contain a growth factor and insulin can be a serum-free medium wherein the growth factor and insulin have been substantially inactivated; this medium refers to a serum-free medium wherein by adding a growth factor signal inhibitor and/or an insulin signal inhibitor to a serum-free medium containing growth factor and insulin, the activities of the growth factor and insulin have been lost to an extent that does not adversely influence the selective differentiation of hypothalamic neuron progenitor cells.

Referring to "a medium that substantially does not contain a growth factor" as mentioned herein, "a growth factor" means an optionally chosen factor that is generally added as a serum substitute in cell culture using a serum-free medium, and that has the action of inhibiting/suppressing the selective differentiation of hypothalamic neuron progenitor cells from an ES cell. Specifically, as the "growth factors", Nodal signal promoters, Wnt signal promoters, FGF signal promoters, BMP signal promoters, retinoic acid and the like can be mentioned. "A medium that substantially does not contain a growth factor" is preferably a medium that substantially does not contain at least one growth factor selected from the group consisting of Nodal signal promoters, Wnt signal promoters, FGF signal promoters, BMP signal promoters and retinoic acid, most preferably a medium that substantially does not contain any of these factors. Lipid-rich albumin is also included in "growth factor", the medium used in the present invention is preferably a medium that does not contain lipid-rich albumin.

Nodal signal promoters include, for example, Nodal, proteins belonging to the TGFβ family (for example, activin), Smad proteins, and active Nodal receptors. Preferably, the Nodal signal promoter whose entry in the serum-free medium is unwanted is Nodal.

Wnt signal promoters include, for example, proteins belonging to the Wnt family (for example, Wnt 1 to 16), GSK3 inhibitors, Wnt receptors, and the Li$^+$ ion. Preferably, the Wnt signal promoter whose entry in the serum-free medium is unwanted is Wnt3a.

FGF signal promoters include, for example, proteins belonging to the FGF family (for example, FGF1 to 23). Preferably, the FGF signal promoter whose entry in the serum-free medium is unwanted is FGF8b.

BMP signal promoters include, for example, proteins belonging to the BMP family (for example, BMP2, BMP4, BMP7, GDF), BMP receptors, and Smad protein. Preferably, the BMP signal promoter whose entry in the serum-free medium is unwanted is BMP7.

As used herein, the "insulin" means a compound that promotes insulin signals. An insulin signal promoter is not particularly limited, as far as it acts to promote the transduction of signals of insulin, and the promoter may act on any stage of the insulin signal transduction pathway (factors that act on the upstream or downstream of insulin, insulin agonists, similar substances and the like).

Insulin includes insulin and substances similar to insulin (analogues). A substance similar to insulin refers to an optionally chosen substance having an insulin-like action (herein, refers to an action to inhibit/suppress the selective differentiation of diencephalon, particularly the hypothalamus, specifically rostral hypothalamic nerve cells (neurons), or progenitor cells thereof, from a pluripotent stem cell); examples include IGF-I and the like.

For the treatment to remove growth factors and insulins from the medium containing the growth factors and insulins to obtain the above-described serum-free medium, for example, antibodies against the above-described growth factors (for example, Nodal signal promoters, Wnt signal promoters, FGF signal promoters, BMP signal promoters, retinoic acid, lipid-rich albumin and the like) and insulins can be used. Deactivation of growth factors and insulins can be performed by the addition of growth factor signal inhibitor and insulin signal inhibitor. These inhibitors can be optionally chosen substances that inhibit the upstream or downstream of the signal transduction pathway by growth factor or insulin; examples include antibodies against growth factors/insulin, soluble receptors of growth factors/insulin, antibodies against growth factors/insulin receptors, growth factor/insulin antagonists and the like. These substances are added to the medium in amounts suitable for obtaining the desired effect (selective differentiation into hypothalamic neuron progenitor cells).

The Nodal signal inhibitor is not particularly limited, as far as it is capable of suppressing the signal transduction mediated by Nodal. Nodal signal inhibitors include, for example, SB431542 (Sigma), Lefty-A, Lefty-B, Lefty-1, Lefty-2, soluble Nodal receptors, Nodal antibodies, and Nodal receptor inhibitors; in particular, SB431542 (4-(5-benzo[1,3] dioxol-5-yl-4-pyridin-2-yl-1H-imidazol-2-yl)-benzamide) is preferable.

The Wnt signal inhibitor is not particularly limited, as far as it is capable of suppressing the signal transduction mediated by Wnt. Wnt signal inhibitors include, for example, Dkk1, Cerberus protein, Wnt receptor inhibitors, soluble Wnt receptors, Wnt antibodies, casein kinase inhibitors, and dominant negative Wnt protein; in particular, Dkk1 is preferable.

The FGF signal inhibitor is not particularly limited, as far as it is capable of suppressing the signal transduction mediated by FGF. FGF signal inhibitors include, for example, anti-FGF antibodies, soluble FGF receptors, and FGF receptor inhibitors (for example, Su5402).

The BMP signal inhibitor is not particularly limited, as far as it is capable of suppressing the signal transduction mediated by BMP. BMP signal inhibitors include, for example, BMPRFc (R&D), anti-BMP antibodies, soluble BMP receptors, and BMP receptor inhibitors; in particular, BMPRFc is preferable.

The retinoic acid (RA) inhibitor is not particularly limited, as far as it is capable of suppressing the signal transduction mediated by RA. RA inhibitors include, for example, anti-RA antibodies, soluble RA receptors, and RA receptor inhibitors.

The concentration of each of the above-described signal inhibitors used for suspension culture can be a concentration that allows selective differentiation into hypothalamic neuron progenitor cells to be achieved. For example, for SB431542, the concentration is about 0.1 to 100 nM, preferably about 5 to 30 nM. For Dkk1, the concentration is about 10 to 1000 ng/ml, preferably about 100 to 1000 ng/ml. For BMPRFc, the concentration is about 0.1 to 10 µg/ml, preferably about 0.5 to 3 µg/ml.

Although each of the signal inhibitors described above is most preferably added to the medium already at the start of culturing the pluripotent stem cell, addition to the medium after several days of cultivation is sometimes possible.

The intracellular signal transduction of insulin is involved by roughly two pathways (MAPK pathway and PI3K-Akt pathway); insulin signal inhibitors that can be used in the suspension culture of the present invention include inhibitors of PI3K, which is a downstream factor in the insulin signal transduction pathway, and inhibitors of Akt, which is a further downstream factor (the MAPK inhibitor PD98059 did not antagonize the inhibitory action of insulin on differentiation into hypothalamic neuron progenitor cells (Example 15)). PI3K inhibitors that can be used in the present invention include LY294002 (2-(4-morpholinyl)-8-phenyl-1(4H)-benzopyran-4-one hydrochloride) (Cayman Chemical), Wortmannin (FERMENTEK) and the like; LY294002 is preferable. Akt inhibitors that can be used in the present invention include Akt inhibitors I to X (Calbiochem) and the like; Akt inhibitor VIII (1,3-Dihydro-1-(1-((4-(6-phenyl-1H-imidazo[4,5-g] quinoxalin-7-yl)phenyl)methyl)-4-piperidinyl)-2H-benzimidazol-2-one) is preferable.

As far as insulin signals are inhibited, and the selective differentiation of hypothalamic neuron progenitor cells is achieved, in the suspension culture, an inhibitor selected from among the above-described PI3K inhibitors or Akt inhibitors may be used alone, or a PI3K inhibitor and an Akt inhibitor may be used in combination. Two kinds or more can be selected from among the respective inhibitors and used in combination.

The concentration of the PI3K inhibitor/Akt inhibitor used in the suspension culture can be a concentration that allows the selective differentiation into hypothalamic neuron progenitor cells to be achieved. For example, for LY294002, the concentration is about 0.5 to 30 µM, preferably about 2 to 10 µM. For Akt inhibitor VIII, the concentration is about 0.1 to 10 µM, preferably about 0.5 to 5 µM.

Although the PI3K inhibitor/Akt inhibitor is added to the medium most preferably already at the start of culturing the pluripotent stem cell, the inhibitor must be added to the differentiation medium at a time at least until day 6 of cultivation (preferably at least until day 2 of cultivation) for the differentiation of rodent (for example, mouse) pluripotent cells, and at a time at least until day 24 of cultivation (preferably added at least until day 9 of cultivation) for the differentiation of primate (for example, human) pluripotent cells.

The differentiation medium used in a preferred embodiment of the present invention is a chemically defined medium that contains neither the above-described growth factors nor insulin (growth factor-free CDM; referred to as gfCDM) (see Example 13 below). This gfCDM medium is a modification of a previously reported CDM medium (Mol. Cell. Biol. 15:141-151(1995)).

To suppress the action of endogenous growth factors/insulin, a growth factor inhibitor/insulin inhibitor may be further added to the gfCDM medium or another medium.

The differentiation medium used in another preferred embodiment of the present invention is a serum-free medium that contains at least one inhibitor selected from the group consisting of PI3K inhibitors and Akt inhibitors and insulins, and that substantially does not contain the above-described growth factors other than insulin (Nodal signal promoters, Wnt signal promoters, FGF signal promoters, BMP signal promoters, retinoic acid and the like). For example, as shown in Example 19 below, when suspension culture is performed using an insulin-free medium in differentiation induction of primate pluripotent stem cells, there are some cases in which the cells die and are unlikely to proliferate. To avoid this cell death, it is preferable that insulin be added to accentuate cell proliferation, and an insulin signal inhibitor that antagonizes the differentiation induction inhibitory effect of insulin (e.g., PI3K inhibitor/Akt inhibitor) be added at the same time. In this case, the concentration of the insulin contained in the differentiation medium is a concentration that allows the proliferation of pluripotent stem cells to be promoted. For example, the concentration is normally about 0.02 to 40 µg/ml, preferably about 0.1 to 10 µg/ml, for insulin. The ranges of concentrations of the PI3K inhibitor and the Akt inhibitor are as described above.

To suppress cell death during dispersion suspension culture, it is preferable that in addition to the addition of insulin, a ROCK inhibitor (Y-27632 ((+)-(R)-trans-4-(1-aminoethyl)-N-(4-pyridyl)cyclohexanecarboxamide dihydrochloride); Watanabe et al., Nature Biotechnology 2007) be added from the start of cultivation. The concentration of the ROCK inhibitor used for suspension culture is a concentration that allows cell death during dispersion suspension culture to be suppressed. For example, for Y-27632, this concentration is normally about 0.1 to 200 µM, preferably about 2 to 50 µM.

In a method of the present invention, depending on the presence or absence of an Shh signal promoter in the medium used for suspension culture, the differentiation potential of hypothalamic neuron progenitor cells that can be obtained differs.

When suspension culture of pluripotent stem cells is performed in a medium containing an Shh signal promoter, ventral hypothalamic neuron progenitor cells having the potential for differentiating into medial ventral nuclear neurons, type A12 dopamine neurons, arcuate nuclear neurons or orexin-positive neurons are selectively induced. Preferable Shh signal promoters are Shh, Shh-N, and Purmorphamine.

The concentration of the Shh signal promoter used for suspension culture can be a concentration that allows selective differentiation into ventral hypothalamic neuron progenitor cells to be achieved. This concentration can be, for example, about 1 to 1000 nM, preferably about 10 to 100 nM, for Shh-N, and about 0.05 to 50 nM, preferably about 0.1 to 10 nM, for Purmorphamine.

Although the Shh signal promoter may be added to the medium already at the start of culturing the pluripotent stem cell, it can be added to the medium, for example, after 2 days following the start of suspension culture, preferably after 4 days following the start of suspension culture. As required, the presence or absence of an Shh signal promoter may be switched in the midst of suspension culture.

Meanwhile, when suspension culture of pluripotent stem cells is performed in a medium that substantially does not contain an Shh signal promoter, dorsal hypothalamic neuron progenitor cells having the potential for differentiating into vasopressin-producing endocrine cells are selectively induced.

The suspension culture in a medium that substantially does not contain an Shh signal promoter may be performed in the presence of an Shh signal inhibitor. The use of an Shh signal inhibitor is expected to be effective in suppressing the differentiation of ventral hypothalamic neurons, promoting the differentiation of dorsal hypothalamic neurons, and the like.

The Shh signal inhibitor is not particularly limited, as far as it is capable of enhancing the signal transduction mediated by Shh. Shh signal inhibitors include, for example, antibodies against Shh signal promoters, dominant negative mutants of Shh signal promoters, soluble Shh receptors, and Shh receptor antagonists. Shh signal inhibitors include, for example, Cyclopamine (11-Deoxojervine) and the like. As required, the presence or absence of an Shh signal inhibitor may be switched in the midst of suspension culture.

The culture vessel used for the suspension culture of pluripotent stem cells is not particularly limited, as far as it allows suspension culture of cells; examples include flasks, tissue culture flasks, dishes, Petri dishes, tissue culture dishes, multi-dishes, microplates, micro-well plates, multiplates, multi-well plates, chamber slides, Petri dishes, tubes, trays, culturing bags, and roller bottles.

When pluripotent stem cells are suspension-cultured, the culture vessel is preferably non-cell-adhesive. As the non-cell-adhesive vessel, a culture vessel whose surface has not been artificially treated for the purpose of increasing the adhesiveness to cells (for example, coating treatment with an extracellular matrix and the like) can be used.

The concentration of pluripotent stem cells at the start of cultivation can be set as appropriate to allow suspended aggregates of pluripotent stem cells to be formed more efficiently. The concentration of pluripotent stem cells at the start of cultivation is not particularly limited, as far as it is a concentration that allows suspended aggregates of pluripotent stem cells to be formed, and the concentration can be, for example, about $1\times10^4$ to about $5\times10^5$ cells/ml, preferably about $3\times10^4$ to about $1\times10^5$ cells/ml.

Other culturing conditions such as culturing temperature and $CO_2$ concentration in the suspension culture of pluripotent stem cells can be set as appropriate. The culturing temperature is not particularly limited, and is, for example, about 30 to 40° C., preferably about 37° C. The $CO_2$ concentration is, for example, about 1 to 10%, preferably about 5%.

Specifically, as a method of suspension culture of pluripotent stem cells, for example, a method can be mentioned wherein pluripotent stem cells are cultured for maintenance, then dispersion-treated, suspended in an appropriate medium, seeded to a non-cell-adhesive culture vessel at a cell density of $1\times10^4$ to $5\times10^6$ cells/ml, and cultured, for example, in a $CO_2$ incubator aerated with 5% carbon dioxide at 37° C. for at least 5 days (preferably 7 days or more).

For example, suspension culture of pluripotent stem cells is performed by suspending the cells in 150 µl of a differentiation medium to obtain a cell density of about 2500 to about 5000 cells (for example, about 3000 cells) per well on a non-adhesive 96-well culture plate.

By isolating from the culture obtained by suspension culture, hypothalamic neuron progenitor cells can be obtained. "A culture" refers to a resulting product obtained by culturing cells, and include cells, medium, and, in some cases, cell-secreted components and the like. "Isolation" means removing components other than the desired cells (cells, proteins, medium and the like).

After suspension culture, the aggregate masses containing hypothalamic neuron progenitor cells can be kept as they are, or subjected to a dispersion treatment (for example, trypsin/EDTA treatment), and then the cells can be further cultured under adhesive conditions (hereinafter, abbreviated as "adhesion culture" as required). In the adhesion culture, it is preferable to use a cell-adhesive culture vessel, for example, one coated with an extracellular matrix or the like (for example, poly-D-lysine, laminin, fibronectin). Culturing conditions such as culturing temperature and $CO_2$ concentration in the adhesion culture can easily be determined by those skilled in the art.

The medium used in the adhesion culture may contain any other substances, as far as it allows hypothalamic neuron progenitor cells to be differentiated into intended cells. This medium may contain "growth factors" or "insulin" and the like that are not used in the suspension culture as required, and can also contain a serum substitute, as well as fatty acids or lipids, amino acids (for example, non-essential amino acids), vitamins, growth factors, cytokines, antioxidants, 2-mercaptoethanol, pyruvic acid, buffering agents, inorganic salts and the like. The serum substitute can be, for example, one containing as appropriate albumin (for example, lipid-rich albumin), transferrin, fatty acids, insulin, collagen precursor, trace elements, 2-mercaptoethanol or 3'-thiolglycerol, or equivalents thereof and the like; examples of commercially available serum substitutes include knockout Serum Replacement (KSR), Chemically-defined Lipid concentrated (produced by Gibco Company) and Glutamax (produced by Gibco Company).

The medium used in the adhesion culture can further contain various additives (N2 additives, B27 additives and the like) as required.

In the adhesion culture, a known differentiation inducer can be used. Differentiation inducers that can be used to induce the differentiation of particular hypothalamic neurons (dorsal hypothalamic neurons, ventral hypothalamic neurons and the like) from a hypothalamic neuron progenitor cell include ciliary neurotrophic factor (CNTF), brain-derived neurotrophic factor (BDNF) and the like. A differentiation inducer can be chosen as appropriate depending on the desired kind of mature cells. An addition concentration can also be set as appropriate according to the substance used, the desired kind of cells and the like. For example, when dorsal hypothalamic neurons or ventral hypothalamic neurons are to be induced using CNTF, the appropriate concentration is normally 1 to 200 ng/ml, preferably 2 to 50 ng/ml. When ventral hypothalamic neurons (medial ventral nuclear neurons, type A12 dopamine neurons, arcuate nuclear neurons, orexin-positive neurons and the like) are to be induced using BDNF, the appropriate concentration is normally 1 to 1000 ng/ml, preferably 10 to 200 ng/ml.

The differentiation inducer may be added to the medium already at the start of adhesion culture, and it may also be added to the medium several days after the start of adhesion culture.

According to the above-described suspension culture method and the combination method of suspension culture and adhesion culture, by setting duration of culturing and the like as appropriate, hypothalamic neuron progenitor cells can be obtained from a pluripotent stem cell, and hypothalamic neurons further differentiated and matured therefrom can also be obtained.

For the cells obtained by the above-described suspension culture method or the combination method of suspension culture and adhesion culture, the type of cells into which they have differentiated can be determined with the presence or absence of the expression of a marker gene, or, in case of nerve endocrine cells, the release of a secreted protein (hormone) to the medium or the accumulation of a progenitor protein thereof in the cells, or the like as an index, or by combining these indexes as required. The cells obtained can also be identified by observing the morphology of the cells. Furthermore, it is also possible to isolate desired particular cells on the basis of these marker expression patterns and cell morphology.

Examples of such marker genes that can be utilized include, but are not limited to, publicly known markers such as N-cadherin (nerve cells), Rx (hypothalamic and retinal progenitor cells), nestin (expressed in hypothalamic neuron progenitor cells, but not expressed in retinal progenitor cells), Sox1 (expressed in hypothalamic nerve epithelium, but not expressed in the retina), BF1 (endbrain progenitor cell), Nkx2.1 (ventral), PAX6 (dorsal), Foxb1 (mamillary body neuron in the caudal hypothalamus), SF1 (VMH progenitor cells after mitosis), Otp (dorsal hypothalamus), GluT2, TH, AgRP, NPY, Orexin, Otx2 (fore-midbrain marker), Six3 (rostral forebrain), Vax1, Irx3 (caudal diencephalon and brain tissue more caudal therefrom), En2 (typically midbrain) and Hoxb9 (caudal CNS). The identity of the cells obtained can be determined by combining as appropriate the presence or absence of the expression of these marker genes.

The expression of a marker gene is analyzed by, for example, performing quantitative PCR using the 7500 Fast Real-Time PCR System (Applied Biosystems) in accordance with the manufacturer's instructions, and normalizing the obtained data by the expression of GAPDH. The method of quantitative PCR is obvious to those skilled in the art. Alternatively, cells may be manipulated to allow the desired marker gene to be expressed as a fusion protein of a marker gene product and GFP or the like (knocking-in). It is also possible to detect the expression of the protein using an antibody specific for a marker gene product.

The hormones secreted by the hypothalamus include CRH (adrenocorticotropic hormone releasing hormone), GHRH (growth hormone releasing hormone), GIH (growth hormone inhibitory hormone), GnRH (gonadotropic hormone releasing hormone), PRF (prolactin releasing factor), PIF (prolactin inhibitory factor), TRH (thyroid stimulating hormone releasing hormone), SS (somatostatin), vasopressin (ADH: antidiuretic hormone), oxytocin and the like. With the production/secretion of these hormones as an index, the properties of the cells obtained by a method of the present invention are confirmed.

For example, an arginine-vasopressin (AVP)-producing neuron morphologically has a large, round or oval cell body (20-30 µm in longitudinal direction) with a long axon and a few dendrites. This neuron accumulates Neurophysin II (NP II) in the cells thereof, and releases AVP upon in the medium upon stimulation with a high level of potassium.

Detection of these proteins can be performed by immunostaining or radioimmunoassay. For other hormone-producing neurons, the same assay is possible using antibodies specific for the hormone produced and the like, and the like. These methods are obvious to those skilled in the art.

(8) Cell Cultures and Use as Pharmaceuticals

The present invention also provides a cell culture obtained by a method of the present invention. The cell culture of the present invention can be, for example, suspended aggregates of stem cells, cells prepared by dispersion-treating the suspended aggregates, cells obtained by culturing the dispersion-treated cells and the like. The present invention also provides homogenous cells isolated and purified from a cell culture to an extent that allows the cells to be administered to a test subject, for example, forebrain nerve cells such as cerebral nerve cells and hypothalamic neurons.

Cells obtained by a method of the present invention can be used as therapeutic drugs for diseases based on disorders of nervous system cells, for example, forebrain nerve cell and sensory cells, or can be used to supplement the cells in cell injuries due to other causes and for other purposes. Examples of diseases based on disorders of nervous system cells include Parkinson's disease, spinocerebellar degeneration, Huntington chorea, Alzheimer's disease, ischemic cerebral diseases (for example, cerebral stroke), epilepsy, brain traumas, spinal injuries, motor nerve diseases, neurodegenerative diseases, pigmentary degeneration of the retina, age-related macular degeneration, cochlear hearing loss, multiple sclerosis, amyotrophic lateral sclerosis, diseases caused by neurotoxic disorders, and the like. Specifically, diseases based on disorders of forebrain nerve cells, particularly of endbrain nerve cells, include, for example, Huntington chorea, Alzheimer's disease, ischemic cerebral diseases (for example, cerebral stroke), and brain traumas.

The diencephalon is the generic name for the thalamus and the hypothalamus. The hypothalamus is the center of the autonomic nerves, secreting hormones to regulate the functions of the pituitary gland, and mediating the regulation of body temperature, eating, drinking, the circulatory system and the like. Therefore, cells obtained by a method of the present invention can be used as a therapeutic drug for a disease resulting from cell injuries (cell damage, dysfunction and the like) in the diencephalon, particularly in the hypothalamus, and can also be used to supply lost cells after neurosurgery (for example, after brain tumor extirpation).

Diseases that can be treated/mitigated by transplanting cells obtained by a method of the present invention include endocrine abnormalities (for example, central diabetes insipidus, Fröhlich syndrome, hypothalamic hypopituitarism, hypothalamic syndrome), eating disorders (apastia/bulimia), sleep disorders, diurnal rhythm disorders and the like.

When cells, for example, nervous system cells, obtained by a method of the present invention are used as a therapeutic drug for a disease based on a disorder of the cells, it is preferable that the cells be transplanted to the subject after increasing the purity of the cells.

Any method of increasing cell purity can be used, as far as it is a method of cell separation and purification in public knowledge; such methods include, for example, a method using a flow cytometer (see, for example, Antibodies—A Laboratory Manual, Cold Spring Harbor Laboratory (1988), Monoclonal Antibodies: principles and practice, Third Edition, Acad. Press (1993), Int. Immunol., 10, 275 (1998)), the panning method (see, for example, Monoclonal Antibodies: principles and practice, Third Edition, Acad. Press (1993), Antibody Engineering, A Practical Approach, IRL Press at Oxford University Press (1996), J. Immunol., 141, 2797 (1988)), and cell fractionation based on differences of sucrose density (see, for example, Soshiki Baiyou no Gijyutsu (3rd edition)).

The method of the present invention for increasing cell purity comprises a step for culturing cells, for example, nervous system cells, obtained by inducing the differentiation of the above-described stem cells, in a medium containing an anticancer agent. Thereby, undifferentiated cells can be removed, making it possible to obtain differentiated cells of higher purity, which are more suitable for pharmaceutical use. Hence, by a treatment with an anticancer agent, cells other than desired differentiated cells, for example, undifferentiated cells, can be removed.

Here, the anticancer agent is exemplified by mitomycin C, 5-fluorouracil, Adriamycin, Ara-C, methotrexate and the like. These anticancer agents are preferably used at concentrations that are more cytotoxic to undifferentiated cells than to differentiation-induced cells. Specifically, cultivation with these anticancer agents may be performed in accordance with the above-described procedures of cultivation to determine optimum concentrations; for example, a method, wherein cells are cultured in a $CO_2$ incubator aerated with 5% carbon dioxide at 37° C. for several hours, preferably for 2 hours, using a medium containing these anticancer agents at concentrations one-hundredth to one time the concentrations for living organisms specified in the Japanese Pharmacopoeia, is mentioned.

Any medium that allows cultivation of the differentiation-induced cells can be used here. Specifically, the aforementioned media and the like can be mentioned.

In transplantation therapy, graft rejection due to histocompatibility antigen differences is often problematic, which problem, however, can be solved by using a stem cell having the nucleus of a somatic cell transplanted thereto, or a stem cell having a modified gene on the chromosome thereof.

By inducing differentiation using a stem cell having the nucleus of a somatic cell transplanted thereto, cells, for example, nervous system cells and sensory system cells, of the individual which is the donor of the somatic cell can be obtained. Cells of such an individual are not only effective in transplantation medicine as they are, but also useful as a diagnostic material for determining whether or not an existing drug is effective on the individual. Furthermore, by culturing the differentiation-induced cells for a long period, it is possible to determine their susceptibility to oxidative stress and senescence; by comparing their functions or life spans with those of cells from other individuals, it is possible to evaluate the individual risks of contracting neurodegenerative and other diseases; these evaluation data are useful in providing an effective prophylactic method for diseases diagnosed as developing at high incidences in the future.

Cells, for example, nervous system cells, differentiation-induced from a stem cell by a method of the present invention can be transplanted to a diseased site of a patient by a method known per se (see, for example, Nature Neuroscience, 2, 1137(1999)).

(9) Formation of Cerebral Nerve Network

The present invention provides a method of forming a cerebral cortical nerve network in vitro, comprising the step (3). According to this method, it is possible to allow cell aggregates obtained by the SFEBq method to form a cerebral cortical nerve network therein without becoming a disarrayed cell masses.

The construction of a cerebral cortical nerve network in the cell aggregate in vitro can be confirmed by, for example, imaging analysis with calcium release as an index. Here, "in vitro" merely refers to being not in a living organism.

In the cerebral cortical nerve network formed by a method of the present invention, an elevation of $Ca^{2+}$ (calcium oscillation) synchronized or non-synchronized with surrounding cells is repeatedly observed in many cells. Hence, the cerebral cortical nerve network formed by the method of the present invention preferably can be accompanied by synchronized spontaneous firing. Here, "firing" refers to an excitatory activity due to depolarization of nerve cells, and "spontaneous firing" refers to firing that occurs spontaneously. Hence, the cerebral cortical nerve network formed by the method of the present invention can cause nerve activities similar in a certain aspect to the living tissue.

According to the present invention, a culture product as obtained by a method of the present invention, specifically cell aggregates that constitute the above-described cerebral cortical nerve network, is provided. This culture product (cell aggregate) has formed a nerve network that is extremely similar to the nerve network in a living organism, so that it can be used for screening for therapeutic drugs for diseases based on disorders of nervous system cells, for example, forebrain nerve cells, screening for therapeutic drugs for cell injuries due to other causes, or toxicity studies thereof and the like. Here, examples of diseases based on disorders of nervous system cells include Parkinson's disease, spinocerebellar degeneration, Huntington chorea, Alzheimer's disease, ischemic cerebral diseases (for example, cerebral stroke), epilepsy, brain traumas, spinal injuries, motor nerve diseases, neurodegenerative diseases, pigmentary degeneration of the retina, age-related macular degeneration, cochlear hearing loss, multiple sclerosis, amyotrophic lateral sclerosis, diseases caused by neurotoxic disorders, and the like. Specifically, diseases based on disorders of forebrain nerve cells, particularly of cerebral nerve cells, include, for example, Huntington chorea, Alzheimer's disease, ischemic cerebral diseases (for example, cerebral stroke), and brain traumas.

The culture product (cell aggregate) can also be used as a therapeutic drug for a disease based on a disorder of nervous system cells, for example, forebrain nerve cells, a therapeutic drug for cell injuries due to other causes, and the like.

(10) Formation of Cerebral Cortical Tissue Structure

The present invention provides a method of forming a steric structure of a brain tissue in vitro, comprising the step (3). According to this method, it is possible to allow cell aggregates obtained by the SFEBq method to form a steric structure of a brain tissue therein without becoming a disarrayed cell mass. More preferably, it is possible to mimic the initial process of the histogenesis of cerebral cortex in ongoing self-assembly, in the same order as with the cerebral cortical layers noted in the early cerebral primordium.

The construction of a steric structure of a brain tissue in the cell aggregates in vitro can be confirmed by, for example, the expression of layer-specific nerve cell markers such as Pax6 and Tbr1, light or electron microscopic morphological analysis, live imaging of GFP-transferred cells and the like. Here, "in vitro" has the same meaning as the above. The brain tissue is not particularly limited; all structures of the tissue that constitute the brain can be formed, but the brain tissue is preferably cerebral tissue, more preferably cerebral cortical tissue.

According to the present invention, a culture product as obtained by a method of the present invention, specifically cell aggregates that constitute a steric structure of a brain tissue, is provided (hereinafter, the cell aggregates that form a cerebral nerve network, obtained in (9), the cell aggregates that constitute a steric structure of a brain tissue, obtained in (10), and the cell aggregates with a structure having histological features similar to those of the fetal brain vesicles, obtained in (11), are described together as "the culture product of the present invention"). The culture product of the present invention has formed a brain tissue that is extremely similar to the early process of the histogenesis of cerebral cortex, so that it can be used for screening for therapeutic drugs for diseases based on disorders of nervous system cells, for example, forebrain nerve cells, screening for therapeutic drugs for cell injuries due to other causes, or toxicity studies thereof and the like. Here, examples of diseases based on disorders of nervous system cells include Parkinson's disease, spinocerebellar degeneration, Huntington chorea, Alzheimer's disease, ischemic cerebral diseases (for example, cerebral stroke), epilepsy, brain traumas, spinal injuries, motor nerve diseases, neurodegenerative diseases, pigmentary degeneration of the retina, age-related macular degeneration, cochlear hearing loss, multiple sclerosis, amyotrophic lateral sclerosis, diseases caused by neurotoxic disorders, and the like. Specifically, diseases based on disorders of forebrain nerve cells, particularly of endbrain nerve cells, include, for example, Huntington chorea, Alzheimer's disease, ischemic cerebral diseases (for example, cerebral stroke), and brain traumas.

The culture product of the present invention can also be used as a therapeutic drug for a disease based on a disorder of nervous system cells, for example, forebrain nerve cells, a therapeutic drug for cell injuries due to other causes, and the like.

(11) Promotion of Formation of Epithelial Structure in Cerebral Cortical Tissue

By adding an extracellular matrix component to the medium in the above-described suspension culture, the epithelium structure of cerebral cortical tissue is stably maintained for a longer period than without addition of the component, and a structure having histological characteristics similar to those of the fetal brain vesicles is obtained.

Similarity to the fetal brain vesicles can be judged with the following characteristics as indexes: 1) a high density of radial glia cells, 2) retention of a laminin-positive continuous basal membrane, 3) an end foot structure seen in the basal membrane adhesion part of radial glia cells. Radial glia can be detected with BLBP as a marker.

"An extracellular matrix component" refers to one of various components usually found in the extracellular matrix. In a method of the present invention, it is preferable to use a basal membrane component. Examples of the major components of the basal membrane include type IV collagen, laminin, heparan sulfate proteoglycan, and entactin.

As extracellular matrix components added to the medium, commercial products can be utilized; examples include Matrigel (BD Bioscience), human type laminin (Sigma) and the like.

Matrigel is a basement membrane preparation derived from Engelbreth Holm Swam (EHS) mouse sarcoma. The major components of Matrigel are type IV collagen, laminin, heparan sulfate proteoglycan, and entactin; in addition, TGF-β, fibroblast growth factor (FGF), tissue plasminogen activator, and the growth factor naturally produced by EHS tumors are also contained.

Growth factor reduced products of Matrigel have lower concentrations of growth factors than in ordinary Matrigel; the standard concentrations thereof are <0.5 ng/ml for EGF, <0.2 ng/ml for NGF, <5 µg/ml for PDGF, 5 ng/ml for IGF-1, and 1.7 ng/ml for TGF-β. In a method of the present invention, it is preferable to use a growth factor reduced product.

The concentration of the extracellular matrix added to the medium for suspension culture is not particularly limited, as far as the epithelial structure of cerebral cortical tissue is stably maintained; when using Martigel, it is added preferably in a volume $1/500$ to $1/20$, more preferably $1/100$, of the volume of the culture broth. Although the extracellular matrix component may be added to the medium already at the start of culturing the stem cell, it is added to the medium preferably at a time within several days after the start of suspension culture (for example, 1 day after the start of suspension culture).

(12) Screening Method

The present invention provides screening method of a test substance, comprising using a cell culture of the present invention or a culture product of the present invention. Particularly, a culture product of the present invention has an already formed nerve network that is extremely similar to a living nerve network, and also has an already formed brain tissue that is extremely similar to the initial process of the histogenesis of cerebral cortex, so that it can be applied for screening for therapeutic drugs for diseases based on disorders of nervous system cells, for example, forebrain nerve cells, screening for therapeutic drugs for cell injuries due to other causes, or toxicity studies thereof, and development of a new therapeutic method for diseases of nervous systems and the like.

Here, "a test substance" is exemplified by substances whose efficacy as therapeutic drugs for diseases of nervous systems is to be determined and substances that are therapeutic drugs for other diseases whose influences (for example, toxicity) on brain nerves must be determined. The substance may be any one of low-molecular compounds, high-molecular compounds, proteins, genes (DNA, RNA and the like), viruses and the like. Such substances can be chosen as appropriate by those skilled in the art.

The present invention is hereinafter described more specifically by means of the following Examples, which, however, are for illustrative purposes only and never limit the scope of the invention.

EXAMPLES

Example 1

Highly Efficient Differentiation Induction into Cerebral Cortex Progenitor Cells by the SFEBq Method (Method)

EB5 cells, which are mouse ES cells (E14-derived), or cells of an E14-derived cell line wherein the Venus gene, which is a modified GFP (green fluorescent protein), has been knocked in the cerebral nerve marker Bf1 gene as a nerve differentiation reporter by homologous recombination (hereinafter described as "Bf1/Venus-mES cells"), were cultured as described in the literature (Watanabe et al., Nature Neuroscience, 2005), and used in the experiments.

The medium used was a G-MEM medium (Invitrogen) supplemented with 1% fetal calf serum, 10% KSR (Knockout Serum Replacement; Invitrogen), 2 mM glutamine, 0.1 mM non-essential amino acids, 1 mM pyruvic acid, 0.1 mM 2-mercaptoethanol and 2000 U/ml LIF. For nerve differentiation induction by suspension culture, ES cells were monodispersed using 0.25% trypsin-EDTA (Invitrogen), and suspended in 150 µl of the differentiation medium on a non-cell-adhesive 96-well culture plate (SUMILON Spheroid plate, Sumitomo Bakelite Company) at $3 \times 10^3$ cells per well to allow aggregates to be formed quickly, after which the plate was incubated at 37° C., 5% $CO_2$ for 7 days (SFEBq method; FIG. 1A).

The differentiation medium used in this operation was a serum-free medium prepared by adding 10% KSR, 2 mM glutamine, 1 mM pyruvate, 0.1 mM non-essential amino acids, 0.1 mM 2-ME, 250 µg/ml of recombinant human Dkk-1, and 1 µg/ml of recombinant human Lefty-1 to G-MEM medium (see Watanabe et al., Nature Neuroscience, 2005).

The aggregate masses were recovered in a 6 cm non-adhesive plastic dish (3.5 ml of differentiation medium), and continued to be suspension-cultured for 3 days (10 days in total), after which the differentiation status was analyzed by fluorescent immunostaining. The results are shown in FIG. 1.

(Results)

The immunostaining analysis revealed that 10 days after the start of differentiation culture, about 70% of the cells in the aggregates expressed the cerebrum-specific marker Bf1. Also, 90% of the Bf1-positive cells expressed the cerebral cortex-specific marker Emx1. Also when differentiated Bf1/Venus-mES cells were analyzed by the expression of Venus-GFP, about 70% of the cells were positive, the majority of which expressed Emx1 (FIG. 1A). Hence, the SFEBq method enables cerebral cortex cells (progenitor cells) to be differentiation-induced with high efficiency when using the above-described differentiation medium. When using a conventional method wherein aggregates of ES cells are gradually formed using a 10 cm culture dish (Watanabe et al., Nature Neuroscience, 2005), Bf1-positive cells accounted for up to 30%, of which less than 40% became positive for the cerebral cortex marker Emx1. The presence of an epithelium-like structure with polarity in the aggregates was confirmed by the expression of N-cadherin, CD-133, laminin and the like (FIG. 1B to G), electron microscopic observation of the morphology of tight junction (FIG. 1H, parenthesized), adherence junction (FIG. 1I, parenthesized) and the like, the formation of a rosette (FIG. 1J, FIG. 1K, dotted line indicates a rosette), the expression of polarity markers (FIG. 1L to O, dotted line indicates a rosette, asterisk indicates a lumen) and the like.

Hence, the SFEBq method, compared with the conventional method, promotes the differentiation of ES cells into the cerebrum, particularly into cerebral cortex, more efficiently.

Example 2

In Vitro Production of Cerebral Neurons from Cerebral Cortex Progenitor Cells Induced by the SFEBq Method (Method)

Figure 2:
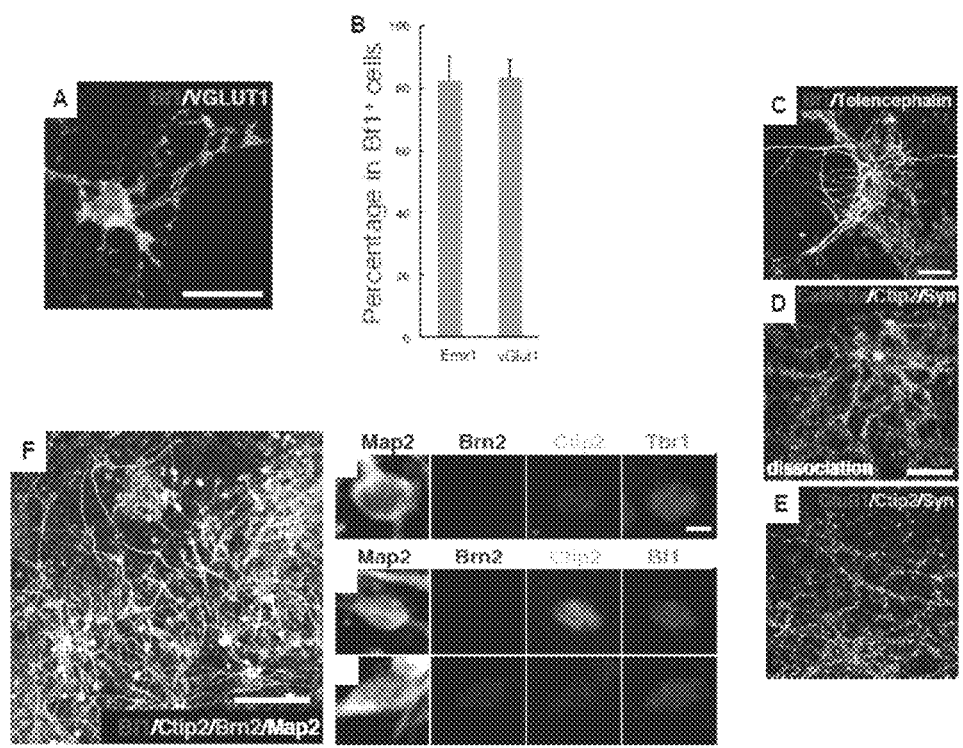

Aggregates obtained by continued differentiation culture by the method described in Example 1 for 12 days were enzymatically dispersed (SUMILON Neural Tissue Dissociation kit), plated in a culture plate coated with poly-D-lysine/laminin/fibronectin at $5 \times 10^4$ cells/cm$^2$, and cultured using a DMEM/F12 medium supplemented with 1×N2 supplement and 10 ng/ml of FGF2 for 2 days. Subsequently, the cells were further cultured using a Neurobasal medium supplemented with B27 supplement+50 ng/ml BDNF+50 ng/ml NT3 for 6 days. The properties of the differentiated neurons were analyzed by a fluorescent immunostaining method. The results are shown in FIG. 2.

(Results)

Most of the cells in the test tube became TuJ1-positive neurons, of which 80% were positive for the cerebral cortex-specific marker Emx1 and positive for the glutamatergic neuron (abundantly present in cerebral cortex) marker VGluT1 (FIG. 2A to B). Also observed was the expression of a plurality of nerve markers characteristic of cerebral neurons (Telencephalin, GluR1, CamKII, Ctip2, Tbr1 and the like) (FIG. 2C to F).

Hence, differentiation of cerebral cortex progenitor cells induced by the SFEBq method into cerebrum-specific neurons was confirmed.

Example 3

Formation of Nerve Network by Cerebral Neurons Produced by the SFEBq Method (Method)

To confirm the activities and network formation of cerebral neurons produced by the SFEBq method, an analysis was performed by a Ca$^{++}$ imaging method using fluo4-AM. The method of examination was as described in the literature (Ikegaya et al, 2005, Neurosci. Res., 52, 132-138).

Figure 3:
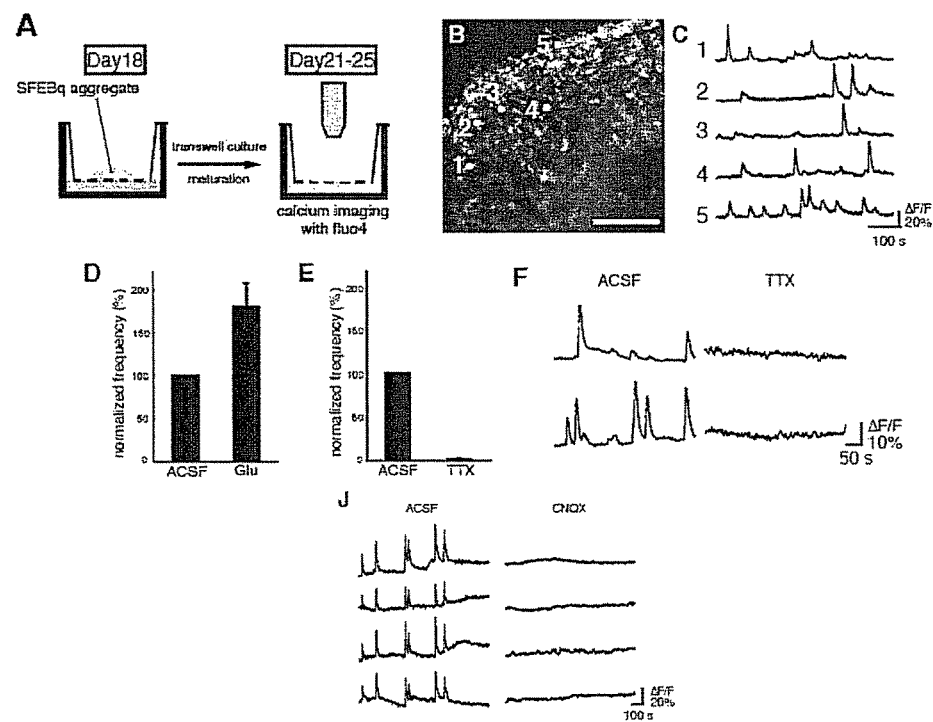
Figure 1:
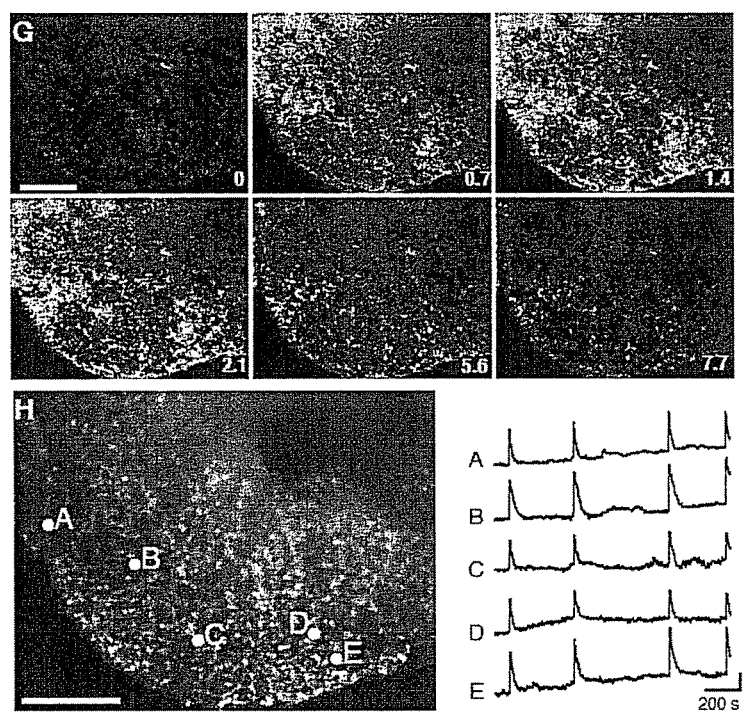
Figures 2, 3:
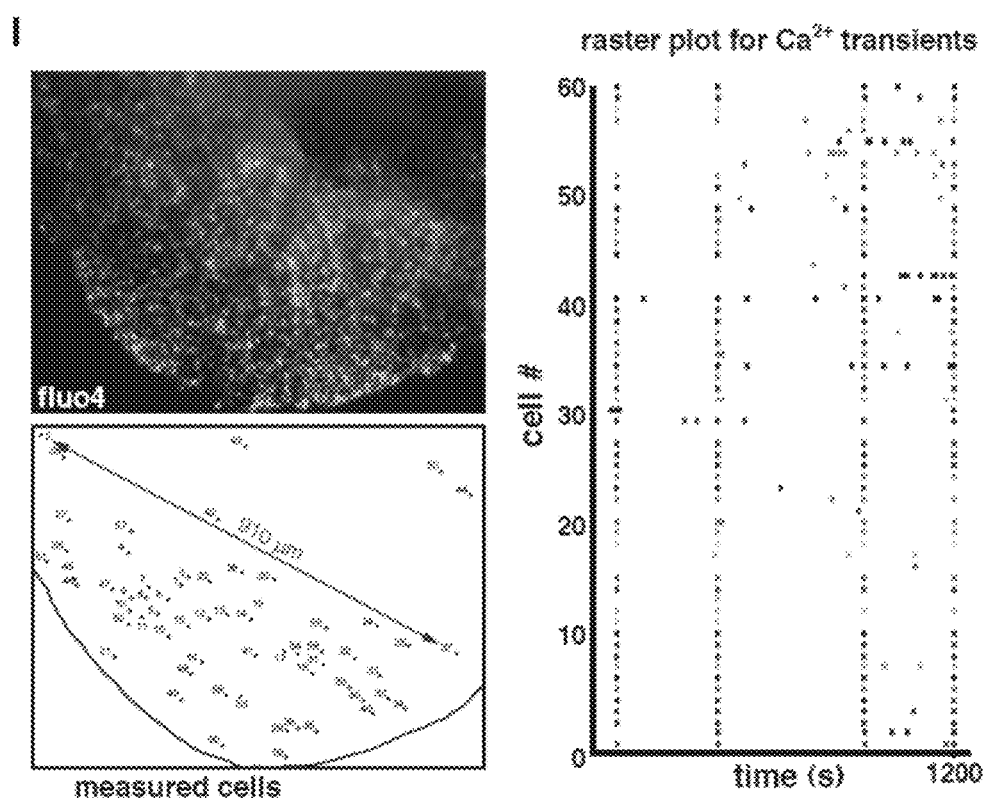

Aggregate masses derived from a mouse ES cell cultured by the method described in Example 1 for 18 days were further cultured on the Transwell culture insert (Corning) using a DMEM/F12 medium supplemented with N2 for 7 days (FIG. 3A). Ca$^{++}$ imaging was performed at room temperature using an artificial cerebrospinal fluid. The results are shown in FIG. 3.

(Results)

In the Ca$^{++}$ imaging, many cells exhibited repeatedly observable Ca$^{++}$ elevations synchronized or not synchronized with surrounding cells (FIG. 3B to C). Since all these Ca$^{++}$ elevations were enhanced by administration of glutamine (FIG. 3D) and inhibited by the addition of tetrodotoxin, which causes a blockade of nerve action potentials (FIG. 3E to F), it was suggested that the elevations were due to a neurotransmission-dependent network. In 70% of the aggregate masses, repeated activities of Ca$^{++}$ elevations synchronized at a high transmission speed (1 mm/second or more) over a long distance of 1 mm (Ca$^{++}$ oscillation) were observed (FIG. 3G to I; in FIG. 3H, codes A to E indicate individual cells, and in FIG. 3I, numerical figures also indicate individual cells.). All these elevations of Ca$^{++}$ are inhibited by the addition of the glutamine antagonist CNQX (FIG. 3J) or tetrodotoxin.

The results above show that SFEBq-derived cerebral tissue exhibits nerve activities similar to those of living tissue (at least in a certain aspect).

Example 4

Integration of Cerebral Neurons Produced by the SFEBq Method in Cerebral Tissue (Method)

Bf1/Venus-mES cells were prepared by a method described in the literature (Nature Biotech., 20, 87-90). After Bf1/Venus-mES cells were cultured by the method described in Example 1 for 14 days, the resulting Venus-positive cell mass was used for the experiment described below. Cerebral slice tissue from a mouse at 14.5 days of fetal development or 1 day after birth was brought into contact with a Venus-positive cell mass by placing the cell mass in the cerebral ventricle portion (FIG. 4A), and co-cultured on a Transwell filter for 3 days.

Figure 4:
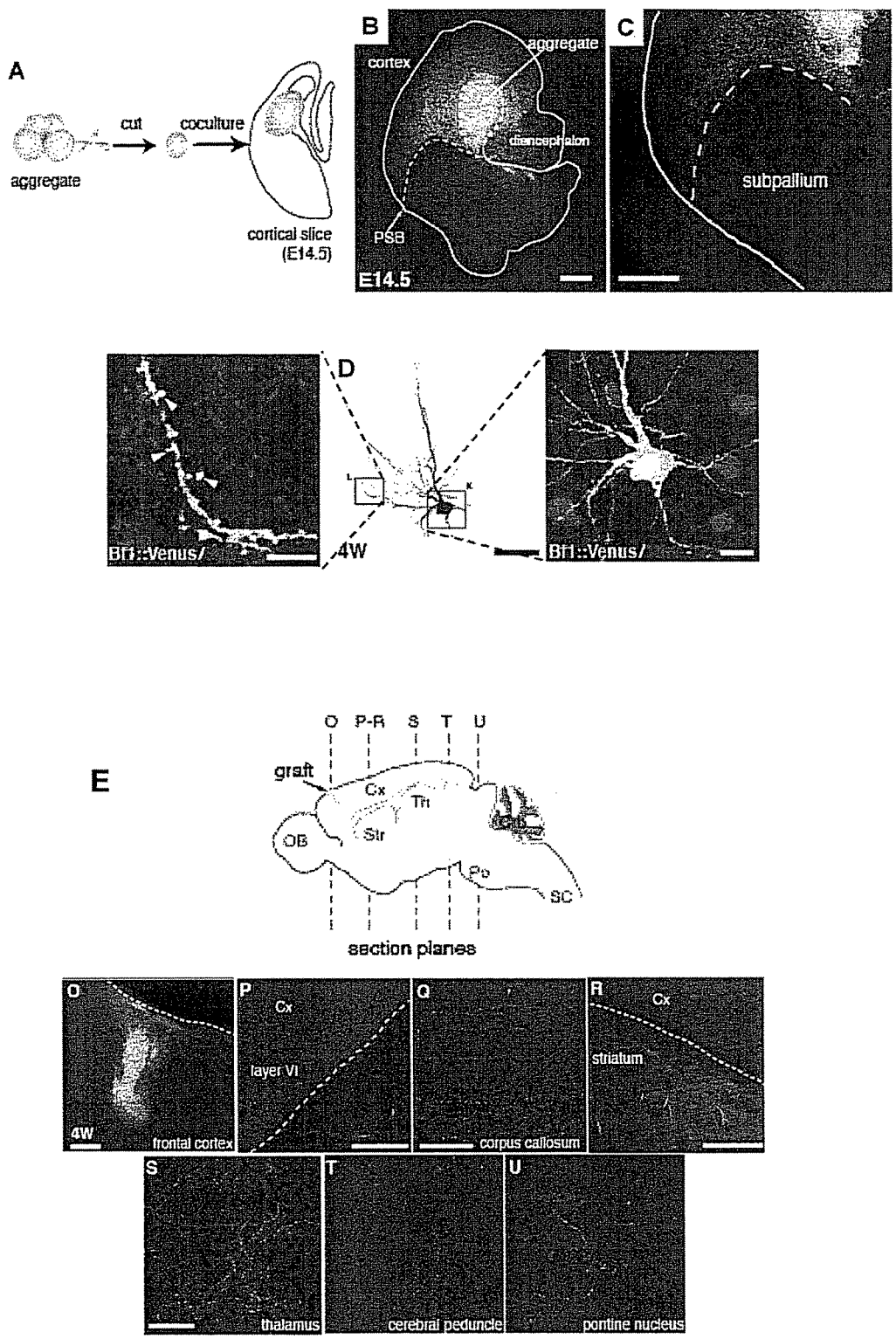
FIGS. 4A-E show that cerebral neurons obtained by the SFEBq method are integrated in cerebral tissue in vivo by placing the cell mass in the cerebral ventricle portion.

The venus-positive cell mass (after 11 days of differentiation culture) in the form of the mass as it is, or after being dispersed, was transplanted to the vicinity of the motor area of the cerebral cortex of a neonatal mouse in vivo, and histologically analyzed 4 weeks after the transplantation. The results are shown in FIG. 4.

(Results)

In the co-culture with the cerebral slice tissue from the mouse at 14.5 days of fetal development or 1 day after birth, a large number of Venus-positive nerve cells invaded cerebral cortical tissue from the Venus-positive cell mass (FIG. 4B to C). In the in vivo transplantation to the vicinity of the motor area of the cerebral cortex of the neonatal mouse, neurons that are morphologically similar to cerebral pyramidal cells differentiated from the dispersed and transplanted Venus-positive cells (FIG. 4D). From the cells that were transplanted in the form of the cell mass as it was, axonal projections to a broad range of brain tissues were noted; in particular, axonal projections from cerebral cortical neurons were prevalent; in the thalamus, striatum, cerebral peduncle, and pontine nucleus, many Venus-positive projections were confirmed (FIG. 4E; codes 0 to U; in FIG. 4E, Cx indicates cortex).

Example 5

Induction of Differentiation of Cerebral Cortical Layer-Specific Neurons from Cerebral Progenitor Cells Produced by the SFEBq Method (Method)

Figure 5:
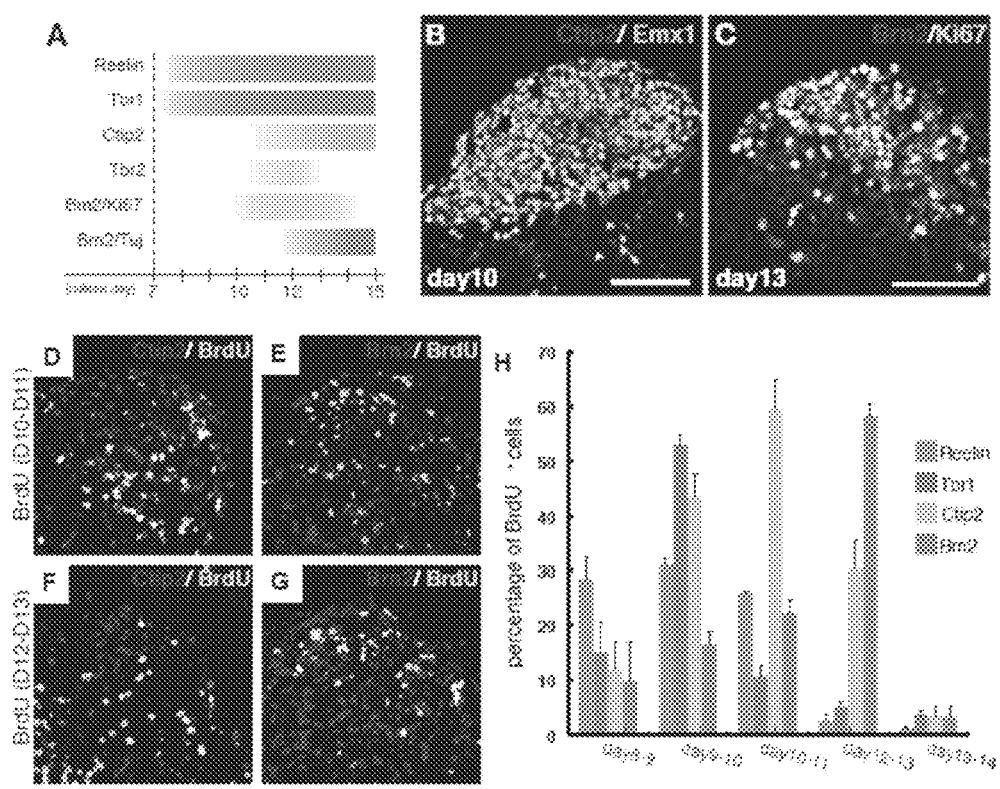
FIGS. 5A-H show that aggregates of ES cells obtained by the SFEBq method differentiate into cerebrum cortex layer-specific neurons via cerebral cortex progenitor cells.

Cells were cultured by the method described in Example 1 from day 17 to day 15, the expression of markers of cerebral cortical layer-specific neurons during that period was analyzed by a fluorescent immunostain method. The timing of final differentiation of layer-specific neurons (departing from the cell cycle) was analyzed by a birth-date analytical method based on a BrdU pulse label (Eur. N. Neurosci., 22, 331-342). The results are shown in FIG. 5.

(Results)

Cells that expressed Reelin, which is specific for the Cajal-Retzius cells of the 1st cerebral layer, emerged from day 7 of SFEBq culture. Tbr1/Bf1-positive cells specific for the 6th cerebral layer were also noted from day 7. Citp2-positive cells specific for the 5th cerebral layer significantly emerged from days 9-10 (FIG. 5B), and Brn2-positive neurons specific for the 2nd-3rd cerebral layers were significantly observed on days 11-12 (FIG. 5C). This order (FIG. 5A) agrees with the order of development of these cerebral layer-specific neurons in the developmental process. Their correlation was also confirmed by the birth-date analytical method based on the BrdU pulse label; it was confirmed that the cells departed from the cell cycle in the order of the 1st layer, 6th layer, 5th layer, and 2nd-3rd layers (FIG. 5D to H).

This shows that cerebral progenitor cells differentiated by the SFEBq method produce layer-specific neurons under temporal control similar to that for cerebral cortex in the developmental process, suggesting that these neurons have characters that are very similar to those of cerebral cortex progenitor cells in vivo.

Example 6

Preferential Induction of Differentiation into Particular Layer-Specific Neurons from Cerebral Progenitor Cells Produced by the SFEBq Method (Method)

Figure 6:
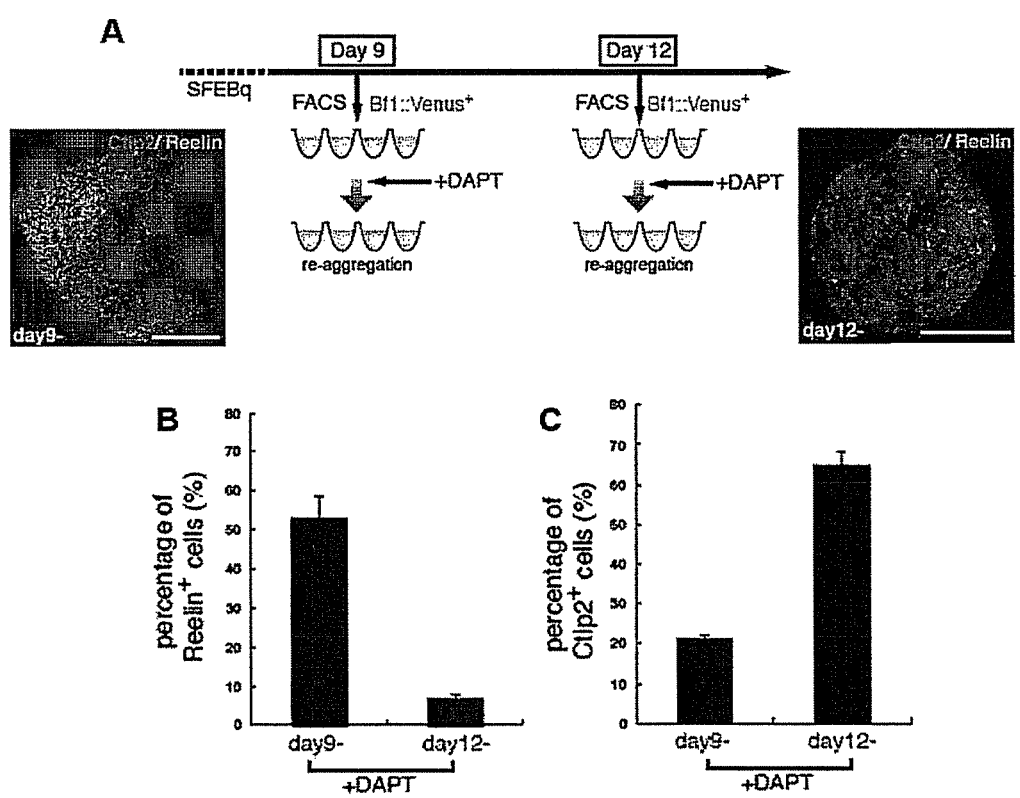
FIGS. 6A-C show that aggregates of ES cells obtained by the SFEBq method differentiate into particular layer-specific cerebral cortical neurons via cerebral cortex progenitor cells.

After Bf1/Venus-mES cells were cultured for differentiation for different lengths of periods (9 days or 12 days), the resulting Venus-positive cells were separated by FACS, and rapid re-aggregation (5000 cells/well) was performed using a non-cell-adhesive 96-well culture plate. Starting on the following day, rapid induction of differentiation into neurons was performed by a treatment with the Notch inhibitor DAPT (10 μM; known to promote neuron differentiation; Nelson et al, 2007); after further differentiation culture for 6 days, layer-specific markers were analyzed by a fluorescent immunostaining method (FIG. 6A). The results are shown in FIG. 6.

(Results)

With the DAPT treatment after 9 days of differentiation culture, more than 50% of the cells differentiated into Reelin-positive Cajal-Retzius cells (FIG. 6A, B). Meanwhile, with the DAPT treatment after 12 days of differentiation culture, more than 60% of the cells differentiated into Ctip2/Emx1-positive cerebral cortical neurons specific for the 5th layer, Reelin-positive cells accounting for less than 10% (FIG. 6A, C).

Hence, in the SFEBq method, it is possible to selectively produce cerebral neurons having different layer specificities by employing different culturing times and timing-specific Notch inhibition.

Example 7

In Vitro Induction of Differentiation into Cerebral Site-Specific Tissues from Cerebral Progenitor Cell Produced by the SFEBq Method (Method)

Figures 1, 7:
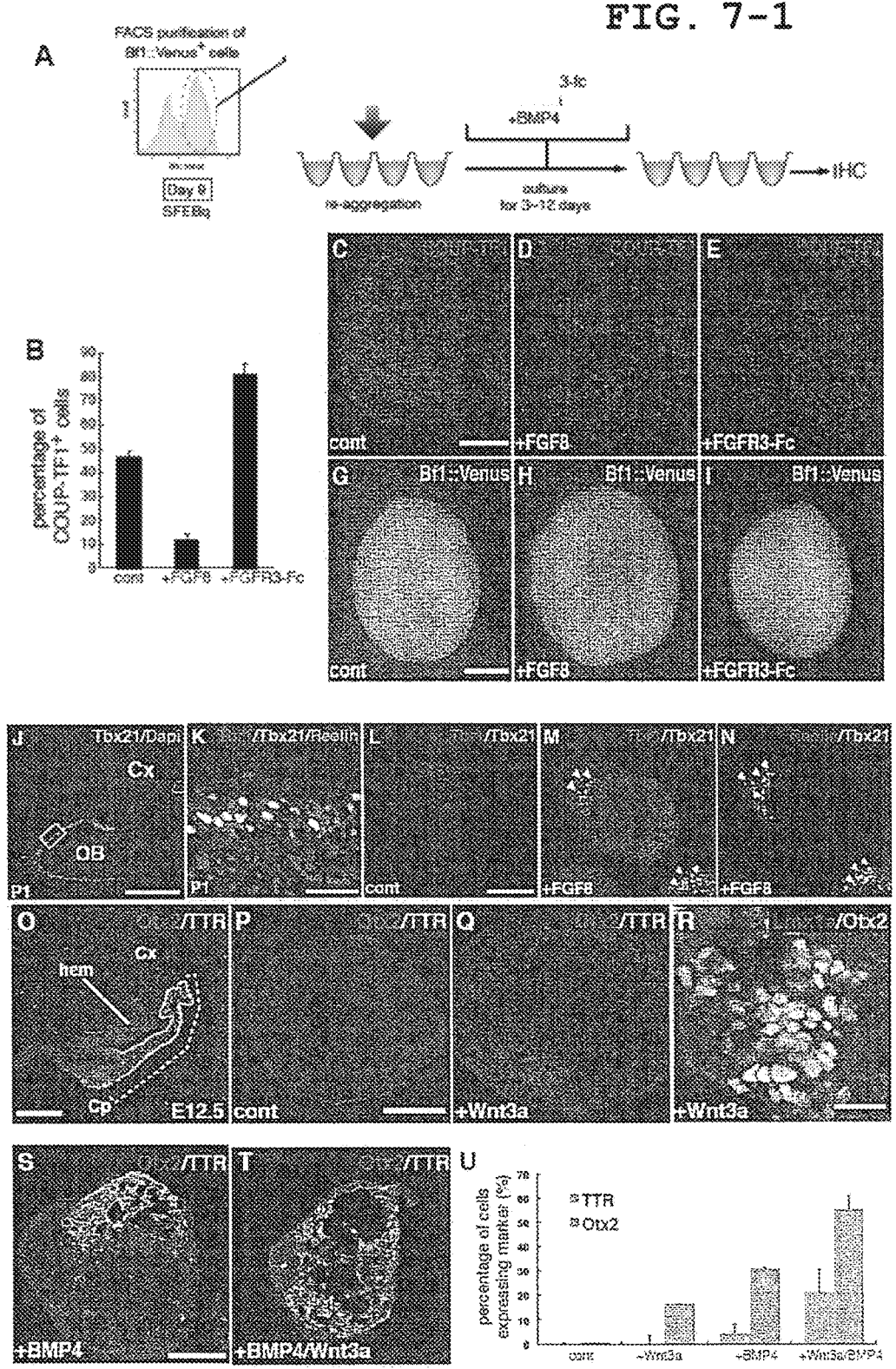
Figures 2, 7:
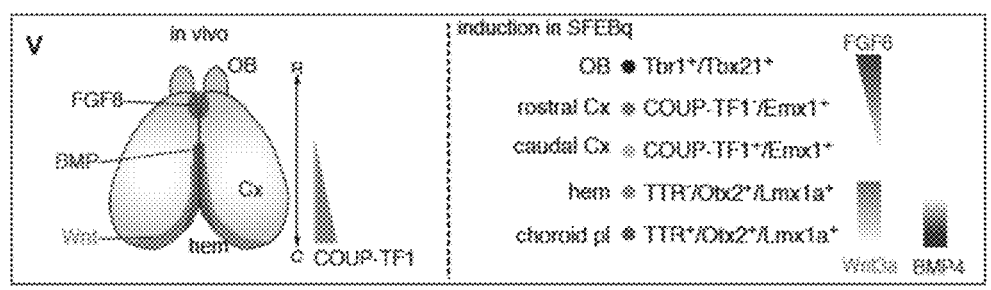

Bf1/Venus-mES cells were cultured for differentiation by the SFEBq method for 7 days, after which the resulting Venus-positive cells were separated by FACS, and rapid re-aggregation (5000 cells/well) was performed using a non-cell-adhesive 96-well culture plate. Secreted pattern formation factors such as Fgf 8b (50 ng/ml), the Fgf receptor inhibitor FGFR3-Fc (50 ng/ml), Wnt3a (20 ng/ml), and BMP4 (0.5 ng/ml) were added thereto, and the cells were cultured for 3 to 12 days. The expression of cerebral part-specific markers was analyzed by a fluorescent immunostain method (FIG. 7A). The results are shown in FIG. 7.

(Results)

In re-aggregate masses without addition of the pattern formation factors (after 3 days of re-aggregation culture), caudal cerebral cortex type cells (Coup-TF1$^+$/Bf1$^+$) and rostral cerebral cortex type cells (Coup-TF1$^-$/Bf1$^+$) each accounted for 50% of the cerebral tissue. Meanwhile, in the Fgf 8b addition group, 90% of the cells became cells of the rostral cerebral cortex type (Coup-TF1$^-$/Bf1$^+$); in the Fgf receptor inhibitor FGFR3-Fc addition group, 80% of the cells became cells of the caudal cerebral cortex type (Coup-TF1$^+$/Bf1$^+$) (FIG. 7B to I). This shows that cerebral cortical tissue induced by SFEBq can be selectively differentiation-induced into rostral or caudal cerebral cortical tissue, respectively, depending on the presence or absence of an Fgf signal.

When the cells were cultured for 12 days, only in the Fgf 8 addition group, significant differentiation of neurons of the olfactory bulb, which is one of the rostral cerebral tissues (Tbr21-positive), was observed (FIG. 7J to N; the arrowheads in FIG. 7M and FIG. 7N indicate cells that expressed TBx21.). This result also reveals the differentiation of rostral cerebral tissue by the Fgf signal.

In the Wnt3a addition group, induction of the expression of Otx2 and Lmxla, which are site-specific markers of the hem area (perihippocampal tissue) present in the most caudal and dorsal part of the cerebrum, was observed in 2-30% of the cells (FIG. 7O to R).

In the BMP4 addition group, in addition to the expression of Otx2 and Lmx1a, differentiation of choroidal tissue present in the most dorsal part of the cerebrum (TTR-positive) was noted (FIG. 7O, S). Particularly, in the Wnt3a+BMP4 addition group, this expression was enhanced, the expression of Otx2 and Lmx1a was noted in more than 50% of the cells, and the expression of TTR was noted in 20% of the cells (FIG. 7T to U).

These results show that by combining the SFEBq method and a Wnt signal and a BMP signal, induction of differentiation into the most caudal and dorsal tissue of the cerebrum is also possible from an ES cell (FIG. 7V).

Example 8

Formation of Cerebral Cortical Tissue Having a Laminar Structure from Cerebral Progenitor Cells Produced by the SFEBq Method (Method)

Figure 8:
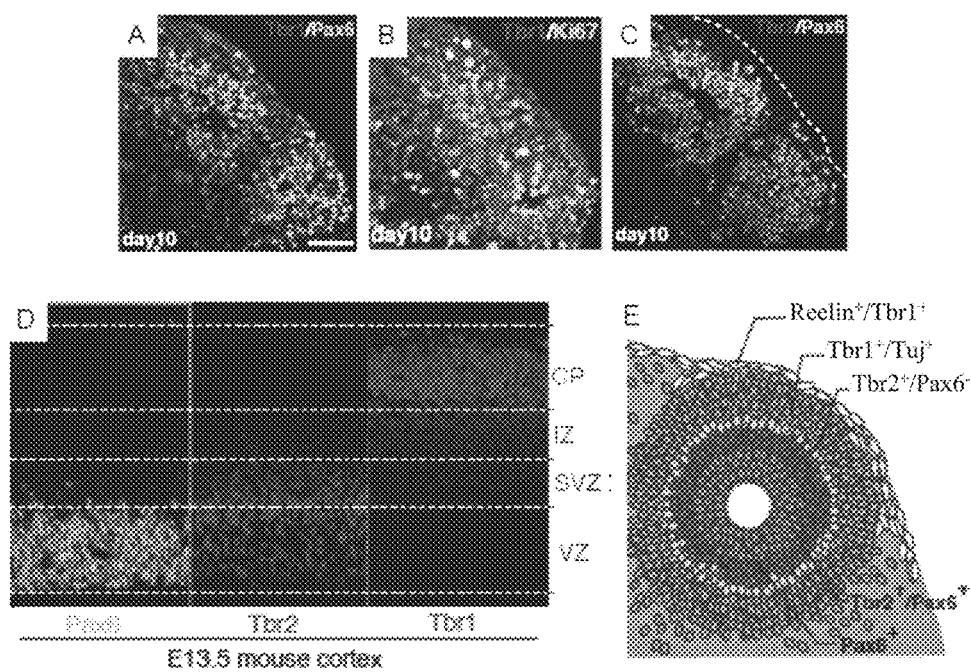
FIGS. 8A-E show that aggregates of ES cells obtained by the SFEBq method are capable of mimicking the self-assembly early foe nation of cerebral cortex like in vitro. Histological analysis after 10 days revealed that the innermost part of each rosette was occupied by a layer of Pax6/CD133/Ki67-positive nerve progenitor cells having the dividing capability, outside of which there was a layer like the cerebral plate (cortical plate) occupied by Tbr1- and Ctip2-positive neurons which are nerve cells of the 5th-6th layers of cerebral cortex (A and B). Spanning over these two layers, there was a layer of Tbr2-positive cells which are progenitor cells of neurons derived from the late cerebral plate (cortical plate) such as the 2nd-3rd layers of cerebral cortex (C). The order of these layers is the same as the order of layers noted in the early cerebral primordium (e.g., at 14 days of fetal development in mice) and marker expression pattern, showing that in the SFEBq method, the initial process of the histogenesis of cerebral cortex can be mimicked like a self-assembly in vitro (D and E).

Mouse ES cells were cultured by SFEBq culture by the method of Example 1 for 10 days, histogenesis and neuron production in suspended aggregate masses during that period were examined by fluorescent immunostaining. Tissue sections were prepared as frozen sections. For extensive analysis of early histological profiles, a transmission electron microscope was also used. The results are shown in FIG. 8 and the like.

(Results)

In the SFEBq culture, suspended aggregate masses were formed with a homogenous size, and the degree of differentiation was nearly constant among the different aggregate masses (FIG. 1A). Beginning at 3 to 4 days after the start of differentiation culture, accumulation of the nerve progenitor cell markers Sox1 and N-cadherin was noted (FIG. 1B to C); 5 days later, more than 90% of the cells expressed the nerve progenitor cell markers. 5 days later, the nerve progenitor cells histologically formed a monolayer columnar epithelium (nerve epithelium) in continuity, and this epithelium had a polarity wherein the inside thereof was the apical side with high reproducibility (FIG. 1D to F). 7-8 days later, the nerve epithelium divided itself into several spherical masses (rosette), which, however, still retained the polarity wherein the inside thereof was the apical side.

Histological analysis after 10 days revealed that the innermost part of each rosette was occupied by a layer of Pax6/CD133/Ki67-positive nerve progenitor cells having the dividing capability, outside of which there was a layer like the cerebral plate (cortical plate) occupied by Tbr1- and Ctip2-positive neurons which are nerve cells of the 5th-6th layers of cerebral cortex (FIG. 8A to B). Spanning over these two layers, there was a layer of Tbr2-positive cells which are progenitor cells of neurons derived from the late cerebral plate (cortical plate) such as the 2nd-3rd layers of cerebral cortex (FIG. 8C). Furthermore, outside of Tbr1- or Ctip2-positive neurons, a layer of Reelin-positive cells, which are neurons of the 1st layer of cerebral cortex, was often present. The order of these layers is the same as the order of layers noted in the early cerebral primordium (e.g., at 14 days of fetal development in mice) and marker expression pattern, showing that in the SFEBq method, the initial process of the histogenesis of cerebral cortex can be mimicked like a self-assembly in vitro (FIG. 8D to E).

Example 9

Production of Human ES Cell-Derived Cerebral Cortical Tissue and Neurons by the SFEBq/RI Method (Method)

Figure 9:
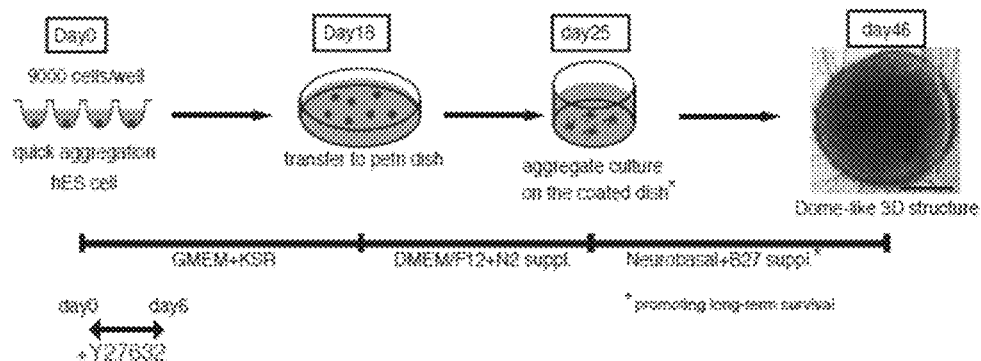
FIGS. 9A-J show that aggregates of human ES cells obtained by the SFEBq method differentiate into cerebral cortical neurons.
Figure 9:
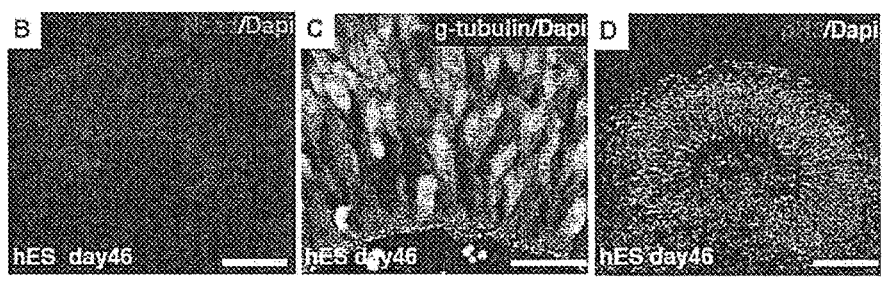
Figure 9:
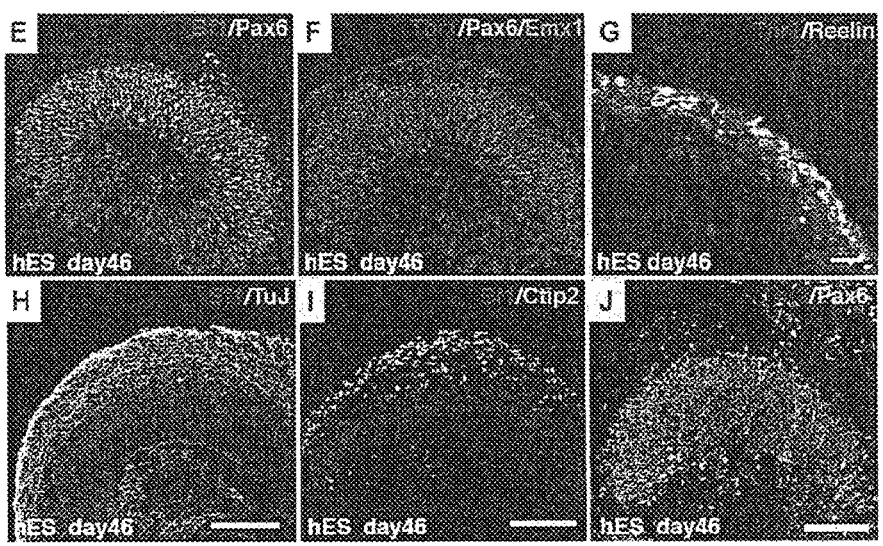

Human ES cells (KhES#1; established by Professor Nakatsuji at Kyoto University) were cultured for maintenance as described previously (Ueno et al., PNAS, 2006). Differentiation was induced with the addition of a ROCK inhibitor that had been reported by us to suppress cell death during dispersion suspension culture (Y-27632; Watanabe et al., Nature Biotechnology 2007), which was added to the medium from the start of cultivation (SFEBq/RI method). A G-MEM medium supplemented with 20% KSR, 10 µM Y27632, 2 mM glutamine, 1 mM pyruvic acid, 0.1 mM non-essential amino acids, 0.1 mM 2-mercaptoethanol, and 250 µg/ml recombinant Dkk-1 (500 ng/ml), and further supplemented with the Nodal inhibitor Lefty-A (5 µg/ml; R&D) and the BMP inhibitor BMPRFc (1.5 µg/ml; R&D), was used as a differentiation medium. Monodispersed human ES cells (Watanabe et al., Nature Biotechnology, 2007) were dispensed to a non-cell-adhesive 96-well culture plate at 9000 cells/150 µl/well in the same manner as Example 1, and suspension-cultured at 37° C., 5% $CO_2$ for 18 days. Subsequently, the suspended aggregate masses were recovered in a non-cell-adhesive 6 cm Petri dish (SUMILON Celli-tight-X), and further cultured using a DMEM/F12 medium supplemented with the N2 supplement for 7 days. The aggregate masses were further cultured on an 8-well chamber slide culture vessel coated with poly-D-lysine/laminin/fibronectin using a Neurobasal medium (containing 2 mM L-glutamine) supplemented with B27 supplement until a total of 46 days after the start of cultivation (FIG. 9A). The results are shown in FIG. 9.

(Results)

The cell aggregate masses derived from the human ES cell retained the dome-shaped steric structure even on the coated culture vessel (FIG. 9A). In more than 90% of the aggregate masses, Bf1/Emx1-positive cerebral cortex type nerve epithelium was present as a continuous tissue, and the nerve epithelium tissue had a polarity wherein the inside thereof was the apical side (FIG. 9B to D). Similar construction was noted in the same cultivation using human iPS cells (253G4; Nakagawa et al, 2008, Nature Biotechnology 26, 101-106).

Importantly, as with mouse ES cell-derived cerebral tissue, production of layer-specific cerebral neurons was noted, and, in addition, a similar laminar arrangement was noted in the neuron clusters in the cell aggregate masses. Specifically, in the innermost layer, Pax6-positive cerebral cortex progenitor cell tissue having the capability of division was present, outside of which there were neuron layers of the 5th-6th Tbr1-, Ctip2-positive cerebral cortical layers. Spanning over these layers, Tbr2-positive cell clusters, which are progenitor cells of neurons corresponding to the late cerebral plate (2nd-3rd layers), were present. Furthermore, outside of the Tbr1-, Ctip2-positive layers, there were Reelin-positive cells corresponding to the 1st cerebral layer (FIG. 9E to J).

These show that as with mouse ES cells, even with human pluripotent stem cells such as human ES cells, histogenesis, neuron production and the like can be achieved like self-assembly in vitro. This histogenesis of cerebral cortex type nerve epithelium is observable with a length of cultivation of about 8 weeks for human ES cells, suggesting that the human-derived cerebral tissue thus self-formed can be utilized for drug discovery research, toxicity research, drug effect research and the like.

Example 10

Induction of Differentiation of Cerebral Basal Nuclear Nerve Cells by Addition of Shh to Cerebral Progenitor Cells Produced by the SFEBq Method (Method)

Figure 10:
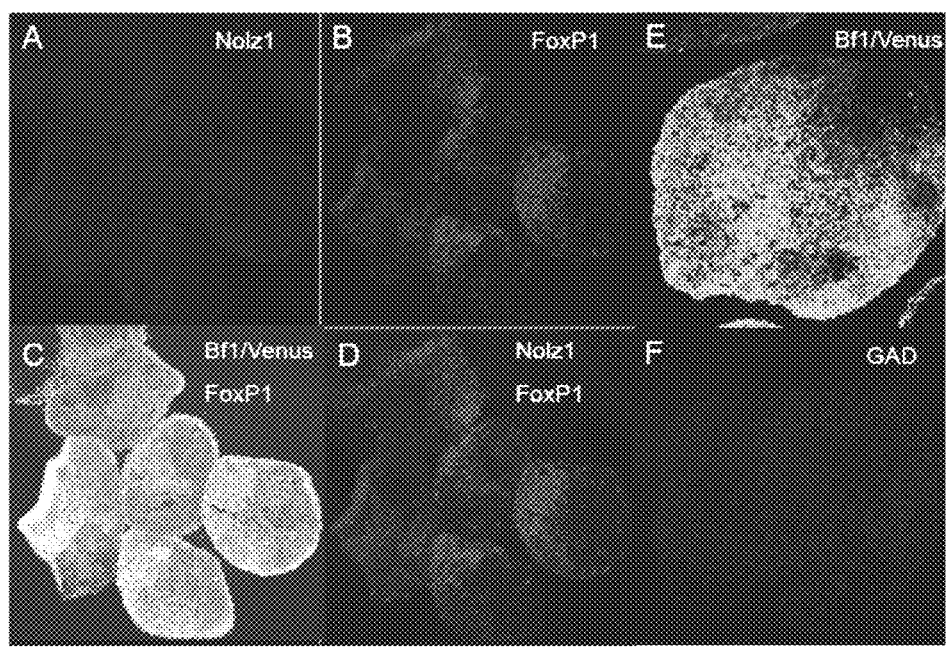
FIGS. 10A-F show that aggregates of ES cells obtained by the SFEBq method differentiate into cerebral basal nuclear nerve cells. When cultured with the addition of 6 nM Shh, 90% of the Bf1/Venus-positive aggregate masses expressed FoxP1 and Nolz1 17 days later (C). Out of them, Nolz1 (also expressed in striatal progenitor cells) was expressed in 50% of all cells (A), and FoxP1 (a marker of more mature striatal nerve cells) was expressed in 20-30% (B and D). These nerves expressed GAD, which is a GABA-acting neuron marker (E and F).

Bf1/Venus-mES cells were cultured for differentiation by the SFEBq method for 10 days. In this operation, during the first 6 days, the cells were cultured using a GMEM medium supplemented with the Wnt inhibitor Dkk1 (100 ng/ml) and 10% KSR; 3 days after the start of differentiation culture, 6 mM Shh protein was added to the medium. 6 days after the start of differentiation culture, the medium was replaced with a DMEM/F12 supplemented with 6 mM Shh and N2 supplement, and the cells were further suspension-cultured for 4 days. After the cells were cultured for a total of 10 days, the resulting Venus-positive cells were separated by FACS, and rapid re-aggregation (20000 cells/well) was performed using a non-cell-adhesive 96-well culture plate. The aggregate masses thus formed were further suspension-cultured using a DMEM/F12 medium supplemented with 6 mM Shh, N2 supplement and 10% bovine serum medium for 1 week, and immunologically stained with nerve markers (17 days in total). The findings were compared with those obtained without adding Shh, or those obtained with adding 30 nM Shh. The results are shown in FIG. 10.

(Results)

Striatal nerve cell markers derived from the cerebral basal dorsum (lateral basal nucleus prominence) in the genesis process include FoxP1 and Nolz1 and the like. When cultured with the addition of 6 nM Shh, 90% of the Bf1/Venus-positive aggregate masses (FIG. 10C) expressed FoxP1 and Nolz1 17 days later. Out of them, Nolz1 (also expressed in striatal progenitor cells) was expressed in 50% of all cells (FIG. 10A), and FoxP1 (a marker of more mature striatal nerve cells) was expressed in 20-30% (FIG. 10B, FIG. 10D). These nerves expressed GAD, which is a GABA-acting neuron marker (FIG. 10E, FIG. 10F). The expression of these markers was observed in less than 5% of all cells without addition of Shh.

Meanwhile, when the cells were cultured with the addition of 6 nM Shh, the expression of Nkx2.1, which is a marker of nerve cells that develop from the cerebral basal ventral part (medial basal nucleus prominence) (*pallidum* neurons, cerebral cortex intercalated neurons, striatum intercalated neurons and the like), was not noted. However, in the same cultivation with the addition of 30 nM Shh, the expression of Nkx2.1 was noted in 40% of the Bf1/Venus-positive aggregate masses.

These show that by adding a low concentration of Shh in SFEBq culture, striatal nerve cells that develop from the lateral basal nucleus prominence can be differentiation-induced, and that by adding a high concentration of Shh, nerve cells that develop from the more ventral medial basal nucleus prominence can be differentiation-induced.

Example 11

Selective Induction into Anterior Tissue and Posterior Tissue of Cerebral Cortical Tissue Derived from Human ES Cells by Fgf 8 Treatment (Method)

Figure 11:
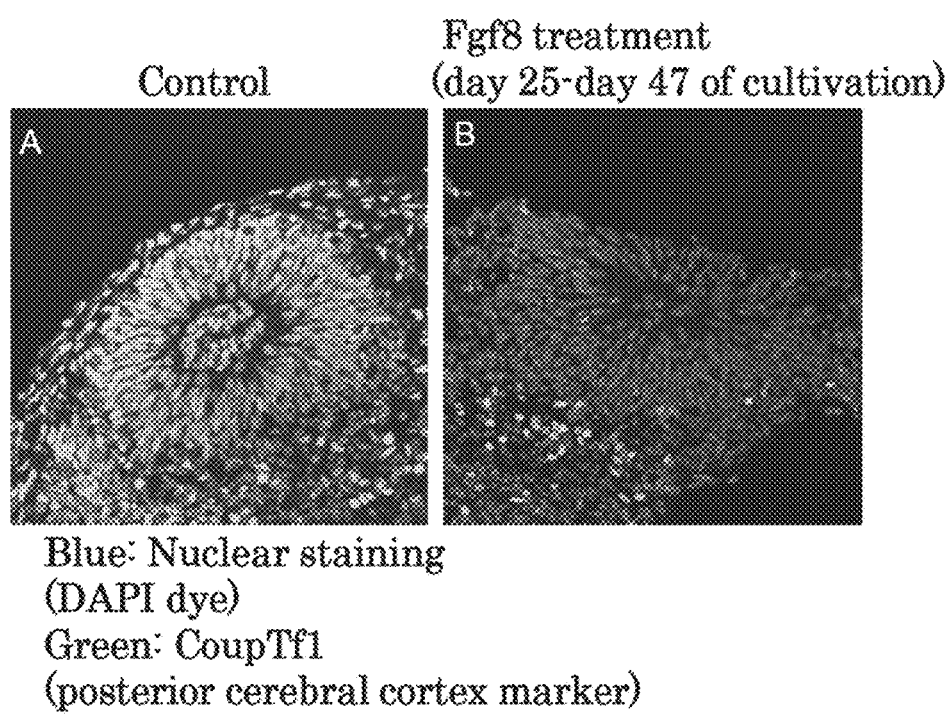
FIG. 11 B shows that, in the Fgf 8 addition group, CoupTf1-positive cells accounted for less than 20%, the majority being of the CoupTf1-negative anterior type.

Human ES cells were differentiated into cerebral cortical tissue in the same manner as Example 9; the tissue was cultured for 47 days, and thereafter fixed. In this cultivation, the Nodal receptor inhibitor SB431542, which is a low-molecular substance that, like Lefty-A, induces the cerebral marker Bf1 (10 μM), was used in place of the Nodal inhibitor Lefty-A. From 25 days after the start of differentiation culture, Fgf 8 (100 μg/ml) was added to the medium, after which the cells were cultured in the medium exchanged with the same medium but containing Fgf 8 every 3 days until day 47. For control, the medium was used without being supplemented with Fgf 8. Using CoupTf1, which is a posterior cerebral cortical tissue marker, the ratio of posterior cortex cells, which are positive for this marker, and anterior cortex cells, which are negative for the marker, was analyzed by immunostaining. The results are shown in FIG. 11.

(Results)

Whether or not Fgf 8 was added, more than 80% of the cells were positive for Bf1. In the control without the addition of Fgf 8, 80% of the Bf1-positive cells were of the CoupTf1-positive posterior type (FIG. 11A). Meanwhile, in the Fgf 8 addition group, CoupTf1-positive cells accounted for less than 20%, the majority being of the CoupTf1-negative anterior type (FIG. 11B).

The results above show that although many of the cells of the cerebral cortical tissue differentiated from human ES cells by the SFEBq method were of the posterior cortex cell type, as with the mouse cells in Example 7, selective differentiation into anterior cortex cells can be induced by the action of Fgf signals. By artificially regulating Fgf signals as described above, it is possible to selectively produce posterior cortex cells and anterior cortex cells from human pluripotent stem cells in vitro.

Example 12

Effect of Addition of Matrix Component in the SFEBq Method in Improving Nerve Differentiation from ES Cells and Nerve Tissue Construction (Method)

Sox1-GFP mES cells (mouse ES cells wherein GFP has been knocked in the early nerve marker gene Sox1 locus) were cultured for differentiation by the SFEBq method (a 96-well culture plate of low cell-binding ability). In this operation, 3-3000 cells per well were transplanted using the culture broth of Example 1. Starting 1 day later, to determine the effect of an extracellular matrix component, Matrigel (growth factor reduced grade; BD Bioscience; according to BD, of the primary protein components, 61% was laminin, 30% was collagen IV, and 7% was entactin) was added in a 1/100 amount per unit volume of the culture broth, and its effect was examined in terms of nerve differentiation and tissue construction.

(Results)

In the group of cells cultured only with the culture broth not supplemented with Matrigel, when the number of cells plated per well was 500-3000, 80% of the cells differentiated into Sox1-positive nerve progenitor cells after 5 days of cultivation. However, when the number of cells plated was 3-50, differentiation into Sox1-positive cells was not noted at all. However, in the Matrigel addition group, even when only 3-50 cells were plated, 90% of the cells differentiated into Sox1-positive cells. This means that even under conditions that are undesirable for nerve differentiation in SFEBq culture, the nerve differentiation is much improved by the addition of an extracellular matrix component to the culture broth. This showed that it is also possible to control nerve differentiation from a very small number, such as three, of ES cells with high reproducibility. (When 500-3000 cells were plated, with the addition of Matrigel, about 90% of the cells differentiated into nerve progenitor cells; in this case as well, a slight promoting effect was confirmed.)

More important are results of an observation of the tissue construction in the ES cell-derived nerve cell aggregate masses (2000 cells seeded per well). As shown in Example 8, 5-6 days later, whether Matrigel was added or not, the nerve progenitor cells histologically formed a monolayer columnar epithelium (nerve epithelium) in continuity, and the nerve epithelium tissue had a polarity wherein the inside thereof was the apical side with high reproducibility. In the Matrigel non-addition group, 7-8 days later, the nerve epithelium began to divide itself into several spherical small masses (rosettes); 10 days later, nerve epithelium in the form of one continuous bag was not noted at all.

Figure 12:
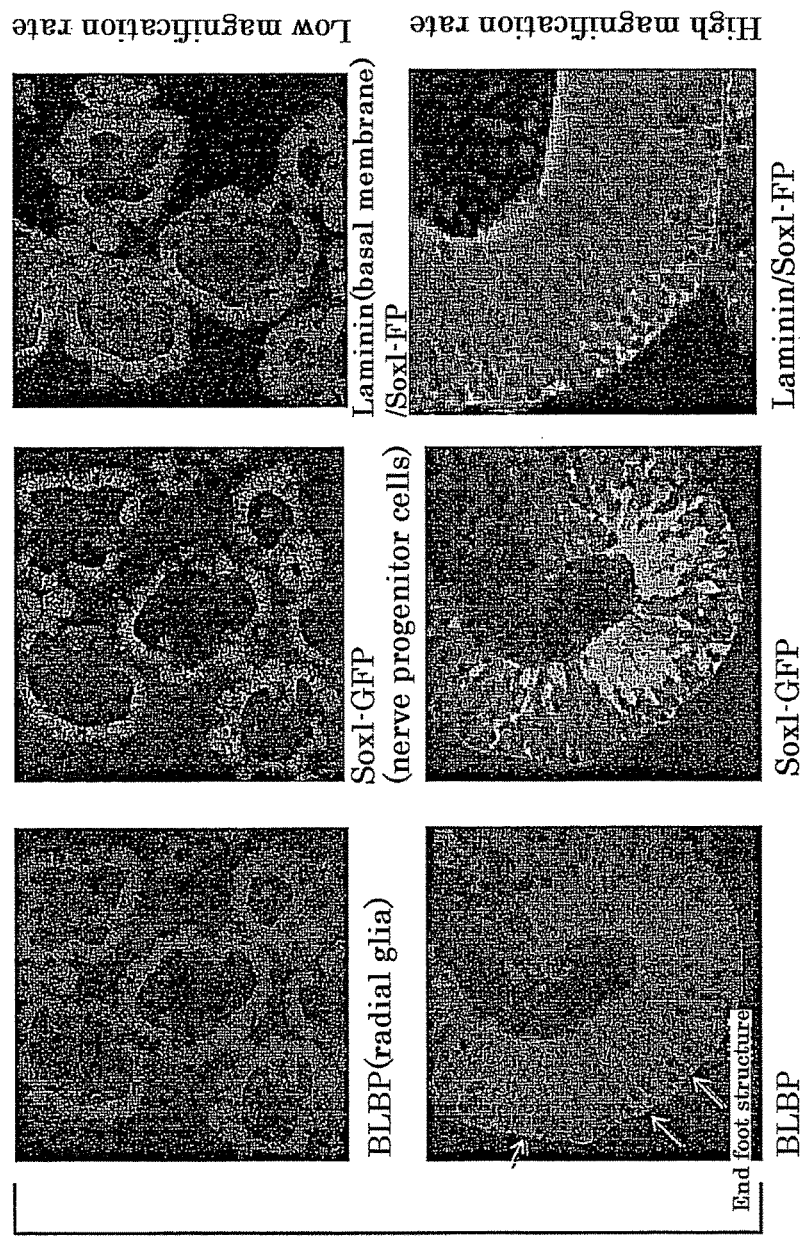
FIG. 12 are images showing that when an extracellular matrix component (Matrigel) is added to the medium at the stage of suspension culture, aggregates of ES cells obtained by the SFEBq method form structures similar to the fetal brain vesicles, and the structures are retained even until 10 days after the start of cultivation.

However, in the Matrigel addition group, even 10 days later, the nerve epithelium remained in the form of one continuous bag on the surfaces of the cell masses, and did not divide itself into rosettes. Unlike in the non-addition group, in the Matrigel addition group, after 10 days, the nerve epithelium was proven to have "histological characteristics that are more similar to fetal brain vesicles (nerve epithelium tissue of cerebral cortex)" such as 1) a high density of radial glia cells, 2) retention of a laminin-positive continuous basal membrane, and 3) an end foot structure seen in the basal membrane adhesion part of radial glia cells (FIG. 12).

This strongly suggests that by the addition of a matrix component to the culture broth, structures such as the basal membrane were fortified, the proliferation, maintenance and morphological retention of radial glia cells, which are primary structural component cells of nerve epithelium, were promoted, and epithelium structure formation in cerebral cortical tissue that mimics fetal brain vesicles was promoted.

Example 13

Differentiation Induction of Nerves from ES Cells by Suspension Culture of Mouse ES Cells Using a Chemically Synthesized Medium that does not Contain Growth Factors (SFEBq/gfCDM Method)

(Method)

Mouse ES cells (EB5 and Sox1-GFP ES cells) were cultured for maintenance as described previously (Watanabe et al. Nature Neuroscience, 2005: Non-Patent Document 4). The medium used was a G-MEM medium (Invitrogen) supplemented with 1% fetal calf serum, 10% KSR (Knockout Serum Replacement; Invitrogen), 2 mM glutamine, 0.1 mM non-essential amino acids, 1 mM pyruvic acid, 0.1 mM 2-mercaptoethanol and 2000 U/ml of LIF.

To induce the differentiation of nerves by suspension culture, ES cells were mono-dispersed using 0.25% trypsin-EDTA (Invitrogen), suspended in 150 µl of a differentiation medium to obtain a cell density of 3000 cells per well on a non-cell-adhesive 96-well culture plate (Lipidure-Coat, NOF Corp.), and incubated at 37° C., 5% $CO_2$ for 5 days.

The differentiation medium used was Iscove's Modified Dulbecco's Medium (IMDM)/Hams F12 1:1 (Invitrogen) supplemented with 1× Chemically-defined lipid concentrate (Invitrogen), monothioglycerol (450 µM; Sigma) and bovine serum albumin (a recrystallization-purified product of >99% purity; Sigma).

The addition or non-addition of human apo-transferrin (15 µg/ml; Sigma) did not influence any of the results shown below.

Differentiation into nerve progenitor cells was analyzed as described previously (Watanabe et al., Nature Neuroscience, 2005) by FACS using Sox1-GFP ES cells that emit fluorescence when differentiated into nerves. The FACS was performed using FACSAria (Beckton Dickenson) and its data were analyzed using FACSDiva software. Nerve differentiation was also analyzed by a fluorescent immunostaining method using EB5 cells.

(Results)

When a non-adhesive 96-well culture plate was used, most of the cells placed in one well formed one suspended aggregate mass with high reproducibility within half a day; even in cultivation with a chemically synthesized medium that does not contain growth factors, the cells grew well with little cell death noted. After 5 days of cultivation, the FACS analysis revealed that more than 90% of the cells became positive for Sox1-GFP. The fluorescent immunostaining method revealed that more than 90% of the cells were positive for the nerve marker N-cadherin. These results show that selective nerve differentiation can be induced from mouse ES cells under the above-described culturing conditions (SFEBq/gfCDM method).

Example 14

Induction of Differentiation of the Hypothalamus from Hypothalamic Progenitor Cells from ES Cells by the SFEBq/gfCDM Method and Effects of Various Growth Factors (Method)

Differentiation culture was performed under the same culturing conditions as Example 13 for 7 days. For analyzing the differentiated cells, an antibody against the Rx protein, which is a hypothalamic and retinal progenitor cell marker, was used. In hypothalamic progenitor cells, in addition to Rx, a protein called nestin is expressed, whereas in retinal progenitor cells, only Rx is expressed but nestin is not expressed, so that hypothalamic progenitor cells were identified by a fluorescent immunostaining method with the co-expression of Rx and nestin as an index.

Furthermore, EB5 cells wherein GFP was knocked in at the Rx gene locus (hereinafter, Rx-GFP ES cells) were prepared, and the expression of Rx-GFP was also analyzed by FACS.

In FACS-fractionated Rx-GFP$^+$ ES cells, the expression of Otx2, Rx, Six3, Vax1, Irx3, En2 and Hoxb9 was confirmed.

(Results)

Figure 13:
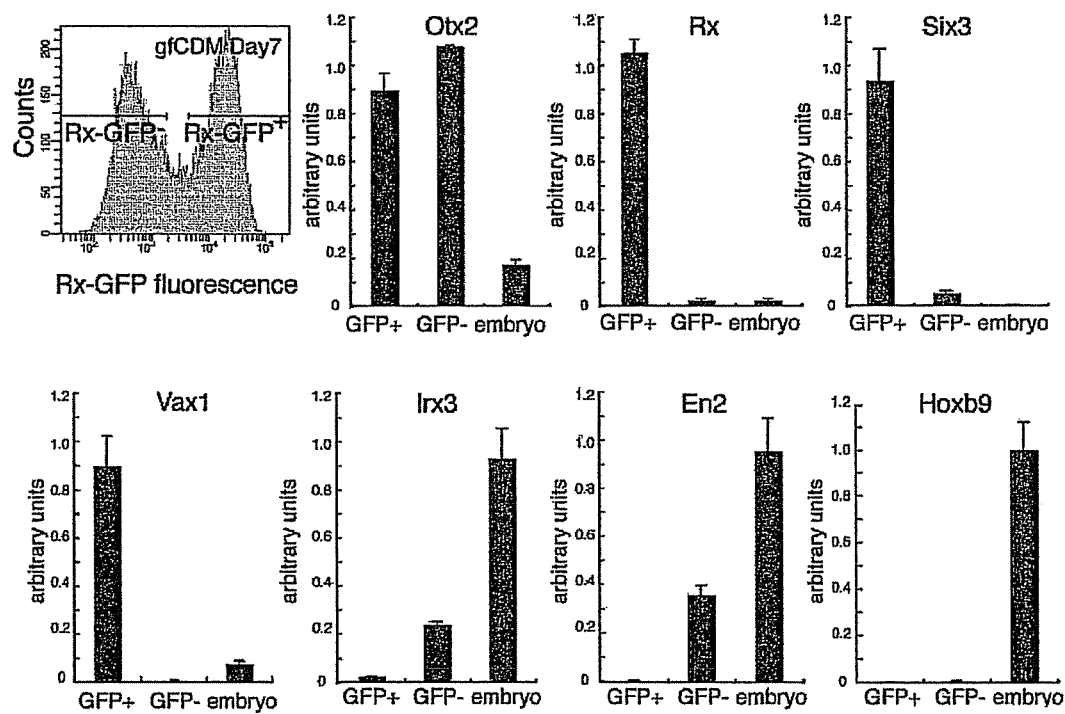
FIG. 13 are images showing the results of a qPCR analysis of the expression of the indicated marker genes in Rx-EGFP cells cultured by SFEBq.

When EB5 cells and Sox1-GFP ES cells were cultured for differentiation by the SFEBq/gfCDM method for 7 days, after which the aggregate masses were prepared as frozen sections, and histologic staining was performed by a fluorescent immunostaining method, 45-65% of the cells were positive for Rx. All of these Rx-positive cells were positive for nestin. For the results for other markers, see FIG. 13.

This suggests that by cultivation by the SFEBq/gfCDM method, selective differentiation of mouse ES cells into hypothalamic progenitor cells can be induced.

Even in the SFEBq/gfCDM culture of Rx-GFP ES cells, high differentiation efficiencies of 50-70% were confirmed. With this as an index, the effects of various growth factors were examined. When each of Nodal (1 µg/ml), Wnt3a (200 ng/ml), Fgf 8b (250 ng/ml), BMP7 (500 ng/ml), retinoic acid (0.2 µM), and lipid-rich albumin (1×; Invitrogen) was added to the medium from day 3 to day 7, all lowered the percentage of Rx-GFP to less than 10%. Conversely, addition of Shh-N (30 µM) elevated the percentage of Rx-GFP to about 80%. Meanwhile, also by supplementary addition of sodium selenite to the differentiation medium (the concentration in the differentiation medium was initially 0.017 mg/L, and this was increased to 0.025 mg/L), the percentage of Rx-GFP could be raised to about 80%. These findings show that the absence of growth factors/additives that are often added to serum-free medium, such as Nodal, Wnt3a, Fgf 8b, BMP7, retinoic acid, and lipid-rich albumin, is important to differentiation into hypothalamic progenitor cells from ES cells. Conversely, it was also suggested that addition of Shh or an increase in the amount of sodium selenite is effective in promoting the differentiation into hypothalamic progenitor cells moderately.

Example 15

Effects of Insulin and Akt Inhibitor on Differentiation of Hypothalamic Progenitor Cells by the SFEBq/gfCDM Method (Method)

Differentiation culture was performed under the same culturing conditions as Example 14 for 7 days, and the influence of the addition of insulin to the medium on the differentiation of hypothalamic progenitor cells from ES cells was analyzed by FACS using Rx-GFP ES cells. The intracellular signal transduction of insulin is involved by roughly two pathways (MAPK pathway and PI3K-Akt pathway). Hence, the effects of PD98059, which inhibits MAPK, LY294002, which inhibits PI3K, and Akt inhibitor VIII (Calbiochem), which is an inhibitor of Akt, a factor further downstream of PI3K, on the differentiation into hypothalamic progenitor cells, were likewise examined. LY294002, Akt inhibitor VIII, PD98059 or DMSO (vehicle control) was added on day 2 of cultivation.

(Results)

Figure 14:
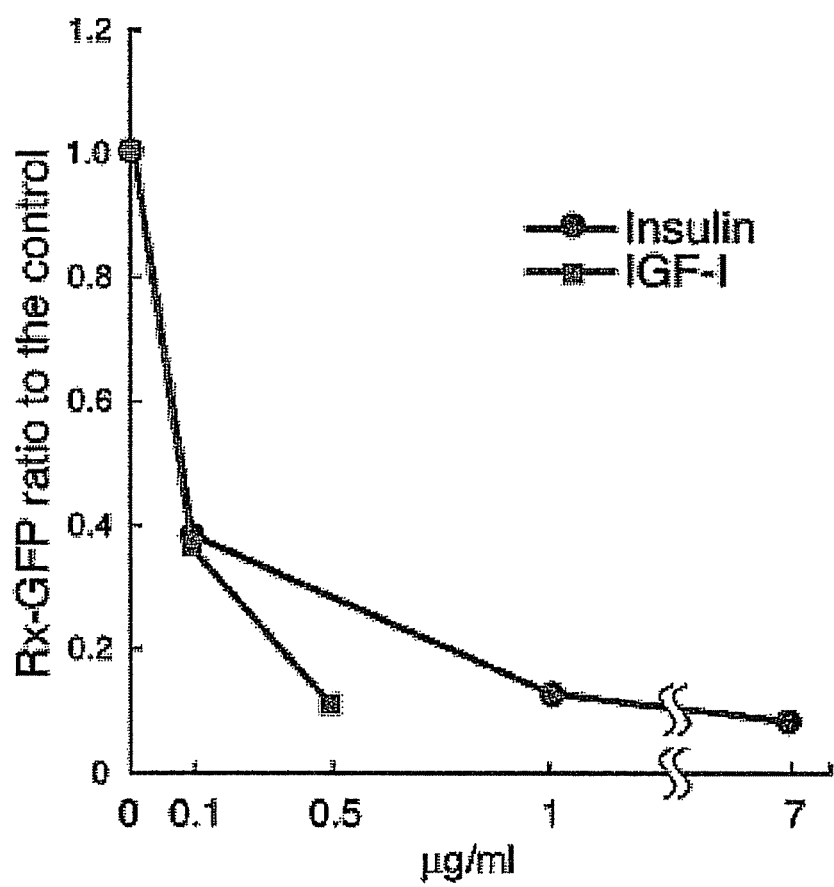
FIG. 14 shows results of a dose-response analysis of the influences of insulin and IGF-I on Rx-GFP ES cells cultured by SFEBq/gfCDM. From the start of differentiation culture, the cells were cultured along with insulin or IGF-I at the indicated concentrations, and the percentage of Rx-GFP$^+$ cells was analyzed by FACS on day 7. Shown are relative ratios with the percentage of Rx-GFP$^+$ for a control (insulin-free gfCDM) taken as 1.0.

With the addition of 7 µg/ml of insulin, the Rx-GFP positivity rate fell to less than 5%. Similar differentiation inhibition was also noted with the addition of 0.5 µg/ml of IGF, which is structurally closely related to insulin (FIG. 14). These show that the absence of insulin and substances similar thereto in the medium is important to the medium for selective induction of differentiation into hypothalamic progenitor cells.

Figure 15:
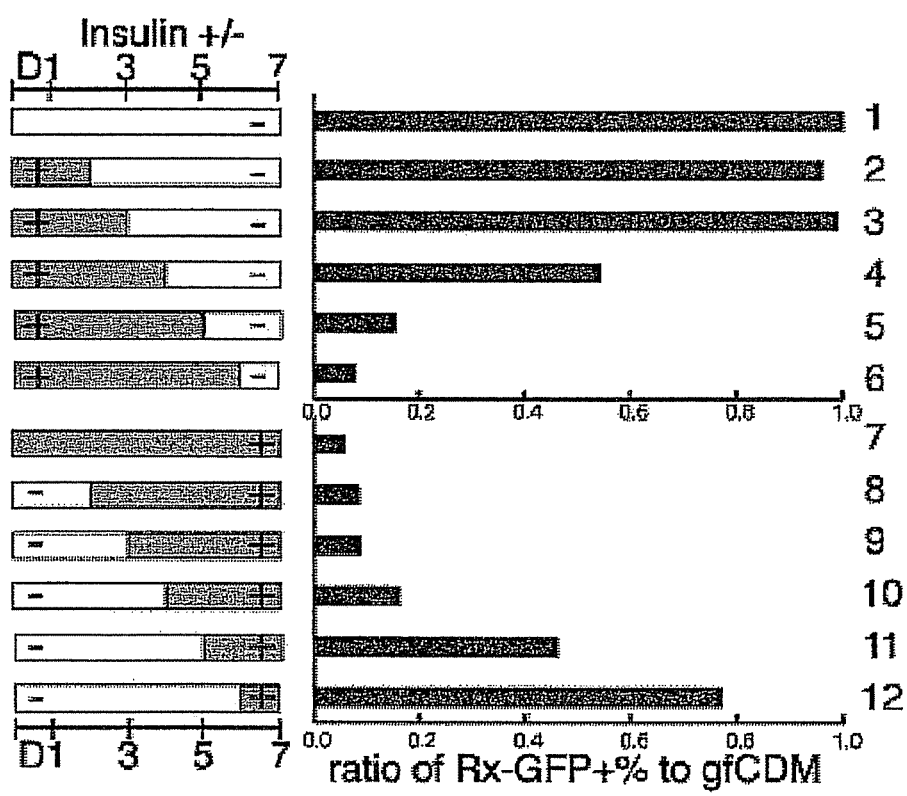
FIG. 15 shows results of a time-window analysis of the influences of insulin on the percentage of Rx-G FP$^+$ (FACS on day 7). Insulin (7 μg/ml) was removed (upper graph) or added (lower graph), as indicated on the left bar. The ratio of the percentage of Rx-GFP$^+$ in the presence of insulin to the percentage of Rx-GFP in an SFEBq/gfCDM culture (1 on the horizontal scale; 1.0) is shown on the right side of the graph.

A time-window analysis (FIG. 15) showed that the presence of insulin in CDM during the first 3 days had almost no inhibitory effect on Rx-GFP$^+$%, but when insulin was present after day 4, Rx-GFP$^+$% decreased substantially. Conversely, on day 5 or before, addition of insulin to gfCDM suppressed the expression of Rx-GFP. This suggests that the absence of a high insulin signal between day 4 and day 5 is important to efficient Rx expression.

Figure 16:
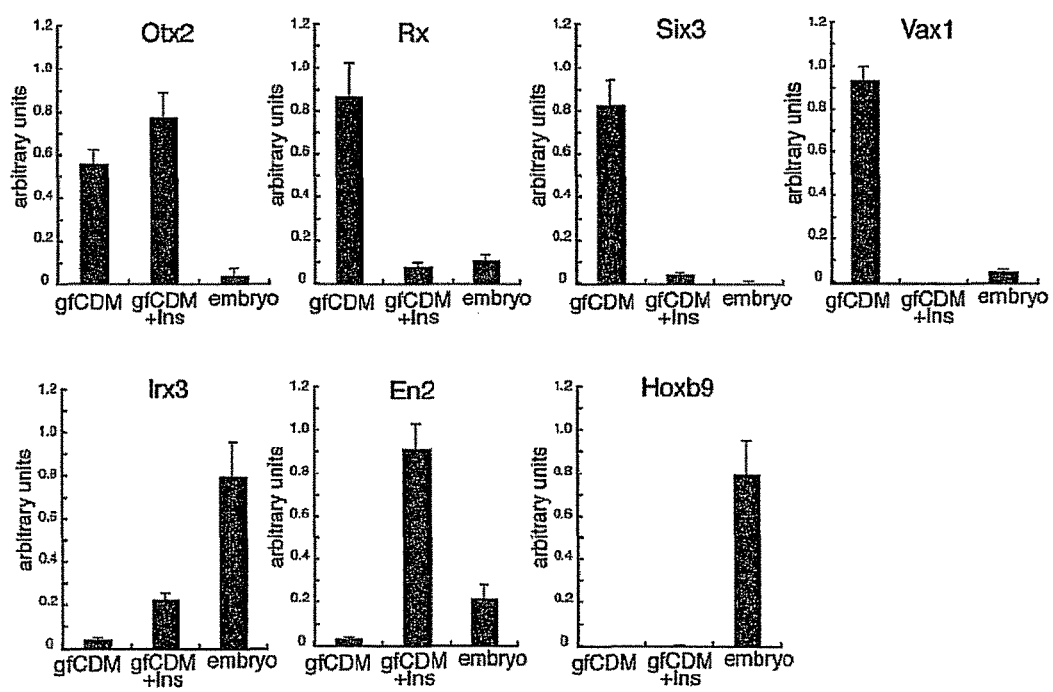
FIG. 16 shows the influences of insulin on the expression of the indicated marker genes.

When the effects of insulin on the expression of other marker genes in the SFEBq culture product were analyzed by qPCR, it was shown that insulin had a suppressive effect on the expression of the most rostral CNS marker, and that the expression of a caudal marker was induced moderately by insulin treatment (FIG. 16).

Figure 17:
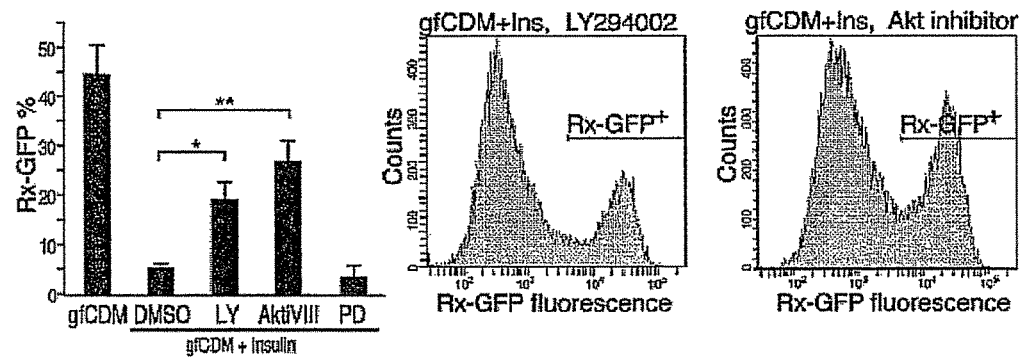
FIG. 17 shows the influences of inhibitors of the insulin signal transduction pathway on ES cells cultured by SFEBq in gfCDM with or without insulin (7 μg/ml). Statistical significance versus a control (gfCDM+insulin, containing DMSO) was evaluated by the Dunnette test. *, $P<0.05$; **, $P<0.01$.

The inhibitory effect of the addition of 7 µg/ml of insulin was antagonized by the addition of the PI3K inhibitor LY294002 (5 µM) or the addition of Akt inhibitor VIII (2 µM), resulting in recoveries to about 20% and 28%, respectively. However, with the MAPK inhibitor PD98059 (0.5-10 µM), antagonism of the inhibitory effect of insulin was not noted (FIG. 17). This suggests that with an insulin-containing differentiation medium, it is possible to induce differentiation of hypothalamic progenitor cells from ES cells by adding a PI3K inhibitor or an Akt inhibitor, or both. Insulin is contained in many serum-free media; the ability to antagonize the differentiation inhibitory action of insulin by this addition of an inhibitor is an important methodology.

Example 16

Differentiation of Dorsal and Ventral Hypothalamic Nerve Cells from Hypothalamic Progenitor Cells Produced from ES Cells (Method)

Rx-GFP ES cells were differentiation-induced by the SFEBq/gfCDM method under the same culturing conditions as Example 14 for 7 days, after which Rx-GFP-positive cells and Rx-GFP-negative cells were fractionated by FACS. The cells of each fraction were dispensed to a non-cell-adhesive 96-well culture plate at 2500-5000 cells per well, and further cultured using a DMEM/F12 medium supplemented with 7 g/L glucose, 10% KSR and penicillin/streptomycin for 3 days. The cells fractionated in this well formed re-aggregate masses within a half day. Three days later, half the medium was replaced with a DFNB medium (a DMEM/F12 supplemented with 7 g/l of glucose, 1×N2 supplement and 1×B27 supplement) supplemented with 10 ng/ml of CNTF, and the cells were further cultured for 3 days.

After cultivation for a total of 13 days, the re-aggregate masses were prepared as frozen sections, and the properties of the differentiated cells were analyzed by a fluorescent immunostaining method. For evaluating the effect of Shh, 30 nM Shh was added from 4 days after the start of cultivation.

(Results)

In the non-Shh-treated Rx-GFP-positive re-aggregate masses, 45% of the cells expressed the dorsal hypothalamus marker Otp, whereas the expression was not noted in the cells from the Rx-GFP-negative fraction. The expression of Otp in the Rx-GFP-positive fraction was strongly suppressed by the Shh treatment (7%). Meanwhile, in the Shh-treated Rx-GFP-positive re-aggregate masses, a large number of cells that express two proteins called Nkx2.1 and SF1, which are ventral hypothalamus markers, were noted (23% of the cells), whereas in the non-Shh-treated Rx-GFP-positive re-aggregate masses, little of such cells were noted. The expression of the dorsal marker Pax6 agreed with this result. With the treatment with the Shh signal inhibitor Cyclopamine, the reverse result compared with the Shh treatment was obtained in regard to the expression of these markers (not illustrated).

The results above demonstrated that hypothalamic cells derived from ES cells differentiated by SFEBq/gfCDM have the characters of the dorsal hypothalamus under Shh-free conditions, and have the characters of the ventral hypothalamus when treated with Shh. The same effects as with Shh were obtained when the Shh receptor agonist Purmorphamine (0.5 μM; Calbiochem) was used in place of Shh.

Example 17

Differentiation of Vasopressin-Producing Endocrine Cells from Hypothalamic Progenitor Cells Produced from ES Cells (Methods)

Typical nerve cells derived from the dorsal hypothalamus are the vasopressin-producing endocrine cells that are present in the paraventricular nucleus and the supraoptic nucleus. After Rx-GFP ES cells were differentiation-induced by the SFEBq/gfCDM method for 7 days in the same manner as Example 16, Rx-GFP-positive cells were fractionated by FACS. These were cultured as re-aggregate masses until day 13 in the same manner as Example 16, after which these were further cultured on Culture Insert (Transwell; Corning) for 12 days. The medium used was a DFNB medium supplemented with 10 ng/ml of CNTF. The properties of the neurons were examined by a fluorescent immunostaining method. Meanwhile, the vasopressin secreted in response to an artificial cerebrospinal fluid at a high potassium concentration (100 mM) was quantified by radioimmunoassay (2-immunostaining method).

(Results)

Figure 18:
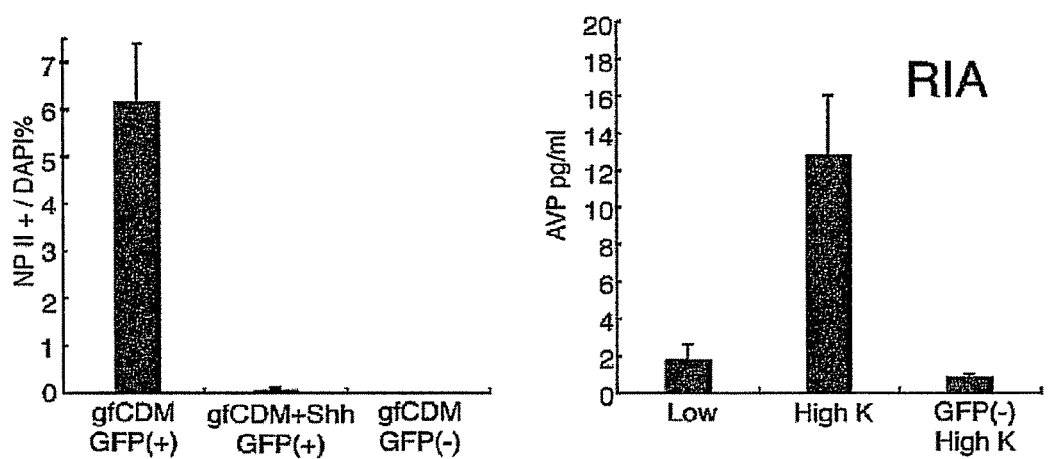
FIG. 18 shows the formation of vasopressin-producing endocrine cells from hypothalamic neuron progenitor cells. (Left) NP II$^+$ neurons observed in GFP$^+$ aggregate masses cultured by gfCDM. (Right) Analysis of AVP release with stimulation of a high level of K$^+$. AVP concentrations in an acclimation medium were measured by RIA.

In the fluorescent immunostaining method, a large number of large neurons positive for a vasopressin antibody (anti-NP II antibody) (cell body 20-30 μM in diameter) were detected (6% of all cells). When the neurons were cultured at 37° C. in an artificial cerebrospinal fluid at a high potassium concentration (100 mM), the release of about 7 μg of vasopressin from 10 cell masses was detected in 10 minutes (FIG. 18).

This shows that it is possible to differentiation-induce hypothalamic endocrine cell progenitor cells from ES cells by the SFEBq/gfCDM method, and that by differentiation-maturing them, neurons that actually produce the hormone can be produced.

Example 18

Differentiation of Other Hypothalamic Neurons from Hypothalamic Progenitor Cells Produced from ES Cells (Method)

Rx-GFP ES cells were subjected to SFEBq/gfCDM culture with an Shh treatment by the same method as Example 16; 7 days later, Rx-GFP-positive cells were fractionated by FACS. These were cultured as a re-aggregate masses until day 13 in the same manner as Example 16, after which these were further dispersed using a Neural Tissue Dissociation kit (SUMILON), plated to a culture plate coated with poly-D-lysine/laminin/fibronectin at 20000 cells/cm$^2$, and cultured with DFNB+50 ng/ml BDNF until day 25. The properties of the differentiated neurons were analyzed by a fluorescent immunostaining method.

(Results)

In the cultivation with the Shh treatment, no vasopressin-producing endocrine cells were noted, but a plurality of kinds of neurons having the properties of cells derived from the ventral hypothalamus were identified instead. They included medial ventral nuclear neurons, which co-express SF1 and GluT2 (13% of the differentiation-induced neurons; said to be neurons that serve as the satiety center in the hypothalamus), A12 type dopamine neurons, which co-express TH (tyrosine hydroxylase) and Nkx2.1 (14% of the differentiation-induced neurons; known to act to adjust pituitary prolactin secretion in the hypothalamus and the like), arcuate nuclear neurons, which co-express AgRP and NPY (1.5% of the differentiation-induced neurons; controls eating behavior), Orexin-positive neurons (about 0.5% of the differentiation-induced neurons; controls eating behavior) and the like.

These results show that by combining the Shh treatment with the SFEBq/gfCDM method, ventral hypothalamic neurons, which serve as the center that controls various behaviors and endocrine events, can be produced from ES cells.

Example 19

Induction of Differentiation of Hypothalamic Progenitor Cells from a Human ES Cell by a Modified SFEBq/gfCDM Method (Method)

Human ES cells (KhES#1; established by Professor Nakatsuji at Kyoto University) were cultured for maintenance as reported previously (Ueno et al., PNAS 2006). Regarding differentiation induction, as described in Example 13, when human ES cells are dispersed in SFEBq/gfCDM, and thereafter subjected to re-aggregation suspension culture, most of them die and no proliferation occurs. This was avoided by combining the following two methods. One is to add a ROCK inhibitor that was reported by the present inventors to suppress cell death during dispersion suspension culture (Y-27632; Watanabe et al., Nature Biotechnology 2007) to the medium from the start of cultivation. The other is to add insulin to accentuate cell proliferation. However, since the latter can inhibit the induction of differentiation into the hypothalamus, Akt inhibitor VIII, which antagonizes the inhibitory effect thereof, was added to the medium. This improvement makes it possible to culture and proliferate human ES cells by the SFEBq method.

Specifically, using the differentiation medium of Example 13 supplemented with 7 μg/ml of insulin, 50 μM Y-27632, the Wnt inhibitor Dkk1 (100 ng/ml; R&D), the Nodal inhibitor SB431542 (1 μM; Sigma), and the BMP inhibitor BMPRFc (1 μg/ml; R&D) as a differentiation medium, monodispersed human ES cells (Watanabe et al., Nature Biotechnology 2007) were dispensed to a non-cell-adhesive 96-well culture plate at 6000 cells/150 μl/well in the same manner as Example 13, and cultured at 37° C., 5% $CO_2$ for 18 days. Akt inhibitor VIII was added to the medium at a concentration of 2 μM from 9 days after the start of cultivation. Subsequently, the cells were further cultured for 13 days using the differentiation medium of Example 13 supplemented with 7 μg/ml of insulin and 2 μM of Akt inhibitor VIII.

The expression of hypothalamus gene markers was analyzed by a quantitative PCR method.

(Results)

After cultivation for a total of 31 days, in an analysis of the above-described cultured cell masses by a quantitative PCR method, significant expression of hypothalamus-specific genes such as Rx, Six3, Vax1, and Nkx2.1 was detected. Meanwhile, without addition of Akt inhibitor VIII, the expression decreased to 50% for Rx and to 25% for Vax1.

These results show that with the supplementary addition of Y-27632, insulin, and Akt inhibitor VIII, it is also possible to induce the differentiation of hypothalamic tissue from a human pluripotent stem cell as well by the SFEBq/gfCDM method.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

INDUSTRIAL APPLICABILITY

According to a method of the present invention, it is possible to efficiently induce the differentiation of nervous system cells, thus allowing cytotherapy to be applied for neurodegenerative diseases. Also, according to a method of the present invention, it is possible to efficiently induce the differentiation of forebrain tissue (particularly cerebral tissue), a task that has been difficult to achieve by the conventional method of differentiation, thus allowing cytotherapy to be applied for diseases associated with abnormalities of forebrain tissue.

Furthermore, according to the present invention, it is possible to produce a steric structure of a cerebral cortical tissue having a cerebral cortical network and a laminar structure in vitro. Therefore, the present invention is also highly useful in providing "tissue materials" for use in regenerative medicine, and in drug discovery and toxicity studies of the above-described pharmaceuticals and the like.

According to the present invention, it is possible to reduce the risk in the transplantation of cells obtained by culture of embryonic stem cell to the levels in allotransplantation, since an animal-derived cell is not used as an inductor.

According to the present invention, it is possible to obtain progenitor cells of neurons of the diencephalon, particularly of the hypothalamus, from a pluripotent stem cell of a mammal. In addition, further differentiated and matured cells can be obtained. The hypothalamus is the responsible site for medically important diseases, including endocrine abnormalities such as central diabetes insipidus, eating disorders (apastia/bulimia), sleep disorders and the like; production of these tissues from a pluripotent stem cell such as an ES cell in vitro would be helpful not only in regenerative medicine, but also in drug discovery and safety studies for endocrine abnormalities, eating disorders, sleep disorders and the like.

This application is based on patent application Nos. 2008-149880 (filing date: Jun. 6, 2008) and 2008-282299 (filing date: Oct. 31, 2008) both filed in Japan, the contents of which are incorporated in full herein.

The invention claimed is:

1. An in vitro method of inducing differentiation of mammalian pluripotent stem cells into cerebral cortex progenitor cells exhibiting epithelium-like structures and polarity, comprising;
   i) placing mammalian pluripotent stem cells in a non-cell adhesive spheroid well of a 96-well plate, or a spheroid well identical in shape and size to the wells of a 96-well plate, wherein said well comprises a serum-free, retinoic acid-free differentiation medium comprising a Wnt inhibitor and a Nodal inhibitor;
   ii) suspension-culturing the pluripotent stem cells from i), wherein the pluripotent stem cells form one pluripotent stem cell aggregate per well within 24 hours without centrifugation;
   iii) isolating a pluripotent stem cell aggregate from ii) and suspension-culturing said aggregate in serum-free, retinoic-acid free differentiation medium comprising a Wnt inhibitor and a Nodal inhibitor, wherein the aggregate differentiates into cerebral cortex progenitor cells exhibiting epithelium structures and polarity, express N-cadherin, CD-133, or laminin, and a higher percentage of said cells express Bf1 when compared to aggregates not produced in non-cell adhesive spheroid wells of a 96-well plate or a spheroid well identical in shape and size to the wells of a 96-well plate.

2. The method according to claim 1, wherein in step iii), the aggregates differentiate into cerebral cortex progenitor cells exhibiting epithelium structures and polarity within 12 hours.

3. The method according to claim 1, further comprising suspension-culturing the cerebral cortex progenitor cells exhibiting epithelium structures and polarity from step iii) with a serum-free, retinoic acid-free medium.

4. The method according to claim 3, wherein the suspension-culturing is performed for 60 hours to 46 days.

5. The method according to claim 3, wherein the serum-free and retinoic acid-free medium for the suspension-culturing step does not contain a Nodal signal promoter, a Wnt signal promoter, an FGF signal promoter, a BMP signal promoter, and insulin.

6. The method according to claim 5, wherein the serum-free and retinoic acid-free medium further contains selenious acid or a salt thereof.

7. The method according to claim 5, wherein the suspension-culturing step is performed for at least 7 days.

8. The method of claim 1, wherein the Wnt inhibitor in step i) or iii) is selected from the group consisting of Dkk1, Cerberus protein, Wnt receptor inhibitors, soluble Wnt receptors, Wnt antibodies, casein kinase inhibitors, and dominant negative Wnt protein.

9. The method of claim 1, wherein the Nodal inhibitor in step i) or iii) is selected from the group consisting of SB431542, Lefty-A, Lefty-B, Lefty-1, Lefty-2, soluble Nodal receptors, Nodal antibodies, and Nodal receptor inhibitors.

10. The method of claim 1, wherein the pluripotent stem cells are enclosed in non-cell-adhesive wells of a 96-well plate.

11. An in vitro method of inducing differentiation of mammalian pluripotent stem cells into cerebrum-specific neurons expressing TuJ1, and any one of Emx1, VGluT1, Telencephalin, GluR1, CamKII, Ctip2, and Tbr1, comprising:
   i) placing mammalian pluripotent stem cells in a non-cell adhesive spheroid well of a 96-well plate, or a spheroid well identical in shape and size to the wells of a 96-well plate, wherein said well comprises a serum-free, retinoic acid-free differentiation medium comprising a Wnt inhibitor and a Nodal inhibitor;
   ii) suspension-culturing the pluripotent stem cells from i), wherein the pluripotent stem cells form one pluripotent stem cell aggregate per well within 24 hours without centrifugation;
   iii) isolating a pluripotent stem cell aggregate from ii) and suspension-culturing said aggregate in serum-free, retinoic-acid free differentiation medium comprising a Wnt inhibitor and a Nodal inhibitor, wherein the aggregate differentiates into cerebral cortex progenitor cells exhibiting epithelium structures and polarity, express N-cadherin, CD-133, or laminin, and a higher percentage of said cells express Bf1 when compared to aggregates not produced in non-cell adhesive spheroid wells of a 96-well plate or a spheroid well identical in shape and size to the wells of a 96-well plate;

iv) isolating an aggregate from iii), enzymatically dispersing the aggregate and plating the resultant cells on a plate coated with an extracellular matrix;

v) culturing the cells from iv) in medium comprising bFGF and a supplement for neuronal cell culture;

vi) culturing the cells from v) in a medium comprising a supplement for neuronal cell culture, thereby producing cerebrum-specific neurons expressing TuJ1, and any one of Emx1, VGluT1, Telencephalin, GluR1, CamKII, Ctip2, and Tbr1.

12. The method of claim 11, wherein the supplement for neuronal cell culture in step v) is N2.

13. The method of claim 11, wherein the supplement for neuronal cell culture in step vi) is BDNF and NT3.

14. The method according to claim 11, wherein cerebrum-specific neurons of vi) are cerebral cortical nerve cells.

15. The method of claim 11, wherein the pluripotent stem cells are enclosed in non-cell-adhesive wells of a 96-well plate.

16. The method of claim 11, wherein the Wnt inhibitor in step i) or iii) is selected from the group consisting of Dkk1, Cerberus protein, Wnt receptor inhibitors, soluble Wnt receptors, Wnt antibodies, casein kinase inhibitors, and dominant negative Wnt protein.

17. The method of claim 11, wherein the Nodal inhibitor in step i) or iii) is selected from the group consisting of SB431542, Lefty-A, Lefty-B, Lefty-1, Lefty-2, soluble Nodal receptors, Nodal antibodies, and Nodal receptor inhibitors.

18. An in vitro method of producing hypothalamic progenitor cells expressing Rx, nestin, and optionally any one of Otx2, Six3, Vax1, Irx3, En2, and Hoxb9, said method comprising:

i) placing mammalian pluripotent stem cells in a non-cell adhesive spheroid well of a 96-well plate, or a spheroid well identical in shape and size to the wells of a 96-well plate, wherein said well comprises a serum-free, retinoic acid-free differentiation medium;

ii) suspension-culturing the pluripotent stem cells from i), wherein the pluripotent stem cells form one pluripotent stem cell aggregate per well within 24 hours without centrifugation; and iii) isolating a pluripotent stem cell aggregate from ii) and suspension-culturing said aggregate in a growth-factor free, chemically defined medium, thereby producing hypothalamic progenitor cells expressing Rx, nestin, and optionally any one of Otx2, Six3, Vax1, Irx3, En2, and Hoxb9.

19. An in vitro method of producing dorsal hypothalamus neural cells expressing Otp, said method comprising:

i) placing mammalian pluripotent stem cells in a non-cell adhesive spheroid well of a 96-well plate, or a spheroid well identical in shape and size to the wells of a 96-well plate, wherein said well comprises a serum-free, retinoic acid-free differentiation medium;

ii) suspension-culturing the pluripotent stem cells from i), wherein the pluripotent stem cells form one pluripotent stem cell aggregate per well within 24 hours without centrifugation; and iii) isolating a pluripotent stem cell aggregate expressing Rx from ii) and suspension-culturing said aggregate in a Shh-free medium comprising a supplement for neuronal cell culture;

thereby producing dorsal hypothalamus neural cells expressing Otp.

20. The method of claim 19, wherein the supplement for neuronal cell culture in step iii) is N2 and B27.

21. An in vitro method of producing a dome-shaped steric structure comprising Bf/Emx1-positive cerebral cortex nerve epithelium present as a continuous tissue and the nerve epithelium tissue has polarity, said method comprising:

i) placing mammalian pluripotent stem cells in a non-cell adhesive spheroid well of a 96-well plate, or a spheroid well identical in shape and size to the wells of a 96-well plate, wherein said well comprises a serum-free, retinoic acid-free differentiation medium comprising Wnt inhibitor and Nodal inhibitor;

ii) suspension-culturing the pluripotent stem cells from i), wherein the pluripotent stem cells form one pluripotent stem aggregate per well within 24 hours without centrifugation;

iii) isolating an pluripotent stem cell aggregate from ii) and suspension-culturing said aggregate in serum-free, retinoic-acid free differentiation medium comprising a Wnt inhibitor and a Nodal inhibitor, wherein the aggregate differentiates into cerebral cortex progenitor cells exhibiting epithelium structures and polarity, express N-cadherin, CD-133, or laminin, and a higher percentage of said cells express Bf1 when compared to aggregates not produced in non-cell adhesive spheroid wells of a 96-well plate or a spheroid well identical in shape and size to the wells of a 96-well plate;

iv) culturing the aggregate from iii) on a plate coated with an extracellular matrix in medium comprising a supplement for neuronal cell culture;

thereby producing a dome-shaped steric structure comprising the aggregates from iv), and wherein Bf/Emx1-positive cerebral cortex nerve epithelium is present as a continuous tissue and the nerve epithelium tissue has polarity in said steric structure.

22. The method of claim 21, wherein the supplement for neuronal cell culture in step iv) is B27.

23. The method of claim 21, wherein the Wnt inhibitor in step i) or iii) is selected from the group consisting of Dkk1, Cerberus protein, Wnt receptor inhibitors, soluble Wnt receptors, Wnt antibodies, casein kinase inhibitors, and dominant negative Wnt protein.

24. The method of claim 21, wherein the Nodal inhibitor in step i) or iii) is selected from the group consisting of SB431542, Lefty-A, Lefty-B, Lefty-1, Lefty-2, soluble Nodal receptors, Nodal antibodies, and Nodal receptor inhibitors.

25. An in vitro method of producing ventral hypothalamic neural cells expressing Sf1 and optionally Nkx2.1, said method comprising:

i) placing mammalian pluripotent stem cells in a non-cell adhesive spheroid well of a 96-well plate, or a spheroid well identical in shape and size to the wells of a 96-well plate, wherein said well comprises a serum-free, retinoic acid-free differentiation medium;

ii) suspension-culturing the pluripotent stem cells from i), wherein the pluripotent stem cells form one pluripotent cell stem aggregate per well within 24 hours without centrifugation; and iii) isolating a pluripotent stem cell aggregate expressing Rx from ii) and suspension-culturing said aggregate in a medium comprising Shh or a Shh agonist, and a supplement for neuronal cell culture;

thereby producing ventral hypothalamic neural cells expressing Sf1 and optionally Nkx2.1.

26. The method of claim 25, wherein the supplement for neuronal cell culture in step iii) is N2 and B27.

* * * * *